US009080207B2

(12) United States Patent
Handique et al.

(10) Patent No.: US 9,080,207 B2
(45) Date of Patent: *Jul. 14, 2015

(54) MICROFLUIDIC SYSTEM FOR AMPLIFYING AND DETECTING POLYNUCLEOTIDES IN PARALLEL

(71) Applicant: HANDYLAB, INC., Franklin Lakes, NJ (US)

(72) Inventors: Kalyan Handique, Ypsilanti, MI (US); Sundaresh N Brahmasandra, Ann Arbor, MI (US); Karthik Ganesan, Ann Arbor, MI (US); Jeff Williams, Chelsea, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/692,929

(22) Filed: Dec. 3, 2012

(65) Prior Publication Data

US 2013/0101990 A1    Apr. 25, 2013

Related U.S. Application Data

(63) Continuation of application No. 13/035,725, filed on Feb. 25, 2011, now Pat. No. 8,323,900, which is a continuation of application No. 11/985,577, filed on Nov. 14, 2007, now Pat. No. 7,998,708, which is a continuation-in-part of application No. 11/728,964, filed on Mar. 26, 2007.

(60) Provisional application No. 60/786,007, filed on Mar. 24, 2006, provisional application No. 60/859,284, filed on Nov. 14, 2006, provisional application No. 60/959,437, filed on Jul. 13, 2007.

(51) Int. Cl.
| | |
|---|---|
| *C12Q 1/68* | (2006.01) |
| *C12P 19/34* | (2006.01) |
| *B01L 3/00* | (2006.01) |
| *B01L 7/00* | (2006.01) |
| *B01L 9/00* | (2006.01) |
| *F16K 99/00* | (2006.01) |
| *G01N 35/00* | (2006.01) |

(52) U.S. Cl.
CPC ........... *C12Q 1/686* (2013.01); *B01L 3/502715* (2013.01); *B01L 3/502723* (2013.01); *B01L 3/502738* (2013.01); *B01L 7/52* (2013.01); *B01L 9/527* (2013.01); *F16K 99/0001* (2013.01); *F16K 99/003* (2013.01); *F16K 99/0032* (2013.01); *F16K 99/0044* (2013.01); *F16K 99/0061* (2013.01); *B01L 2200/027* (2013.01); *B01L 2200/10* (2013.01); *B01L 2200/147* (2013.01); *B01L 2200/148* (2013.01); *B01L 2200/16* (2013.01); *B01L 2300/021* (2013.01); *B01L 2300/045* (2013.01); *B01L 2300/0681* (2013.01); *B01L 2300/087* (2013.01); *B01L 2300/0816* (2013.01); *B01L 2300/0867* (2013.01); *B01L 2300/0887* (2013.01); *B01L 2300/1822* (2013.01); *B01L 2300/1827* (2013.01); *B01L 2300/1861* (2013.01); *B01L 2400/0442* (2013.01); *B01L 2400/0481* (2013.01); *B01L 2400/0487* (2013.01); *B01L 2400/0611* (2013.01); *B01L 2400/0677* (2013.01); *B01L 2400/0683* (2013.01); *F16K 2099/0084* (2013.01); *G01N 2035/00881* (2013.01)

(58) Field of Classification Search
CPC ........ C12Q 1/686; C12Q 1/6813; B01L 7/52; B01L 3/5027; B01L 3/502715; B01L 2200/027; B01L 2200/10; B01L 2200/147; B01L 2200/148; B01L 2200/16; B01L 2300/021; B01L 2300/045; B01L 2300/0681; B01L 2300/0816; B01L 2300/0867; B01L 2300/087; B01L 2300/0887; B01L 2300/1822; B01L 2300/1827; B01L 2300/1861

See application file for complete search history.

(56) References Cited

U.S. PATENT DOCUMENTS

| | | | |
|---|---|---|---|
| 1,434,314 | A | 10/1922 | Raich |
| 1,616,419 | A | 2/1927 | Wilson |
| 1,733,401 | A | 8/1930 | Lovekin |
| D189,404 | S | 12/1960 | Nicolle |
| 3,528,449 | A | 9/1970 | Witte et al. |

(Continued)

FOREIGN PATENT DOCUMENTS

| | | |
|---|---|---|
| CA | 2294819 | 1/1999 |
| CN | 103540518 | 1/2014 |

(Continued)

OTHER PUBLICATIONS

Bollet et al., "A simple method for the isolation of chromosomal DNA from Gram positive or acid-fast bacteria", Nucleic Acids Research, vol. 19, No. 8 (1991), p. 1955.

Brahmasandra et al., On-chip DNA detection in microfabricated separation systems, SPIE Conference on Microfluidic Devices and Systems, 1998, vol. 3515, pp. 242-251, Santa Clara, CA.

Breadmore et al., "Microchip-Based Purification of DNA from Biological Samples", Anal. Chem., vol. 75 (2003), pp. 1880-1886.

Brody et al., Diffusion-Based Extraction in a Microfabricated Device, Sensors and Actuators Elsevier, 1997, vol. A58, No. 1, pp. 13-18.

(Continued)

*Primary Examiner* — Young J Kim
(74) *Attorney, Agent, or Firm* — Knobbe, Martens, Olson & Bear, LLP

(57) ABSTRACT

The present technology provides for an apparatus for detecting polynucleotides in samples, particularly from biological samples. The technology more particularly relates to microfluidic systems that carry out PCR on nucleotides of interest within microfluidic channels, and detect those nucleotides. The apparatus includes a microfluidic cartridge that is configured to accept a plurality of samples, and which can carry out PCR on each sample individually, or a group of, or all of the plurality of samples simultaneously.

22 Claims, 61 Drawing Sheets

(56) References Cited

U.S. PATENT DOCUMENTS

| | | |
|---|---|---|
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,580,523 A | 12/1996 | Bard |
| 5,582,884 A | 12/1996 | Ball et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |

(56) References Cited

U.S. PATENT DOCUMENTS

| | | |
|---|---|---|
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-sill et al. |
| 5,846,396 A | 12/1998 | Zanzucchi et al. |
| 5,846,493 A | 12/1998 | Bankier et al. |
| 5,849,208 A * | 12/1998 | Hayes et al. ................. 216/94 |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| D438,311 S | 2/2001 | Yamanishi et al. |
| 6,190,619 B1 * | 2/2001 | Kilcoin et al. ................. 506/33 |

(56) References Cited

U.S. PATENT DOCUMENTS

| | | |
|---|---|---|
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,316,774 B1 | 11/2001 | Giebeler et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | McCormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 * | 3/2004 | Kellogg et al. ............ 435/287.2 |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |

(56) References Cited

U.S. PATENT DOCUMENTS

| | | |
|---|---|---|
| 6,752,966 B1 | 6/2004 | Chazan |
| 6,756,019 B1 | 6/2004 | Dubrow et al. |
| 6,764,859 B1 | 7/2004 | Kreuwel et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Shinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | McReynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skould |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| 7,553,671 B2 | 6/2009 | Sinclair et al. |
| D596,312 S | 7/2009 | Giraud et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,867,776 B2 | 1/2011 | Kennedy et al. |
| 7,892,819 B2 | 2/2011 | Wilding et al. |
| D637,737 S | 5/2011 | Wilson et al. |
| 7,998,708 B2 * | 8/2011 | Handique et al. ............ 435/91.2 |
| 8,105,783 B2 * | 1/2012 | Handique .................... 435/6.12 |
| 8,110,158 B2 | 2/2012 | Handique |
| 8,133,671 B2 | 3/2012 | Williams et al. |
| 8,182,763 B2 | 5/2012 | Duffy et al. |
| 8,273,308 B2 | 9/2012 | Handique et al. |
| D669,597 S | 10/2012 | Cavada et al. |
| 8,323,584 B2 | 12/2012 | Ganesan |
| 8,323,900 B2 * | 12/2012 | Handique et al. ............ 435/6.12 |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |

(56) References Cited

U.S. PATENT DOCUMENTS

| | | | |
|---|---|---|---|
| 8,473,104 B2 | 6/2013 | Handique et al. | |
| D692,162 S | 10/2013 | Lentz et al. | |
| 8,679,831 B2 | 3/2014 | Handique et al. | |
| 8,685,341 B2 | 4/2014 | Ganesan | |
| 8,703,069 B2 | 4/2014 | Handique et al. | |
| 8,709,787 B2 | 4/2014 | Handique | |
| 8,710,211 B2 | 4/2014 | Brahmasandra et al. | |
| 8,734,733 B2 | 5/2014 | Handique | |
| 8,765,076 B2 | 7/2014 | Handique et al. | |
| 8,852,862 B2 | 10/2014 | Wu et al. | |
| 8,883,490 B2 | 11/2014 | Handique et al. | |
| 8,894,947 B2 | 11/2014 | Ganesan et al. | |
| 8,895,311 B1 | 11/2014 | Handique et al. | |
| 2001/0012492 A1 | 8/2001 | Acosta et al. | |
| 2001/0021355 A1 | 9/2001 | Baugh et al. | |
| 2001/0023848 A1 | 9/2001 | Gjerde et al. | |
| 2001/0038450 A1 | 11/2001 | McCaffrey et al. | |
| 2001/0046702 A1 | 11/2001 | Schembri | |
| 2001/0048899 A1 | 12/2001 | Marouiss et al. | |
| 2001/0055765 A1 | 12/2001 | O'Keefe et al. | |
| 2002/0001848 A1 | 1/2002 | Bedingham et al. | |
| 2002/0008053 A1 | 1/2002 | Hansen et al. | |
| 2002/0009015 A1 | 1/2002 | Laugharn et al. | |
| 2002/0015667 A1 | 2/2002 | Chow | |
| 2002/0021983 A1 | 2/2002 | Comte et al. | |
| 2002/0037499 A1 | 3/2002 | Quake et al. | |
| 2002/0039783 A1 | 4/2002 | McMillan et al. | |
| 2002/0053399 A1 | 5/2002 | Soane et al. | |
| 2002/0054835 A1 | 5/2002 | Robotti et al. | |
| 2002/0055167 A1 | 5/2002 | Pourahmadi et al. | |
| 2002/0058332 A1 | 5/2002 | Quake et al. | |
| 2002/0060156 A1 | 5/2002 | Mathies et al. | |
| 2002/0068357 A1 | 6/2002 | Mathies et al. | |
| 2002/0141903 A1 | 10/2002 | Parunak et al. | |
| 2002/0142471 A1 | 10/2002 | Handique et al. | |
| 2002/0143297 A1 | 10/2002 | Francavilla et al. | |
| 2002/0143437 A1 | 10/2002 | Handique et al. | |
| 2002/0155477 A1 | 10/2002 | Ito | |
| 2002/0169518 A1 | 11/2002 | Luoma et al. | |
| 2002/0187557 A1 | 12/2002 | Hobbs et al. | |
| 2003/0019522 A1 | 1/2003 | Parunak | |
| 2003/0022392 A1 | 1/2003 | Hudak | |
| 2003/0049174 A1 | 3/2003 | Ganesan | |
| 2003/0049833 A1 | 3/2003 | Chen et al. | |
| 2003/0064507 A1 | 4/2003 | Gallagher et al. | |
| 2003/0070677 A1 | 4/2003 | Handique et al. | |
| 2003/0072683 A1 | 4/2003 | Stewart et al. | |
| 2003/0073106 A1 | 4/2003 | Johansen et al. | |
| 2003/0083686 A1 | 5/2003 | Freeman et al. | |
| 2003/0087300 A1 | 5/2003 | Knapp et al. | |
| 2003/0096310 A1 | 5/2003 | Hansen et al. | |
| 2003/0127327 A1 | 7/2003 | Kurnik | |
| 2003/0136679 A1 | 7/2003 | Bohn et al. | |
| 2003/0186295 A1 | 10/2003 | Colin et al. | |
| 2003/0190608 A1 | 10/2003 | Blackburn et al. | |
| 2003/0199081 A1 | 10/2003 | Wilding et al. | |
| 2003/0211517 A1 | 11/2003 | Carulli et al. | |
| 2004/0014202 A1 | 1/2004 | King et al. | |
| 2004/0014238 A1 | 1/2004 | Krug et al. | |
| 2004/0018119 A1 | 1/2004 | Massaro | |
| 2004/0022689 A1 | 2/2004 | Wulf et al. | |
| 2004/0029258 A1 | 2/2004 | Heaney et al. | |
| 2004/0029260 A1 | 2/2004 | Hansen et al. | |
| 2004/0037739 A1 | 2/2004 | McNeely et al. | |
| 2004/0053290 A1 | 3/2004 | Terbrueggen et al. | |
| 2004/0063217 A1 | 4/2004 | Webster et al. | |
| 2004/0072278 A1 | 4/2004 | Chou et al. | |
| 2004/0072375 A1 | 4/2004 | Gjerde et al. | |
| 2004/0086427 A1 | 5/2004 | Childers et al. | |
| 2004/0086956 A1 | 5/2004 | Bachur, Jr. | |
| 2004/0151629 A1 | 8/2004 | Pease et al. | |
| 2004/0157220 A1 | 8/2004 | Kurnool et al. | |
| 2004/0161788 A1 | 8/2004 | Chen et al. | |
| 2004/0189311 A1 | 9/2004 | Glezer et al. | |
| 2004/0200909 A1 | 10/2004 | McMillan et al. | |
| 2004/0209331 A1 | 10/2004 | Ririe | |
| 2004/0209354 A1 | 10/2004 | Mathies et al. | |
| 2004/0219070 A1 | 11/2004 | Handique | |
| 2004/0235154 A1 | 11/2004 | Oh et al. | |
| 2004/0240097 A1 | 12/2004 | Evans | |
| 2005/0009174 A1 | 1/2005 | Nikiforov et al. | |
| 2005/0013737 A1 | 1/2005 | Chow et al. | |
| 2005/0041525 A1 | 2/2005 | Pugia et al. | |
| 2005/0042639 A1 | 2/2005 | Knapp et al. | |
| 2005/0048540 A1 | 3/2005 | Inami et al. | |
| 2005/0058574 A1 | 3/2005 | Bysouth et al. | |
| 2005/0058577 A1 | 3/2005 | Micklash et al. | |
| 2005/0069898 A1 | 3/2005 | Moon et al. | |
| 2005/0084424 A1 | 4/2005 | Ganesan et al. | |
| 2005/0106066 A1 | 5/2005 | Saltsman et al. | |
| 2005/0121324 A1 | 6/2005 | Park et al. | |
| 2005/0129580 A1 | 6/2005 | Swinehart et al. | |
| 2005/0133370 A1 | 6/2005 | Park et al. | |
| 2005/0135655 A1 | 6/2005 | Kopf-sill et al. | |
| 2005/0142036 A1 | 6/2005 | Kim et al. | |
| 2005/0152808 A1 | 7/2005 | Ganesan | |
| 2005/0170362 A1 | 8/2005 | Wada et al. | |
| 2005/0186585 A1 | 8/2005 | Juncosa et al. | |
| 2005/0202470 A1 | 9/2005 | Sundberg et al. | |
| 2005/0202504 A1 | 9/2005 | Anderson et al. | |
| 2005/0208676 A1 | 9/2005 | Kahatt | |
| 2005/0214172 A1 | 9/2005 | Burgisser | |
| 2005/0220675 A1 | 10/2005 | Reed et al. | |
| 2005/0227269 A1 | 10/2005 | Lloyd et al. | |
| 2005/0233370 A1 | 10/2005 | Ammann et al. | |
| 2005/0238545 A1 | 10/2005 | Parce et al. | |
| 2005/0272079 A1 | 12/2005 | Burns et al. | |
| 2006/0041058 A1 | 2/2006 | Yin et al. | |
| 2006/0057039 A1 | 3/2006 | Morse et al. | |
| 2006/0057629 A1 | 3/2006 | Kim | |
| 2006/0062696 A1 | 3/2006 | Chow et al. | |
| 2006/0094108 A1 | 5/2006 | Yoder et al. | |
| 2006/0113190 A1 | 6/2006 | Kurnik | |
| 2006/0133965 A1 | 6/2006 | Tajima et al. | |
| 2006/0134790 A1 | 6/2006 | Tanaka et al. | |
| 2006/0148063 A1 | 7/2006 | Fauzzi et al. | |
| 2006/0165558 A1 | 7/2006 | Witty et al. | |
| 2006/0165559 A1 | 7/2006 | Greenstein et al. | |
| 2006/0166233 A1 | 7/2006 | Wu et al. | |
| 2006/0177376 A1 | 8/2006 | Tomalia et al. | |
| 2006/0177855 A1 | 8/2006 | Utermohlen et al. | |
| 2006/0183216 A1 | 8/2006 | Handique | |
| 2006/0201887 A1 | 9/2006 | Siddiqi | |
| 2006/0207944 A1 | 9/2006 | Siddiqi | |
| 2006/0210435 A1 | 9/2006 | Alavie et al. | |
| 2006/0246493 A1 | 11/2006 | Jensen et al. | |
| 2006/0246533 A1 | 11/2006 | Fathollahi et al. | |
| 2006/0269961 A1 | 11/2006 | Fukushima et al. | |
| 2007/0004028 A1 | 1/2007 | Lair et al. | |
| 2007/0009386 A1 | 1/2007 | Padmanabhan et al. | |
| 2007/0020699 A1 | 1/2007 | Carpenter et al. | |
| 2007/0026421 A1 | 2/2007 | Sundberg et al. | |
| 2007/0042441 A1 | 2/2007 | Masters et al. | |
| 2007/0092901 A1 | 4/2007 | Ligler et al. | |
| 2007/0098600 A1 | 5/2007 | Kayyem et al. | |
| 2007/0099200 A1 | 5/2007 | Chow et al. | |
| 2007/0104617 A1 | 5/2007 | Coulling et al. | |
| 2007/0154895 A1* | 7/2007 | Spaid et al. | 435/6 |
| 2007/0177147 A1 | 8/2007 | Parce | |
| 2007/0178607 A1 | 8/2007 | Prober et al. | |
| 2007/0184463 A1 | 8/2007 | Molho et al. | |
| 2007/0184547 A1 | 8/2007 | Handique et al. | |
| 2007/0196237 A1 | 8/2007 | Neuzil et al. | |
| 2007/0196238 A1 | 8/2007 | Kennedy et al. | |
| 2007/0199821 A1 | 8/2007 | Chow | |
| 2007/0215554 A1 | 9/2007 | Kreuwel et al. | |
| 2007/0218459 A1 | 9/2007 | Miller et al. | |
| 2007/0231213 A1 | 10/2007 | Prabhu et al. | |
| 2007/0243626 A1 | 10/2007 | Windeyer et al. | |
| 2007/0261479 A1 | 11/2007 | Spaid et al. | |
| 2007/0269861 A1 | 11/2007 | Williams et al. | |
| 2007/0292941 A1 | 12/2007 | Handique et al. | |
| 2008/0000774 A1 | 1/2008 | Park et al. | |
| 2008/0017306 A1 | 1/2008 | Liu et al. | |

(56) References Cited

U.S. PATENT DOCUMENTS

| | | |
|---|---|---|
| 2008/0050804 A1 | 2/2008 | Handique et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |
| 2009/0223925 A1 | 9/2009 | Morse et al. |
| 2010/0009351 A1 | 1/2010 | Brahmasandra et al. |
| 2010/0173393 A1 | 7/2010 | Handique et al. |
| 2011/0008825 A1 | 1/2011 | Ingber et al. |
| 2011/0027151 A1 | 2/2011 | Handique et al. |
| 2011/0158865 A1 | 6/2011 | Miller et al. |
| 2011/0207140 A1 | 8/2011 | Handique et al. |
| 2011/0210257 A9 | 9/2011 | Handique et al. |
| 2012/0022695 A1 | 1/2012 | Handique et al. |
| 2012/0085416 A1 | 4/2012 | Ganesan |
| 2012/0122108 A1 | 5/2012 | Handique |
| 2012/0160826 A1 | 6/2012 | Handique |
| 2012/0183454 A1 | 7/2012 | Handique |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0164832 A1 | 6/2013 | Ganesan et al. |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |
| 2014/0030798 A1 | 1/2014 | Wu et al. |
| 2014/0045186 A1 | 2/2014 | Gubatayao et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0297047 A1 | 10/2014 | Ganesan et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2014/0377850 A1 | 12/2014 | Handique et al. |

FOREIGN PATENT DOCUMENTS

| | | |
|---|---|---|
| DE | 19929734 | 12/1999 |
| DE | 19833293 C1 | 1/2000 |
| EP | 0365828 A2 | 5/1990 |
| EP | 0766256 | 4/1997 |
| EP | 1541237 A2 | 6/2005 |
| EP | 2372367 A1 | 10/2011 |
| FR | 2672301 | 8/1992 |
| FR | 2795426 | 12/2000 |
| JP | 58212921 A | 12/1983 |
| JP | S62-119460 | 5/1987 |
| JP | H01-502319 | 8/1989 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-211071 | 8/1996 |
| JP | H08-285859 | 11/1996 |
| JP | H09-325151 | 12/1997 |
| JP | H11-515106 | 12/1999 |
| JP | 2000-275255 | 10/2000 |
| JP | 2001-502319 | 2/2001 |
| JP | 2001-509437 | 7/2001 |
| JP | 3191150 B2 | 7/2001 |
| JP | 2001-515216 | 9/2001 |
| JP | 2001-527220 | 12/2001 |
| JP | 2002-503331 | 1/2002 |
| JP | 2002-215241 | 7/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-185584 | 7/2003 |
| JP | 2003-299485 | 10/2003 |
| JP | 2003-329693 | 11/2003 |
| JP | 2004-506179 A | 2/2004 |
| JP | 2004-150797 A | 5/2004 |
| JP | 2004-531360 A | 10/2004 |
| JP | 2004-361421 | 12/2004 |
| JP | 2004-536291 | 12/2004 |
| JP | 2005-009870 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192554 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2006-021156 A | 1/2006 |
| JP | 2006-094866 A | 4/2006 |
| JP | 2006-167569 | 6/2006 |
| JP | 2007-074960 | 3/2007 |
| JP | 2007-097477 | 4/2007 |
| JP | 2007-510518 | 4/2007 |
| JP | 2007-514405 A | 6/2007 |
| JP | 2007-178328 | 7/2007 |
| WO | WO 88/06633 | 9/1988 |
| WO | WO 90/12350 | 10/1990 |
| WO | WO 92/05443 | 4/1992 |
| WO | WO 94/11103 | 5/1994 |
| WO | WO 96/04547 | 2/1996 |
| WO | WO 97/05492 | 2/1997 |
| WO | WO 97/21090 | 6/1997 |
| WO | WO 98/00231 | 1/1998 |
| WO | WO 98/22625 | 5/1998 |
| WO | WO 98/49548 | 11/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/076661 | 9/2003 |
| WO | WO 2004/007081 | 1/2004 |
| WO | WO 2004/048545 | 6/2004 |
| WO | WO 2004/055522 | 7/2004 |
| WO | WO 2004/074848 | 9/2004 |

(56) References Cited

FOREIGN PATENT DOCUMENTS

| | | |
|---|---|---|
| WO | WO 2004/094986 | 11/2004 |
| WO | WO 2005/011867 | 2/2005 |
| WO | WO 2005/030984 | 4/2005 |
| WO | WO 2005/107947 | 11/2005 |
| WO | WO 2005/108620 | 11/2005 |
| WO | WO 2005/116202 | 12/2005 |
| WO | WO 2005/118867 | 12/2005 |
| WO | WO 2006/010584 | 2/2006 |
| WO | WO 2006/032044 | 3/2006 |
| WO | WO 2006/066001 | 6/2006 |
| WO | WO 2006/079082 | 7/2006 |
| WO | WO 2006/113198 | 10/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/091530 | 8/2007 |
| WO | WO 2007/112114 | 10/2007 |
| WO | WO 2008/030914 | 3/2008 |
| WO | WO 2009/012185 | 1/2009 |
| WO | WO 2010/118541 | 10/2010 |

OTHER PUBLICATIONS

Broyles et al., "Sample Filtration, Concentration, and Separation Integrated on Microfluidic Devices" Analytical Chemistry (American Chemical Society), (2003) vol. 75 No. 11: pp. 2761-2767.

Burns et al., An Integrated Nanoliter DNA Analysis Device, Science 282:484-487 (1998).

Carlen et al., "Paraffin Actuated Surface Micromachined Valve," in IEEE MEMS 2000 Conference, p. 381-385, Miyazaki, Japan, Jan. 2000.

Chung et al., "Microfluidic chip for high efficiency DNA extraction", Miniaturisation for Chemistry, Biology & Bioengineering, vol. 4, No. 2 (Apr. 2004), pp. 141-147.

Handique et al., On-Chip Thermopneumatic Pressure for Discrete Drop Pumping, Analytical Chemistry, American Chemical Society, Apr. 15, 2001, vol. 73, No. 8, 1831-1838.

Handique et al, "Microfluidic flow control using selective hydrophobic patterning", SPIE, vol. 3224, pp. 185-194 (1997).

Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique et al., "Mathematical Modeling of Drop Mixing in a Slit-Type Microchannel", J. Micromech. Microeng., 11:548-554 (2001).

Handique et al., "Nanoliter Liquid Metering in Microchannels Using Hydrophobic Patterns", Anal. Chem., 72:4100-4109 (2000).

He et al., Microfabricated Filters for Microfluidic Analytical Systems, Analytical Chemistry, American Chemical Society, 1999, vol. 71, No. 7, pp. 1464-1468.

Ibrahim et al., Real-Time Microchip PCR for Detecting Single-Base Differences in Viral and Human DNA, Analytical Chemistry, American Chemical Society, 1998, vol. 70, No. 9, pp. 2013-2017.

Khandurina et al., Microfabricated Porous Membrane Structure for Sample Concentration and Electrophoretic Analysis, Analytical Chemistry American Chemical Society, 1999, vol. 71, No. 9, pp. 1815-1819.

Kopp et al., Chemical Amplification: Continuous-Flow PCR on a Chip, www.sciencemag.org, 1998, vol. 280, pp. 1046-1048.

Kutter et al., Solid Phase Extraction on Microfluidic Devices, J. Microcolumn Separations, John Wiley & Sons, Inc., 2000, vol. 12, No. 2, pp. 93-97.

Lagally et al., Single-Molecule DNA Amplification and Analysis in an Integrated Microfluidic Device, Analytical Chemistry, American Chemical Society, 2001, vol. 73, No. 3 pp. 565-570.

Livache et al., "Polypyrrole DNA chip on a Silicon Device: Example of Hepatitis C Virus Genotyping", Analytical Biochemistry, vol. 255 (1998), pp. 188-194.

Mascini et al., "DNA electrochemical biosensors", Fresenius J. Anal. Chem., 369: 15-22, (2001).

Nakagawa et al., Fabrication of amino silane-coated microchip for DNA extraction from whole blood, J of Biotechnology, Mar. 2, 2005, vol. 116, pp. 105-111.

Northrup et al., A Miniature Analytical Instrument for Nucleic Acids Based on Micromachined Silicon Reaction Chambers, Analytical Chemistry, American Chemical Society, 1998, vol. 70, No. 5, pp. 918-922.

Oleschuk et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.

Plambeck et al., "Electrochemical Studies of Antitumor Antibiotics", J. Electrochem Soc.: Electrochemical Science and Technology (1984), 131(11): 2556-2563.

Roche et al. "Ectodermal commitment of insulin-producing cells derived from mouse embryonic stem cells" Faseb J (2005) 19: 1341-1343.

Ross et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.

Shoffner et al., Chip PCR.I. Surface Passivation of Microfabricated Silicon-Glass Chips for PCR, Nucleic Acids Research, Oxford University Press, 1996, vol. 24, No. 2, 375-379.

Smith et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Wang, "Survey and Summary, from DNA Biosensors to Gene Chips", Nucleic Acids Research, 28(16):3011-3016, (2000).

Waters et al., Microchip Device for Cell Lysis, Multiplex PCR Amplification, and Electrophoretic Sizing, Analytical Chemistry, American Chemical Society, 1998, vol. 70, No. 1, pp. 158-162.

Weigl et al., Microfluidic Diffusion-Based Separation and Detection, www.sciencemag.org, 1999, vol. 283, pp. 346-347.

Yoza et al., DNA extraction using bacterial magnetic particles modified with hyperbranched polyamidoamine dendrimer, Mar. 20, 2003, vol. 101, No. 3, 219-228.

Yoza et al., "Fully Automated DNA Extraction from Blood Using Magnetic Particles Modified with a Hyperbranched Polyamidomine Dendrimer", Journal of Bioscience and Bioengineering, 95(1):21-26, 2003.

International Search Report and Written Opinion dated Apr. 4, 2008 for PCT/US07/07513.

International Search Report and Written Opinion for PCT/US07/024022 dated Jan. 5, 2009.

Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.

Meyers, R.A., Molecular Biology and Biotechnology: A Comprehensive Desk Reference; VCH Publishers, Inc. New York, NY; (1995) pp. 418-419.

Kuo et al., "Remnant cationic dendrimers block RNA migration in electrophoresis after monophasic lysis", J Biotech. (2007) 129: 383-390.

Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.

Wu et al., "Polycationic dendrimers interact with RNA molecules: polyamine dendrimers inhibit the catalytic activity of *Candida* ribozymes", Chem Commun. (2005) 3: 313-315.

Zhou et al., "Cooperative binding and self-assembling behavior of cationic low molecular-weight dendrons with RNA molecules", Org Biomol Chem. (2006) 4(3): 581-585.

Zhou et al., "PANAM dendrimers for efficient siRNA delivery and potent gene silencing", Chem Comm.(Camb.) (2006) 22: 2362-2364.

\* cited by examiner

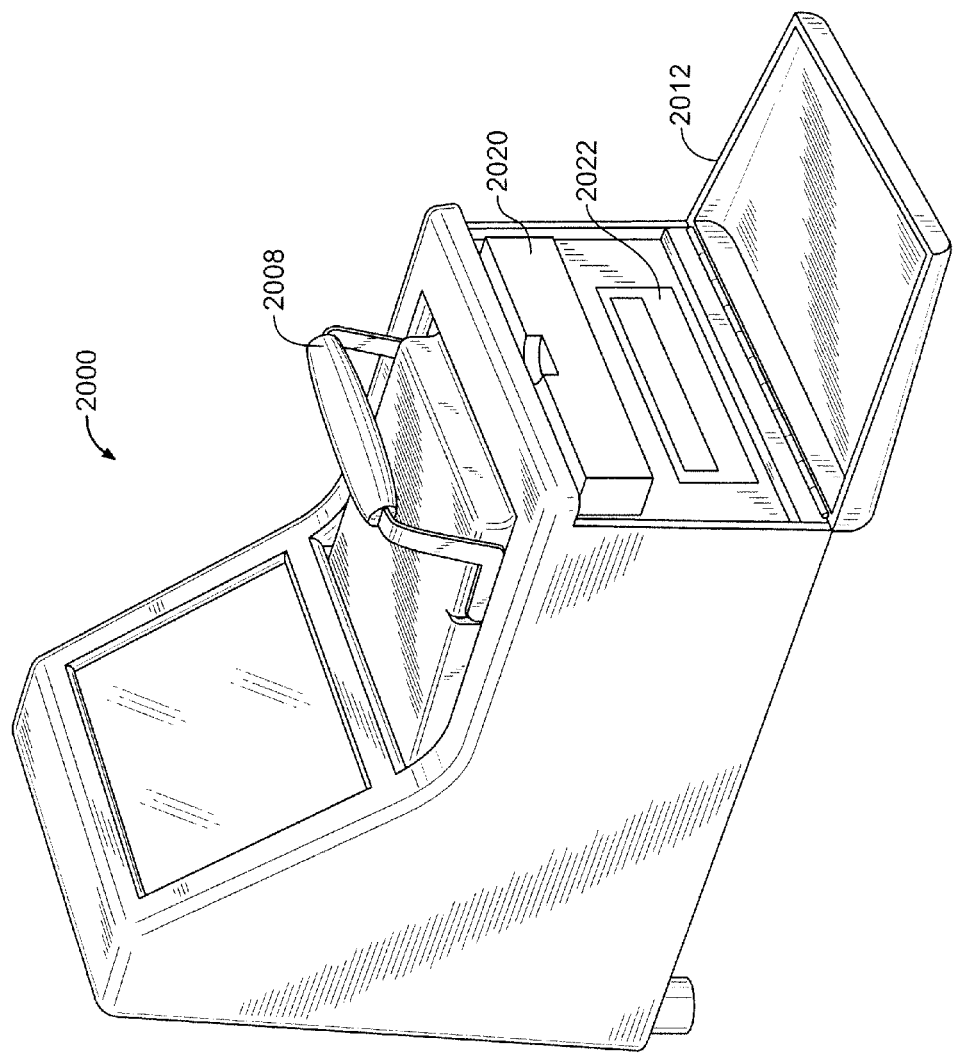

Capillary action of controlled volume of wax causes it to fill up the Wax up to the right interface without blocking the liquid flowable microchannel

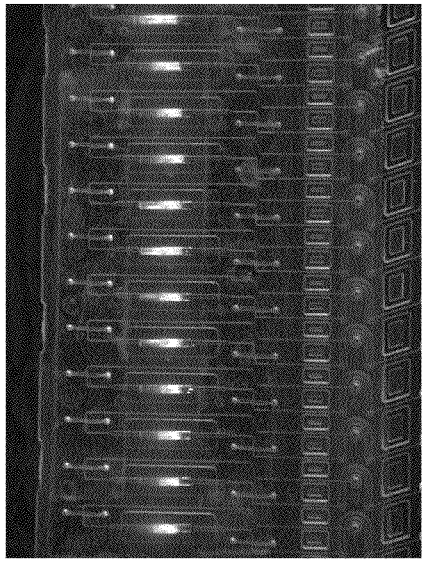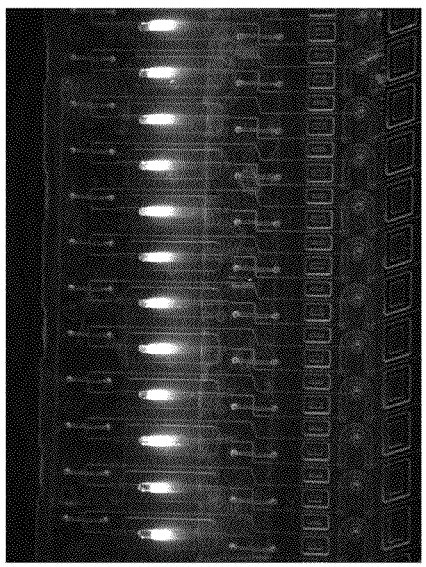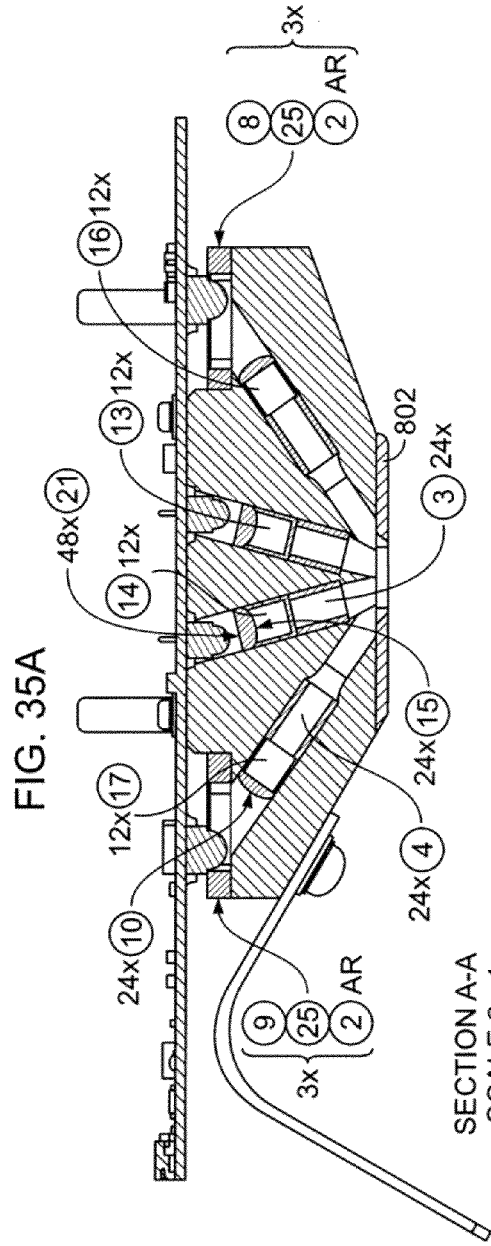
FIG. 35A
FIG. 35B
SECTION A-A
SCALE 2:1

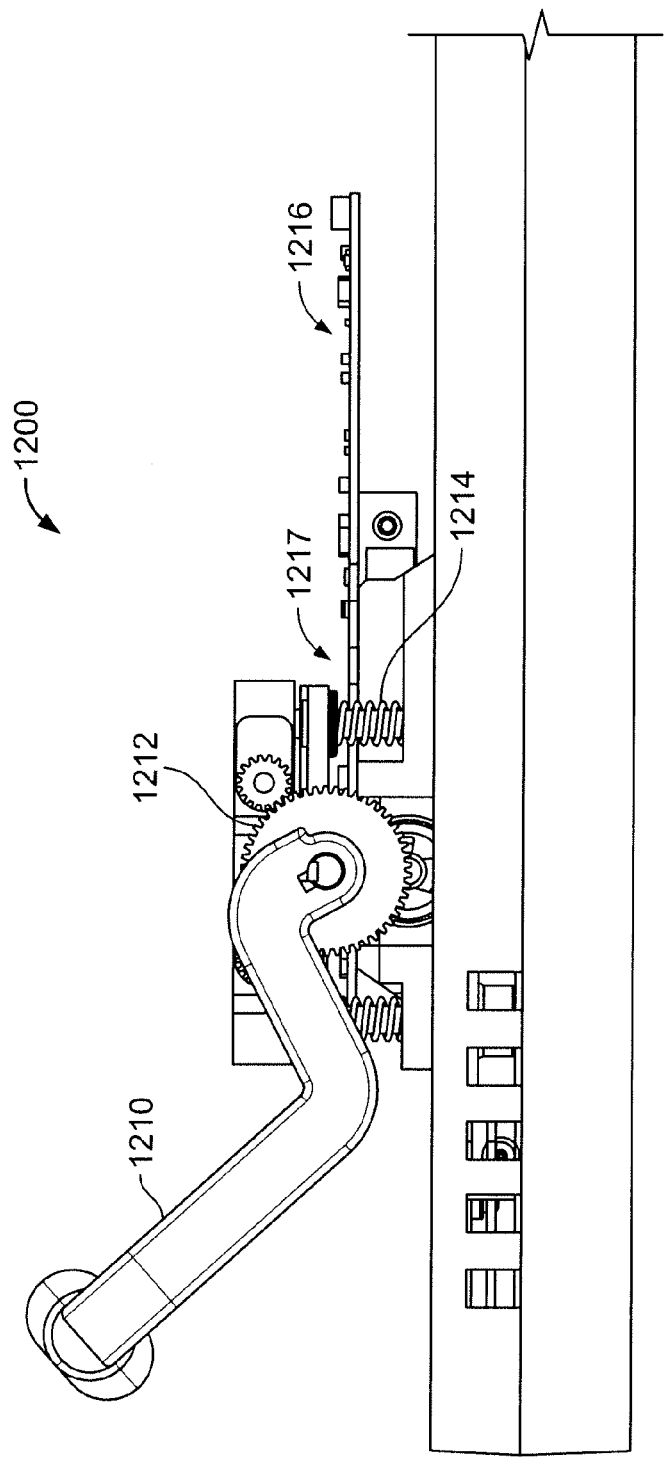

MICROFLUIDIC SYSTEM FOR AMPLIFYING AND DETECTING POLYNUCLEOTIDES IN PARALLEL

CROSS-REFERENCE TO RELATED APPLICATIONS

This application is a continuation of U.S. patent application Ser. No. 13/035,725, filed Feb. 25, 2011, which is a continuation of U.S. patent application Ser. No. 11/985,577, filed Nov. 14, 2007, now U.S. Pat. No. 7,998,708, which is a continuation-in-part of U.S. patent application Ser. No. 11/728,964, filed Mar. 26, 2007, which claims the benefit of U.S. Provisional Patent Application No. 60/786,007, filed Mar. 24, 2006, and U.S. Provisional Patent Application No. 60/859,284, filed Nov. 14, 2006. U.S. patent application Ser. No. 11/985,577 claims the benefit of U.S. Provisional Patent Application No. 60/859,284, filed Nov. 14, 2006, and U.S. Provisional Patent Application No. 60/959,437, filed Jul. 13, 2007. The disclosures of U.S. patent application Ser. No. 11/985,577, U.S. patent application Ser. No. 11/728,964, U.S. Provisional Patent Application No. 60/859,284, and U.S. Provisional Patent Application No. 60/959,437 are considered part of the disclosure of this application, and are incorporated by reference herein in their entirety.

TECHNICAL FIELD

The technology described herein generally relates to systems for detecting polynucleotides in samples, particularly from biological samples. The technology more particularly relates to microfluidic systems that carry out PCR on nucleotides of interest within microfluidic channels, and detect those nucleotides.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Sample preparation is a process that is susceptible to automation but is also relatively routinely carried out in almost any location. By contrast, steps such as PCR and nucleotide detection have customarily only been within the compass of specially trained individuals having access to specialist equipment.

There is a need for a method and apparatus of carrying out PCR and detection on prepared biological samples, and preferably with high throughput. In particular there is a need for an easy-to-use device that can deliver a diagnostic result on several samples in a short time.

The discussion of the background to the technology herein is included to explain the context of the technology. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present technology addresses systems for detecting polynucleotides in samples, particularly from biological samples. In particular, the technology relates to microfluidic systems that carry out PCR on nucleotides of interest within microfluidic channels, and detect those nucleotides.

An apparatus, comprising: a receiving bay configured to receive a microfluidic cartridge; at least one heat source thermally coupled to the cartridge and configured to carry out PCR on a microdroplet of polynucleotide-containing sample, in the cartridge; a detector configured to detect presence of one or more polynucleotides in the sample; and a processor coupled to the detector and the heat source, configured to control heating of one or more regions of the microfluidic cartridge.

A method of carrying out PCR on a plurality of polynucleotide-containing samples, the method comprising: introducing the plurality of samples in to a microfluidic cartridge, wherein the cartridge has a plurality of PCR reaction chambers configured to permit thermal cycling of the plurality of samples independently of one another; moving the plurality of samples into the respective plurality of PCR reaction chambers; and amplifying polynucleotides contained with the plurality of samples, by application of successive heating and cooling cycles to the PCR reaction chambers.

The details of one or more embodiments of the technology are set forth in the accompanying drawings and further description herein. Other features, objects, and advantages of the technology will be apparent from the description and drawings, and from the claims.

BRIEF DESCRIPTION OF THE DRAWINGS

FIGS. 6A-6E show exemplary embodiments of an apparatus;

FIG. 35A shows effects of aperturing on fluorescence intensity; FIG. 35B shows a detector in cross section with an exemplary aperture;

FIGS. 45A-45D show a force member associated with a detector;

Additional figures are illustrated within the examples, and are further described therein.

Like reference symbols in the various drawings indicate like elements.

DETAILED DESCRIPTION

Overview of Apparatus

The present technology relates to a system and related methods for amplifying, and carrying out diagnostic analyses on, polynucleotides (e.g., a DNA, RNA, mRNA, or rRNA) from biological samples. For example, the system and methods can determine whether a polynucleotide indicative of the presence of a particular pathogen (such as a bacterium or a virus) can be present. The polynucleotide may be a sample of genomic DNA, or may be a sample of mitochondrial DNA. The nucleotides are typically provided to the system having been isolated or released from particles such as cells in the sample. The system includes a disposable microfluidic cartridge containing multiple sample lanes in parallel and a reusable instrument platform (a PCR analyzer apparatus) that can actuate on-cartridge operations, can detect (e.g., by fluorescence detection) and analyze the products of the PCR amplification in each of the lanes separately, in all simultaneously, or in groups simultaneously, and, optionally, can display the results on a graphical user interface.

A system, microfluidic cartridge, heater unit, detector, kit, methods, and associated computer program product, are now further described.

By cartridge is meant a unit that may be disposable, or reusable in whole or in part, and that is configured to be used in conjunction with some other apparatus that has been suitably and complementarily configured to receive and operate on (such as deliver energy to) the cartridge.

By microfluidic, as used herein, is meant that volumes of sample, and/or reagent, and/or amplified polynucleotide are from about 0.1 µl to about 999 µl, such as from 1-100 µl or from 2-25 µl. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide.

Figure 1:
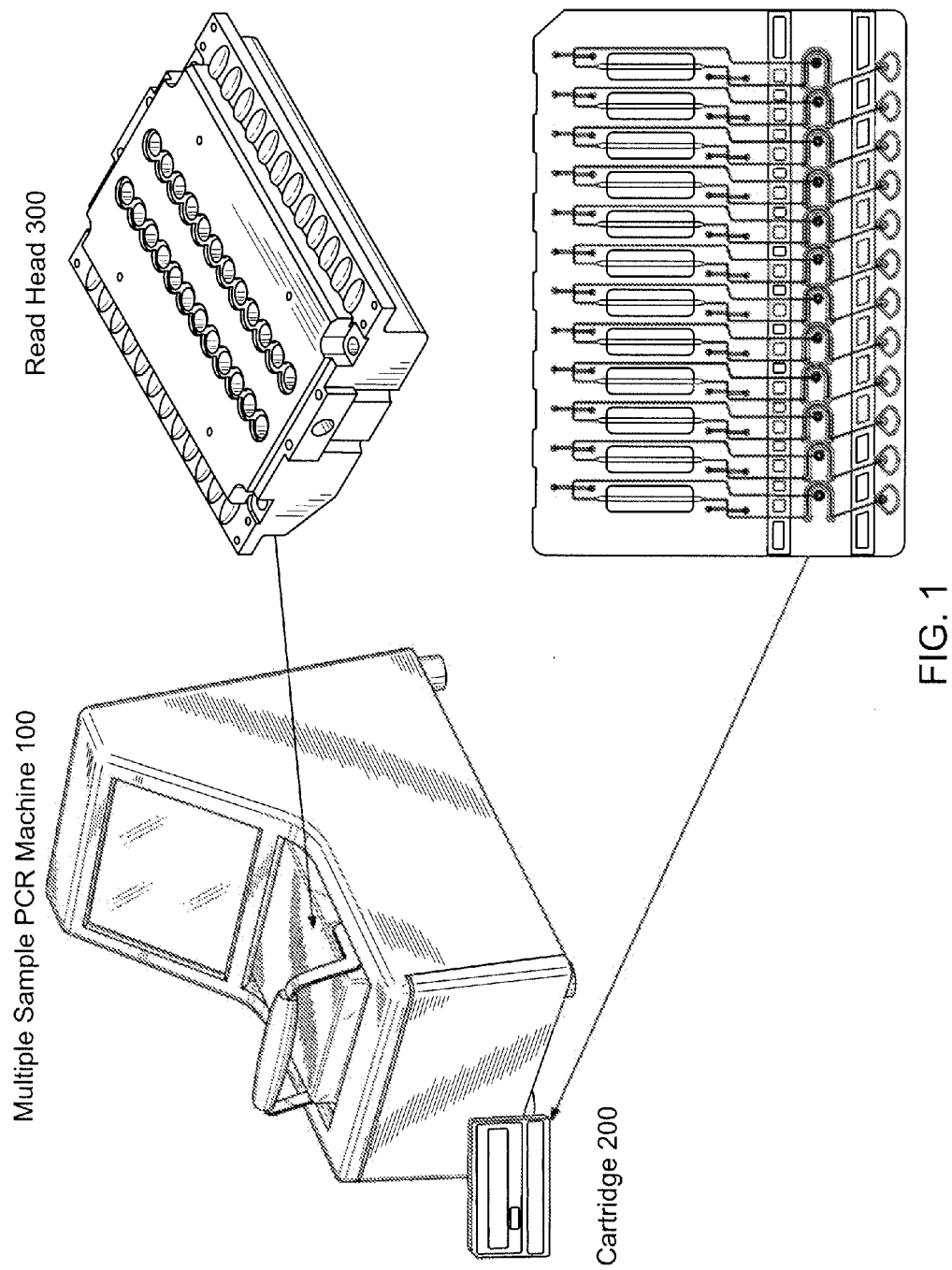
FIG. 1 shows an exemplary apparatus, a microfluidic cartridge, and a read head, as further described herein.
Figure 2:
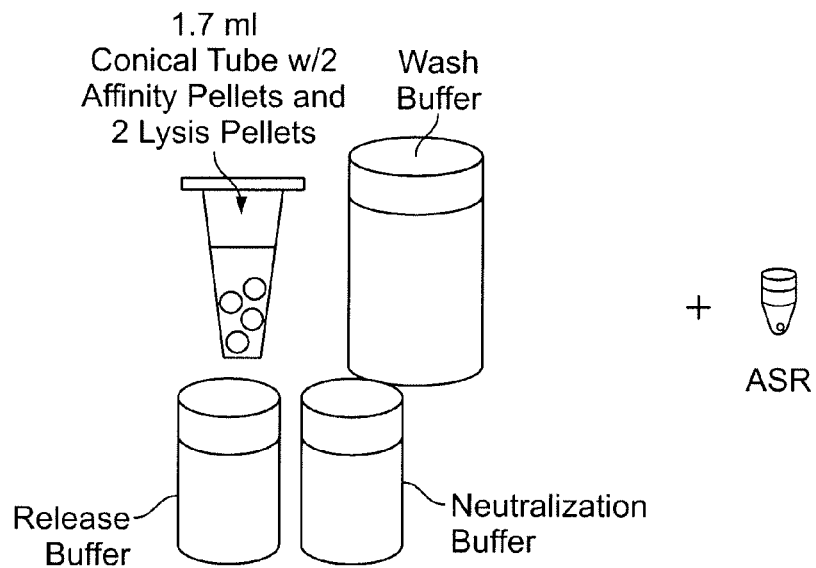
FIG. 2 shows an exemplary sample-preparation kit.

FIG. 1 shows a perspective view of an exemplary apparatus 100 consistent with those described herein, as well as various components thereof, such as exemplary cartridge 200 that contains multiple sample lanes, and exemplary read head 300 that contains detection apparatus for reading signals from cartridge 200. The apparatus 100 of FIG. 1 is able to carry out real-time PCR on a number of samples in cartridge 200 simultaneously. Preferably the number of samples is 12 samples, as illustrated with exemplary cartridge 200, though other numbers of samples such as 4, 8, 10, 16, 20, 24, 25, 30, 32, 36, 40, and 48 are within the scope of the present description. In preferred operation of the apparatus, a PCR-ready solution containing the sample, and, optionally, one or more analyte-specific reagents (ASR's) is prepared, as further described elsewhere (see, e.g., U.S. patent application publication 2006-0166233, incorporated herein by reference), prior to introduction into cartridge 200. An exemplary kit for preparing a PCR-ready sample, for use with the system described herein, the kit comprising buffers, lysis pellets, and affinity pellets, is shown in FIG. 2.

System Overview

Figure 3:
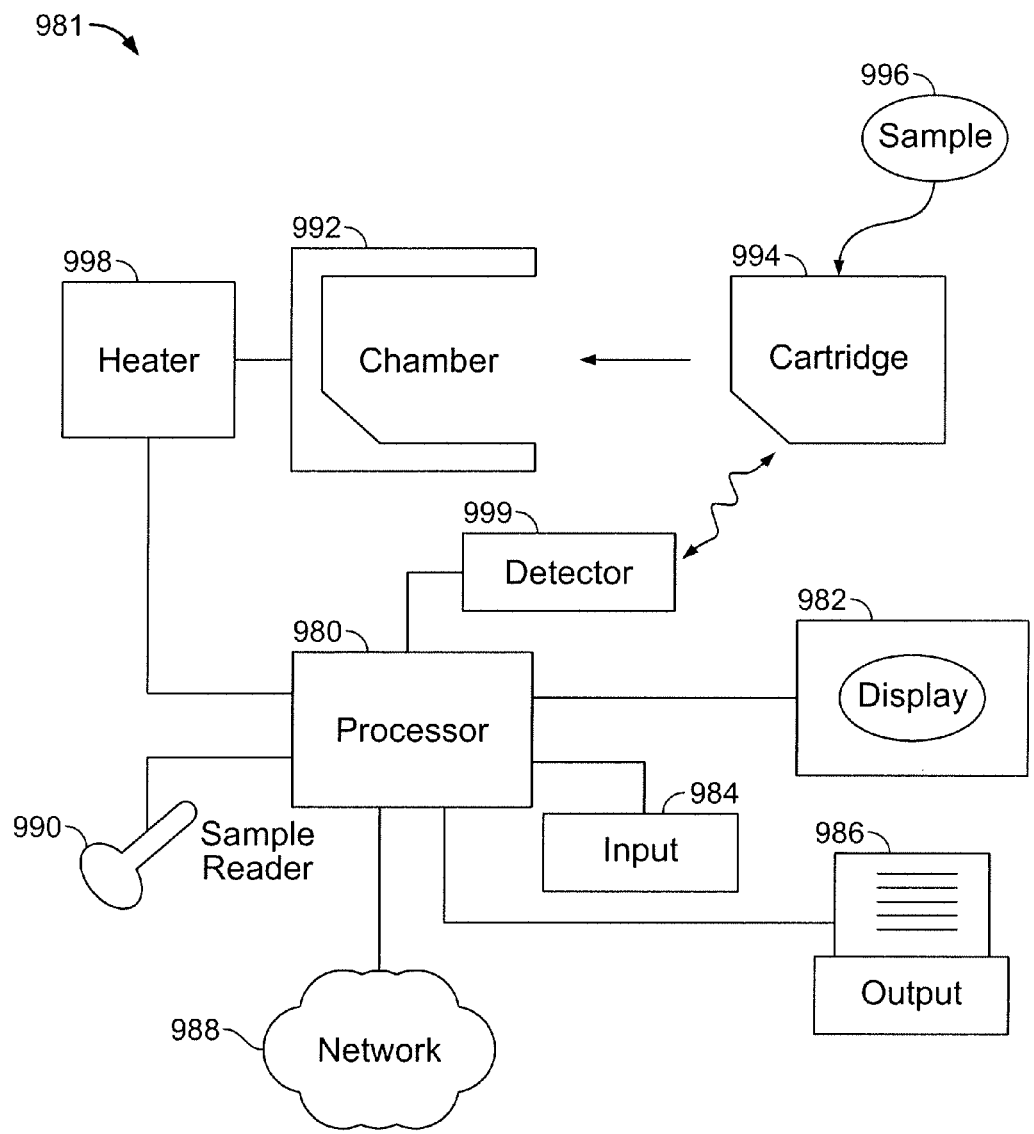
FIG. 3 shows a schematic diagram of an apparatus.

A schematic overview of a system 981 for carrying out analyses described herein is shown in FIG. 3. The geometric arrangement of the components of system 981 shown in FIG. 3, as well as their respective connectivities, is exemplary and not intended to be limiting.

A processor 980, such as a microprocessor, is configured to control functions of various components of the system as shown, and is thereby in communication with each such component. In particular, processor 980 is configured to receive data about a sample to be analyzed, e.g., from a sample reader 990, which may be a barcode reader, an optical character reader, or an RFID scanner (radio frequency tag reader). For example, the sample identifier can be a handheld bar code reader. Processor 980 can be configured to accept user instructions from an input 984, where such instructions may include instructions to start analyzing the sample, and choices of operating conditions.

Processor 980 can also be configured to communicate with an optional display 982, so that, for example, information including but not limited to the current status of the system, progress of PCR thermocycling, and any warning message in case of malfunction of either system or cartridge, as well as results of analysis, are transmitted to the display. Additionally, processor 980 may transmit one or more questions to be displayed on display 982 that prompt a user to provide input in response thereto. Thus, in certain embodiments, input 984 and display 982 are integrated with one another.

Processor 980 can be optionally further configured to transmit results of an analysis to an output device such as a printer, a visual display, or a speaker, or a combination thereof, the transmission being either directly through a directly dedicated printer cable, or wirelessly, or via a network connection.

Processor 980 is still further optionally connected via a communication interface such as a network interface to a computer network 988. The communication interface can be one or more interfaces selected from the group consisting of: a serial connection, a parallel connection, a wireless network connection and a wired network connection such as an ethernet, firewire, cable connection, or one using USB connectivity. Thereby, when the system is suitably addressed on the network, a remote user may access the processor and transmit instructions, input data, or retrieve data, such as may be stored in a memory (not shown) associated with the processor, or on some other computer-readable medium that is in communication with the processor. The computer network connection may also permit extraction of data to a remote location, such as a personal computer, personal digital assistant, or network storage device such as computer server or disk farm. The apparatus may further be configured to permit a user to e-mail results of an analysis directly to some other party, such as a healthcare provider, or a diagnostic facility, or a patient.

Although not shown in FIG. 3, in various embodiments, input 984 can include one or more input devices selected from the group consisting of: a keyboard, a touch-sensitive surface, a microphone, a track-pad, and a mouse. A suitable input device may further comprise a reader of formatted electronic media, such as, but not limited to, a flash memory card, memory stick, USB-stick, CD, or floppy diskette. An input device may further comprise a security feature such as a fingerprint reader, retinal scanner, magnetic strip reader, or bar-code reader, for ensuring that a user of the system is in fact authorized to do so, according to, for example, pre-loaded identifying characteristics of authorized users. An input device may additionally—and simultaneously—function as an output device for writing data in connection with sample analysis. For example, if an input device is a reader of formatted electronic media, it may also be a writer of such media. Data that may be written to such media by such a device includes, but is not limited to, environmental information, such as temperature or humidity, pertaining to an analysis, as well as a diagnostic result, and identifying data for the sample in question.

Additionally, in various embodiments, the apparatus can further comprise a data storage medium configured to receive data from one or more of the processor, an input device, and a communication interface, the data storage medium being one or more media selected from the group consisting of: a hard disk drive, an optical disk drive, or one or more removable storage media such as a CD-R, CD-RW, USB-drive, and a flash card.

Processor 980 is further configured to control various aspects of sample diagnosis, as follows in overview, and as further described in detail herein. The system is configured to operate in conjunction with a complementary cartridge 994, such as a microfluidic cartridge. The cartridge is itself configured, as further described herein, to receive one or more samples 996 containing one or more polynucleotides in a form suitable for amplification and diagnostic analysis. The cartridge has dedicated regions within which amplification, such as by PCR, of the polynucleotides is carried out when the cartridge is situated in the apparatus.

The microfluidic cartridge is received by a receiving bay 992 configured to selectively receive the cartridge. For example, the receiving bay and the microfluidic cartridge can be complementary in shape so that the microfluidic cartridge is selectively received in, e.g., a single orientation. The microfluidic cartridge can have a registration member that fits into a complementary feature of the receiving bay. The registration member can be, for example, a cut-out on an edge of the cartridge, such as a corner that is cut-off, or one or more notches that are made on one or more of the sides. By selectively receiving the cartridge, the receiving bay can help a user to place the cartridge so that the apparatus can properly operate on the cartridge. The receiving bay can also be configured so that various components of the apparatus that can operate on the microfluidic cartridge (heat sources, detectors, force members, and the like) are positioned to properly operate on the microfluidic cartridge. In some embodiments, the apparatus can further include a sensor coupled to the processor, the sensor configured to sense whether the microfluidic cartridge is selectively received.

The receiving bay is in communication with a heater unit 998 that itself is controlled by processor 980 in such a way that specific regions of the cartridge, such as individual sample lanes, are independently and selectively heated at specific times during amplification and analysis. The processor can be configured to control application of heat to the individual sample lanes, separately, in all simultaneously, or in groups simultaneously.

The heat source can be, for example, a contact heat source such as a resistive heater or a network of resistive heaters, or a Peltier device, and the like. The contact heat source can be configured to be in direct physical contact with one or more distinct locations of a microfluidic cartridge received in the receiving bay. In various embodiments, each contact source heater can be configured to heat a distinct location having an average diameter in 2 dimensions from about 1 millimeter (mm) to about 15 mm (typically about 1 mm to about 10 mm), or a distinct location having a surface area of between about 1 $mm^2$ about 225 $mm^2$ (typically between about 1 $mm^2$ and about 100 $mm^2$, or in some embodiments between about 5 $mm^2$ and about 50 $mm^2$).

In various embodiments, the heat source can be situated in an assembly that is removable from the apparatus, for example, to permit cleaning or to replace the heater configuration.

In various embodiments, the apparatus can include a compliant layer at the contact heat source configured to thermally couple the contact heat source with at least a portion of a microfluidic cartridge received in the receiving bay. The compliant layer at can have a thickness of between about 0.05 and about 2 millimeters and a Shore hardness of between about 25 and about 100.

In various embodiments, the apparatus can further include one or more force members (not shown in FIG. 3) configured to apply force to thermally couple the at least one heat source at least a portion of a microfluidic cartridge received in the receiving bay.

In various embodiments, the one or more force members are configured to apply force to a plurality of locations in the microfluidic cartridge. The force applied by the one or more force members can result in an average pressure at an interface between a portion of the receiving bay and a portion of the microfluidic cartridge of between about 5 kilopascals and about 50 kilopascals, for example, the average pressure can be at least about 7 kilopascals, and still more preferably at least about 14 kilopascals. At least one force member can be manually operated. At least one force member can be mechanically coupled to a lid at the receiving bay, whereby operation of the lid operates the force member. The application of force is important to ensure consistent thermal contact between the heater wafer and the PCR reactor and microvalves in the microfluidic cartridge.

In various embodiments, the apparatus can further include a lid at the receiving bay, the lid being operable to at least partially exclude ambient light from the receiving bay. The lid can be, for example, a sliding lid. The lid can include the optical detector. A major face of the lid at the optical detector or at the receiving bay can vary from planarity by less than about 100 micrometers, for example, less than about 25 micrometers. The lid can be configured to be removable from the apparatus. The lid can include a latching member that ensures that the lid is securely closed before amplification reactions are applied to the samples in the cartridge.

The processor is also configured to receive signals from and control a detector 999 configured to detect a polynucleotide in a sample in one or more of the individual sample lanes, separately or simultaneously. The processor thereby provides an indication of a diagnosis from the cartridge 994. Diagnosis can be predicated on the presence or absence of a specific polynucleotide in a particular sample. The diagnosis can be transmitted to the output device 986 and/or the display 982, as described hereinabove.

The detector can be, for example, an optical detector that includes a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof. Alternatively, for example, the optical detector can include a bandpass-filtered diode that selectively emits light in the absorption band of the fluorescent dye and a bandpass filtered photodiode that selectively detects light in the emission band of the fluorescent dye; or for example, the optical detector can be configured to independently detect a plurality of fluorescent dyes having different fluorescent emission spectra, wherein each fluorescent dye corresponds to a fluorescent polynucleotide probe or a fragment thereof; or for example, the optical detector can be configured to independently detect a plurality of fluorescent dyes at a plurality of different locations on a microfluidic cartridge, wherein each fluorescent dye corresponds to a fluorescent polynucleotide probe or a fragment thereof in a different sample.

A suitable processor 980 can be designed and manufactured according to, respectively, design principles and semiconductor processing methods known in the art.

The system in FIG. 3 is configured so that a cartridge with capacity to receive multiple samples can be acted upon by the system to analyze multiple samples—or subsets thereof—simultaneously, or to analyze the samples consecutively. It is also consistent that additional samples can be added to a cartridge, while previously added samples are being amplified and analyzed.

The system shown in outline in FIG. 3, as with other exemplary embodiments described herein, is advantageous at least because it does not require locations within the system suitably configured for storage of reagents. Neither does the system, or other exemplary embodiments herein, require inlet or outlet ports that are configured to receive reagents from, e.g., externally stored containers such as bottles, canisters, or reservoirs. Therefore, the system in FIG. 3 is self-contained and operates in conjunction with a microfluidic cartridge, wherein the cartridge has locations within it configured to receive mixtures of sample and PCR reagents.

The system of FIG. 3 may be configured to carry out operation in a single location, such as a laboratory setting, or may be portable so that it can accompany, e.g., a physician, or other healthcare professional, who may visit patients at different locations. The system is typically provided with a power-cord so that it can accept AC power from a mains supply or generator. An optional transformer (not shown) built into the system, or situated externally between a power socket and the system, transforms AC input power into a DC output for use by the system. The system may also be configured to operate by using one or more batteries and therefore is also typically equipped with a battery recharging system, and various warning devices that alert a user if battery power is becoming too low to reliably initiate or complete a diagnostic analysis.

The system of FIG. 3 may further be configured, for multiplexed cartridge analysis. In one such configuration, multiple instances of a system, as outlined in FIG. 3, are operated in conjunction with one another to accept and to process multiple cartridges, where each cartridge has been loaded with a different sample. Each component shown in FIG. 3 may therefore be present as many times as there are cartridges, though the various components may be configured in a common housing.

In still another configuration, a system is configured to accept and to process multiple cartridges, but one or more components in FIG. 3 is common to multiple cartridges. For example, a single device may be configured with multiple cartridge receiving bays, but a common processor and user interface suitably configured to permit concurrent, consecutive, or simultaneous, control of the various cartridges. In such an embodiment a single detector, for example, can scan across all of the multiple cartridges. It is further possible that such an embodiment, also utilizes a single sample reader, and a single output device.

In still another configuration, a system as shown in FIG. 3 is configured to accept a single cartridge, but wherein the single cartridge is configured to process more than 1, for example, 2, 3, 4, 5, or 6, samples in parallel, and independently of one another.

It is further consistent with the present technology that a cartridge can be tagged, e.g., with a molecular bar-code indicative of one or more of the samples, to facilitate sample tracking, and to minimize risk of sample mix-up. Methods for such tagging are described elsewhere, e.g., in U.S. patent application publication Ser. No. 10/360,854, incorporated herein by reference.

In various embodiments, the apparatus can further include an analysis port. The analysis port can be configured to allow an external sample analyzer to analyze a sample in the microfluidic cartridge; for example, the analysis port can be a hole or window in the apparatus which can accept an optical detection probe that can analyze a sample in situ in the microfluidic cartridge. In some embodiments, the analysis port can be configured to direct a sample from the microfluidic cartridge to an external sample analyzer; for example, the analysis port can include a conduit in fluid communication with the microfluidic cartridge that direct a liquid sample to a chromatography apparatus, an optical spectrometer, a mass spectrometer, or the like.

Apparatus 100 may optionally comprise one or more stabilizing feet that cause the body of the device to be elevated above a surface on which system 100 is disposed, thereby permitting ventilation underneath system 100, and also providing a user with an improved ability to lift system 100. There may be 2, 3, 4, 5, or 6, or more feet, depending upon the size of system 100. Such feet are preferably made of rubber, or plastic, or metal, and in some embodiments may elevate the body of system 100 by from about 2 to about 10 mm above a surface on which it is situated. The stabilizing function can also be provided by one or more runners that run along one or more edges—or are inwardly displaced from one or more edges—of the underside of the apparatus. Such runners can also be used in conjunction with one or more feet. In another embodiment, a turntable situated on the underside permits the apparatus to be rotated in a horizontal or near-horizontal plane when positioned on, e.g., a benchtop, to facilitate access from a number of angles by a user.

Figure 4:
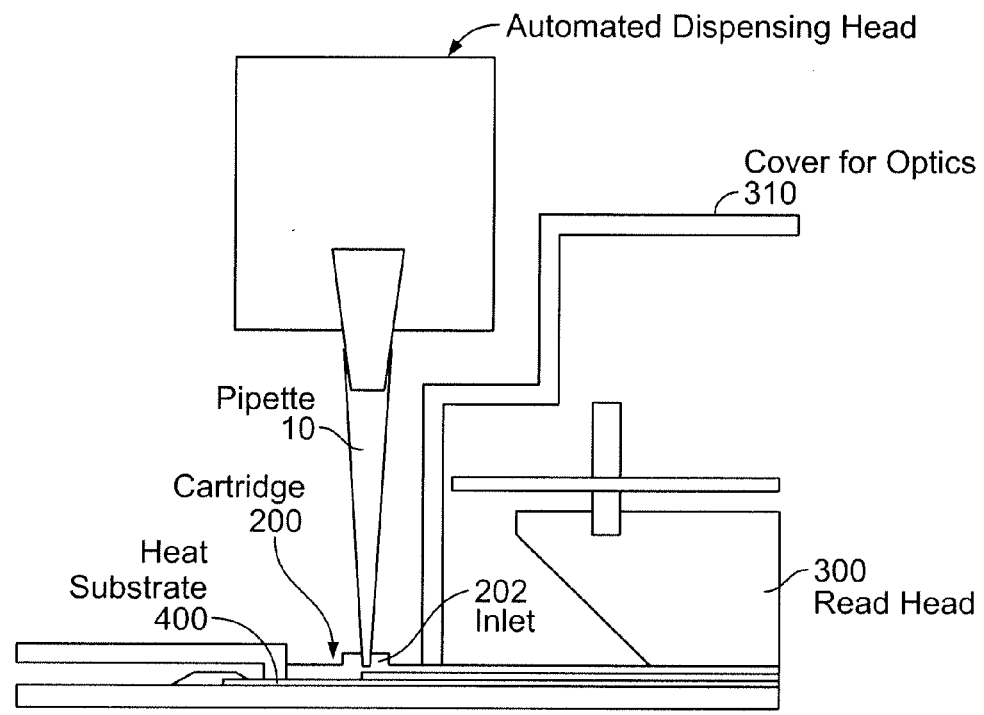
FIG. 4 shows a cross-section of a pipetting head and a cartridge in position in a microfluidic apparatus.

FIG. 4 shows a schematic cross-sectional view of a part of an apparatus as described herein, showing input of sample into a cartridge 200 via a pipette 10 (such as a disposable pipette) and an inlet 202. Inlet 202 is preferably configured to receive a pipette or the bottom end of a PCR tube and thereby accept sample for analysis with minimum waste, and with minimum introduction of air. Cartridge 200 is disposed on top of and in contact with a heater substrate 400. Read head 300 is positioned above cartridge 200 and a cover for optics 310 restricts the amount of ambient light that can be detected by the read head.

Figure 5:
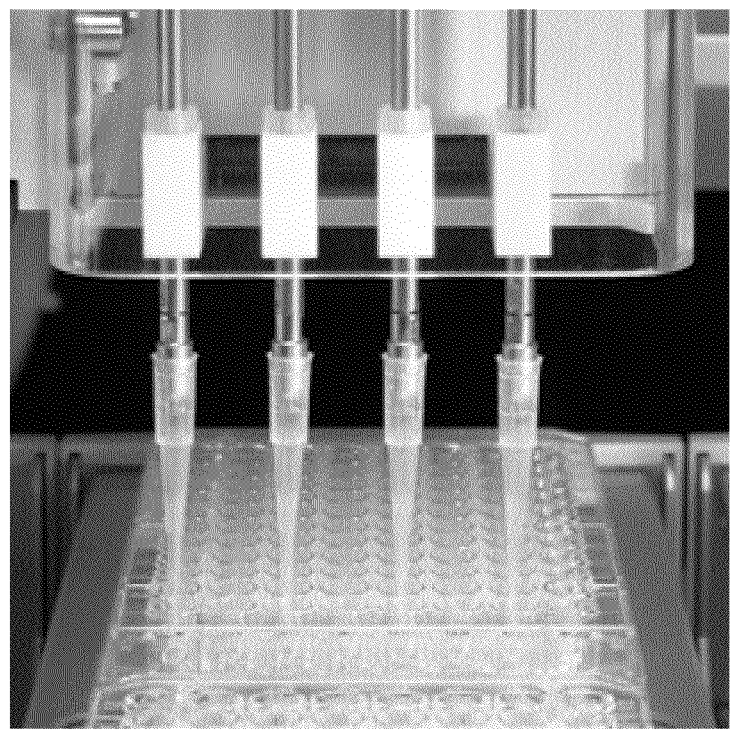
FIG. 5 shows introduction of a PCR-ready sample into a cartridge, situated in an instrument.

FIG. 5 shows an example of 4-pipette head used for attaching disposable pipette tips, prior to dispensing PCR-ready sample into a cartridge.

Exemplary Systems

Figure 6A:
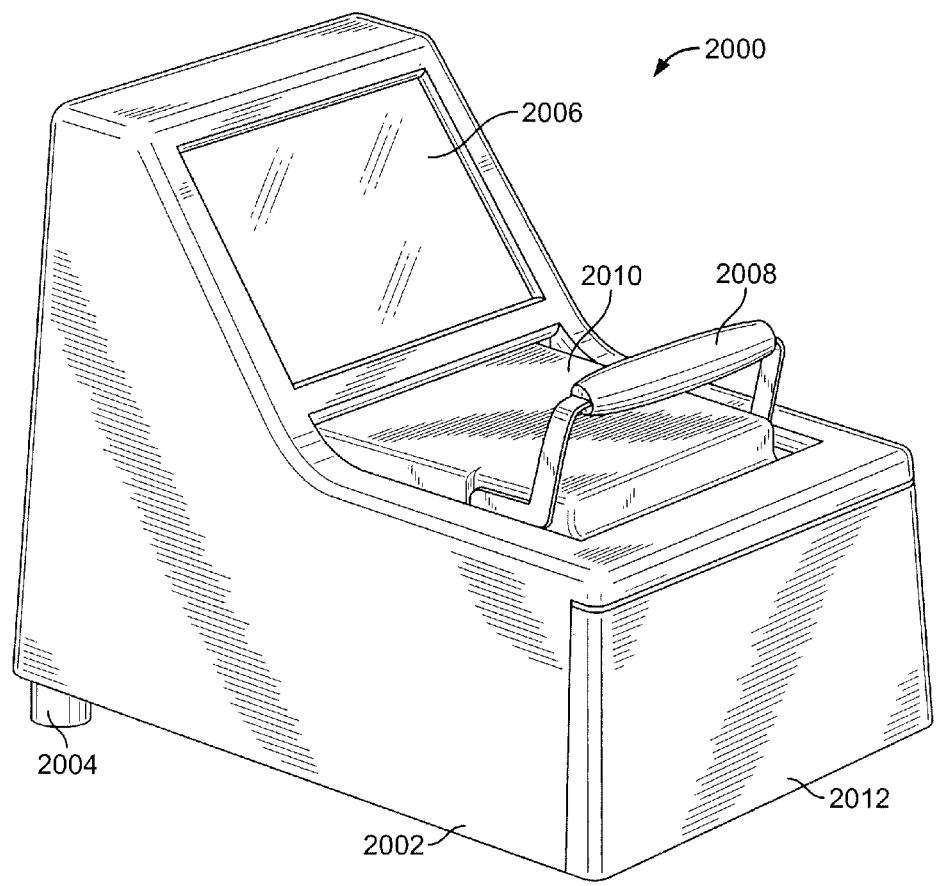

FIGS. 6A-6E show exterior perspective views of various configurations of an exemplary system, as further described herein. FIG. 6A shows a perspective view of a system 2000 for receiving microfluidic cartridge (not shown), and for causing and controlling various processing operations to be performed a sample introduced into the cartridge. The elements of system 2000 are not limited to those explicitly shown. For example, although not shown, system 2000 may be connected to a hand-held bar-code reader, as further described herein.

System 2000 comprises a housing 2002, which can-be made of metal, or a hardened plastic. The form of the housing shown in FIG. 6A embodies stylistic as well as functional features. Other embodiments of the technology may appear somewhat differently, in their arrangement of the components, as well as their overall appearance, in terms of smoothness of lines, and of exterior finish, and texture. System 2000 further comprises one or more stabilizing members 2004. Shown in FIG. 6A is a stabilizing foot, of which several are normally present, located at various regions of the underside of system 2000 so as to provide balance and support. For example, there may be three, four, five, six, or eight such stabilizing feet. The feet may be moulded into and made of the same material as housing 2002, or may be made of one or more separate materials and attached to the underside of system 2000. For example, the feet may comprise a rubber that makes it hard for system 2000 to slip on a surface on which it is situated, and also protects the surface from scratches. The stabilizing member of members may take other forms than feet, for example, rails, runners, or one or more pads.

System 2000 further comprises a display 2006, which may be a liquid crystal display, such as active matrix, an OLED, or some other suitable form. It may present images and other information in color or in black and white. Display 2006 may also be a touch-sensitive display and therefore may be configured to accept input from a user in response to various displayed prompts. Display 2006 may have an anti-reflective coating on it to reduce glare and reflections from overhead lights in an laboratory setting. Display 2006 may also be illuminated from, e.g., a back-light, to facilitate easier viewing in a dark laboratory.

Figure 6B:
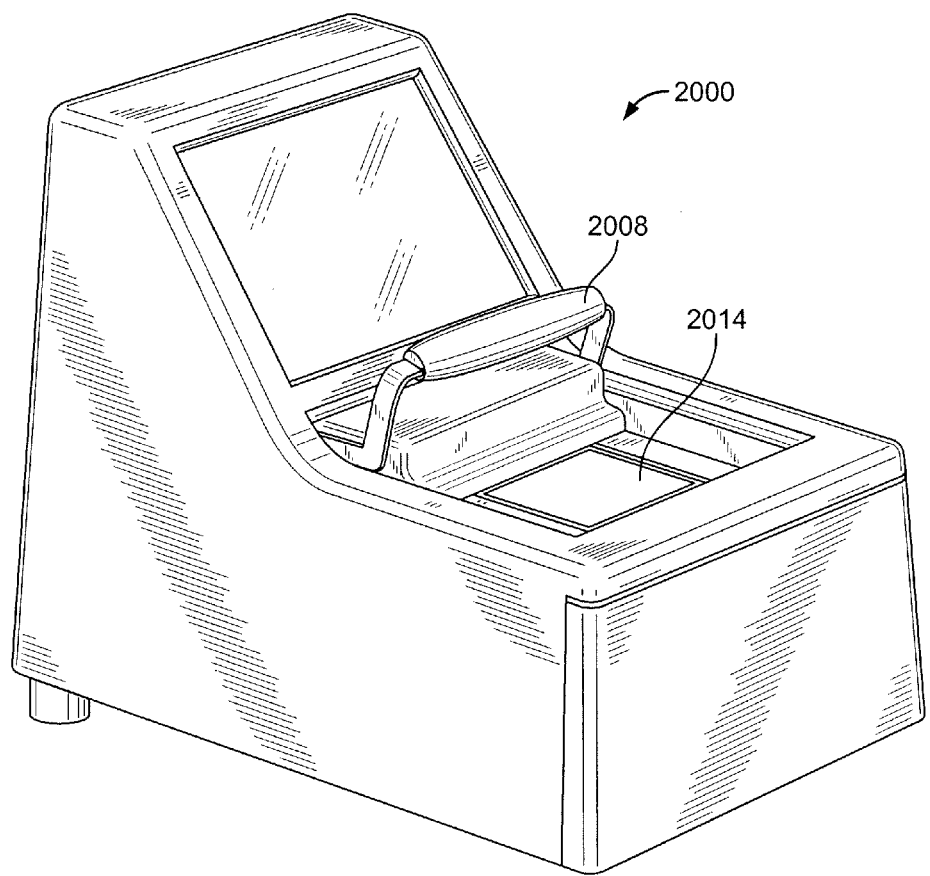

System 2000, as shown in FIG. 6A, also comprises a moveable lid 2010, having a handle 2008. The lid 2010 can slide back and forward. In FIG. 6A, the lid is in a forward position, whereby it is "closed". In FIG. 6B, the lid is shown in a back position, wherein the lid is "open" and reveals a receiving bay 2014 that is configured to receive a microfluidic cartridge. Of course, as one of ordinary skill in the art would appreciate, the technology described herein is not limited to a lid that slides, or one that slides back and forward. Side to side movement is also possible, as is a configuration where the lid is "open" when positioned forward in the device. It is also possible that the lid is a hinged lid, or one that is totally removable.

Figure 6C:
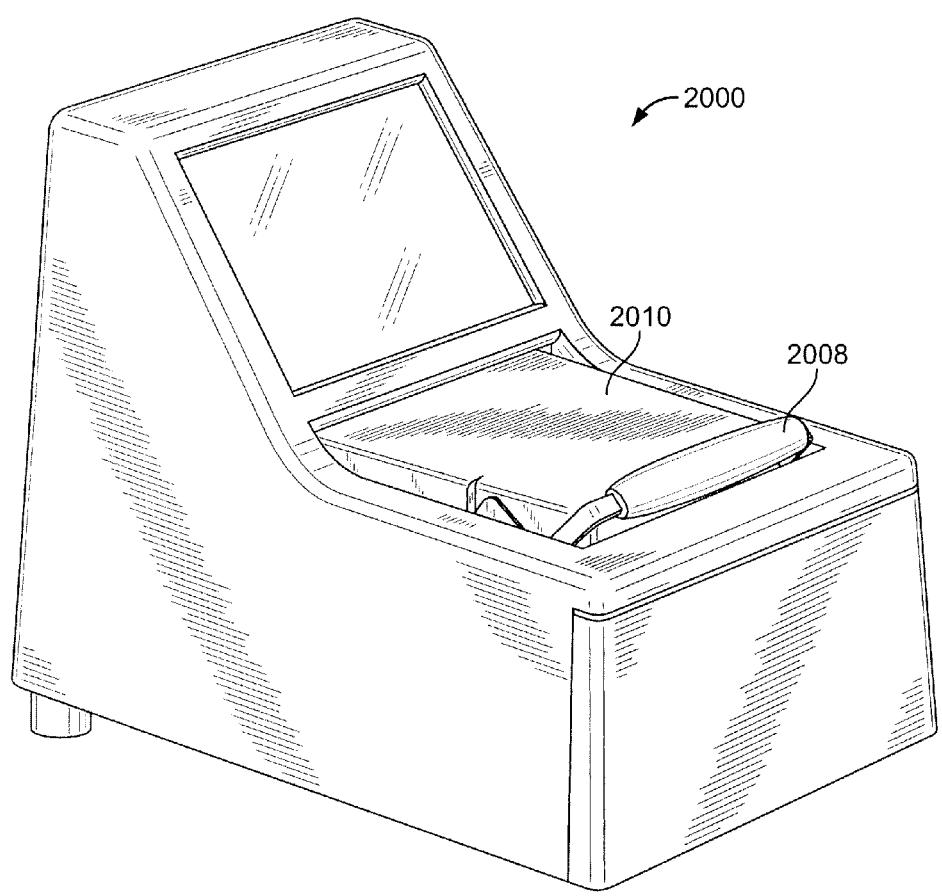

Handle 2008 performs a role of permitting a user to move lid 2010 form one position to another, and also performs a role of causing pressure to be forced down on the lid, when in a closed position, so that pressure can be applied to a cartridge in the receiving bay 2014. In FIG. 6C, handle 2008 is shown in a depressed position, wherein force is thereby applied to lid 2014, and thus pressure is applied to a cartridge received in the receiving bay beneath the lid.

In one embodiment, the handle and lid assembly are also fitted with a mechanical sensor that does not permit the handle to be depressed when there is no cartridge in the receiving bay. In another embodiment, the handle and lid assembly are fitted with a mechanical latch that does not permit the handle to be raised when an analysis is in progress.

A further configuration of system 2000 is shown in FIG. 6D, wherein a door 2012 is in an open position. Door 2012 is shown in a closed position in FIGS. 6A-C. The door is an optional component that permits a user to access a heater module 2020, and also a computer-readable medium input tray 2022. System 2000 can function without a door that covers heater module 2020 and medium input 2022, but such a door has convenience attached to it. Although the door 2012 is shown hinged at the bottom, it may also be hinged at one of its sides, or at its upper edge. Door 2012 may alternatively be a removable cover, instead of being hinged. Door 2012, may also be situated at the rear, or side of system 2000 for example, if access to the heater module and/or computer readable medium input is desired on a different face of the system. It is also consistent with the system herein that the heater module, and the computer readable medium input are accessed by separate doors on the same or different sides of the device, and wherein such separate doors may be independently hinged or removable.

Heater module 2020 is preferably removable, and is further described hereinbelow.

Computer readable medium input 2022 may accept one or more of a variety of media. Shown in FIG. 2D is an exemplary form of input 2022, a CD-Rom tray for accepting a CD, DVD, or mini-CD, or mini-DVD, in any of the commonly used readable, read-writable, and writable formats. Also consistent with the description herein is an input that can accept another form of medium, such as a floppy disc, flash memory such as memory stick, compact flash, smart data-card, or secure-data card, a pen-drive, portable USB-drive, zip-disk, and others. Such an input can also be configured to accept several different forms of media. Such an input 2022 is in communication with a processor (as described in connection with FIG. 3, though not shown in FIGS. 6A-E), that can read data from a computer-readable medium when properly inserted into the input.

Figure 6E:
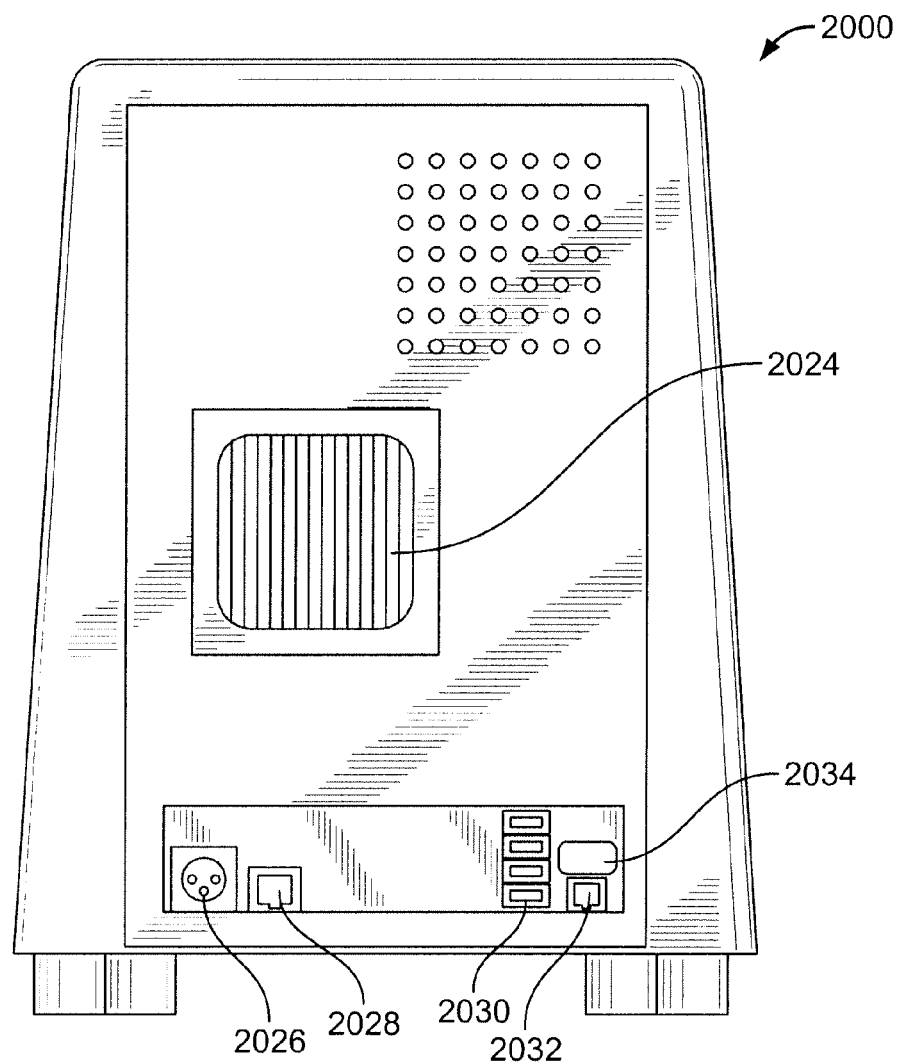

FIG. 6E shows a plan view of a rear of system 2000. Shown are an air vent 2024, or letting surplus heat escape during an analysis. Typically, on the inside of system 2000, and by air vent 2024 and not shown in FIG. 6E, is a fan. Other ports shown in FIG. 6E are as follows: a power socket 2026 for accepting a power cord that will connect system 2000 to a supply of electricity; an ethernet connection 2028 for linking system 2000 to a computer network such as a local area network; an phone-jack connection 2032 for linking system 2000 to a communication network such as a telephone network; one or more USB ports 2030, for connecting system 2000 to one or more peripheral devices such as a printer, or a computer hard drive; an infra-red port for communicating with, e.g., a remote controller (not shown), to permit a user to control the system without using a touch-screen interface. For example, a user could remotely issue scheduling commands to system 2000 to cause it to start an analysis at a specific time in the future.

Features shown on the rear of system 2000 may be arranged in any different manner, depending upon an internal configuration of various components. Additionally, features shown as being on the rear of system 2000, may be optionally presented on another face of system 2000, depending on design preference. Shown in FIG. 6E are exemplary connections. It would be understood that various other features, including inputs, outputs, sockets, and connections, may be present on the rear face of system 2000, though not shown, or on other faces of system 2000.

Figure 7:
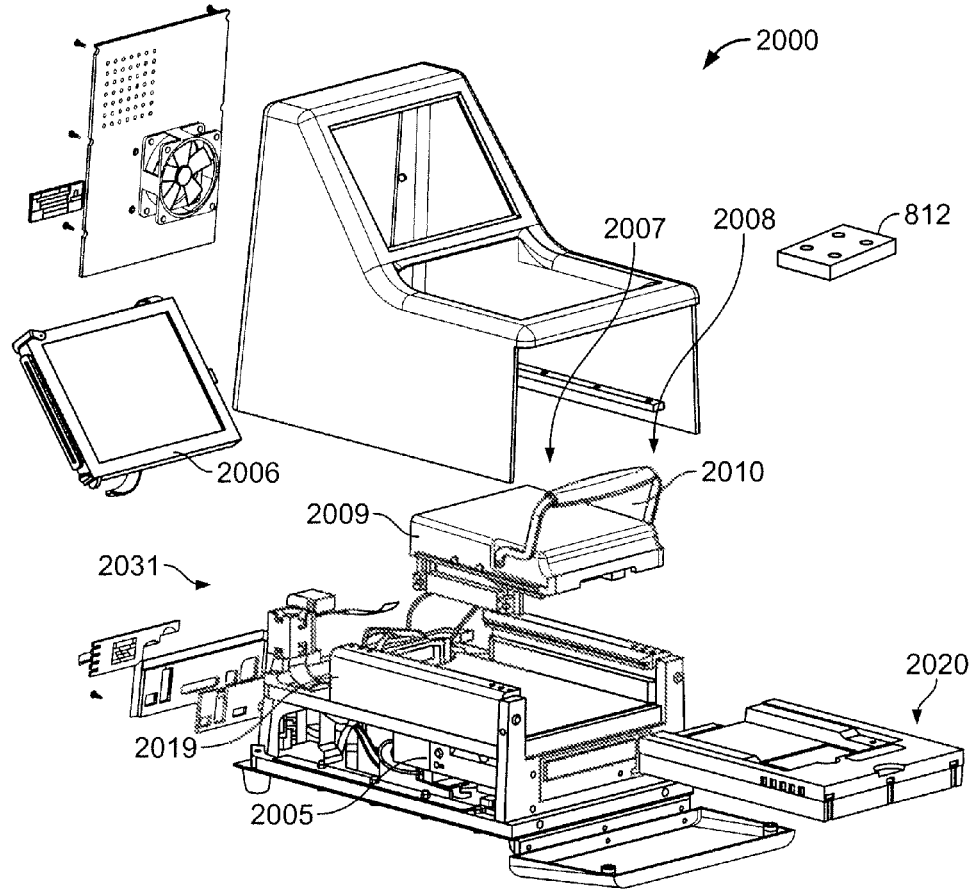
FIG. 7 shows an exploded view of an apparatus.

An exploded view of an exemplary embodiment of the apparatus is shown in FIG. 7, particularly showing internal features of apparatus 2000. Apparatus 2000 can comprise a computer readable medium configured with hardware/firmware that can be employed to drive and monitor the operations on a cartridge used therewith, as well as software to interpret, communicate and store the results of a diagnostic test performed on a sample processed in the cartridge. Referring to FIG. 7, typical components of the apparatus 2000 are shown and include, for example, control electronics 2005, removable heater/sensor module 2020, detector 2009 such as a fluorescent detection module, display screen or optionally combined display and user interface 2006 (e.g., a medical grade touch sensitive liquid crystal display (LCD)). In some embodiments, lid 2010, detector 2009, and handle 2008 can be collectively referred to as slider module 2007. Additional components of apparatus 2000 may include one or more mechanical fixtures such as frame 2019 to hold the various modules (e.g., the heater/sensor module 2020, and/or the slider module 2007) in alignment, and for providing structural rigidity. Detector module 2009 can be placed in rails to facilitate opening and placement of cartridge 2060 in the apparatus 2000, and to facilitate alignment of the optics upon closing. Heater/sensor module 2020 can be also placed on rails for easy removal and insertion of the assembly.

Embodiments of apparatus 2000 also include software (e.g., for interfacing with users, conducting analysis and/or analyzing test results), firmware (e.g., for controlling the hardware during tests on the cartridge 812), and one or more peripheral communication interfaces shown collectively as 2031 for peripherals (e.g., communication ports such as USB/Serial/Ethernet to connect to storage such as compact disc or hard disk, to connect input devices such as a bar code reader and/or a keyboard, to connect to other computers or storage via a network, and the like).

Figure 8:
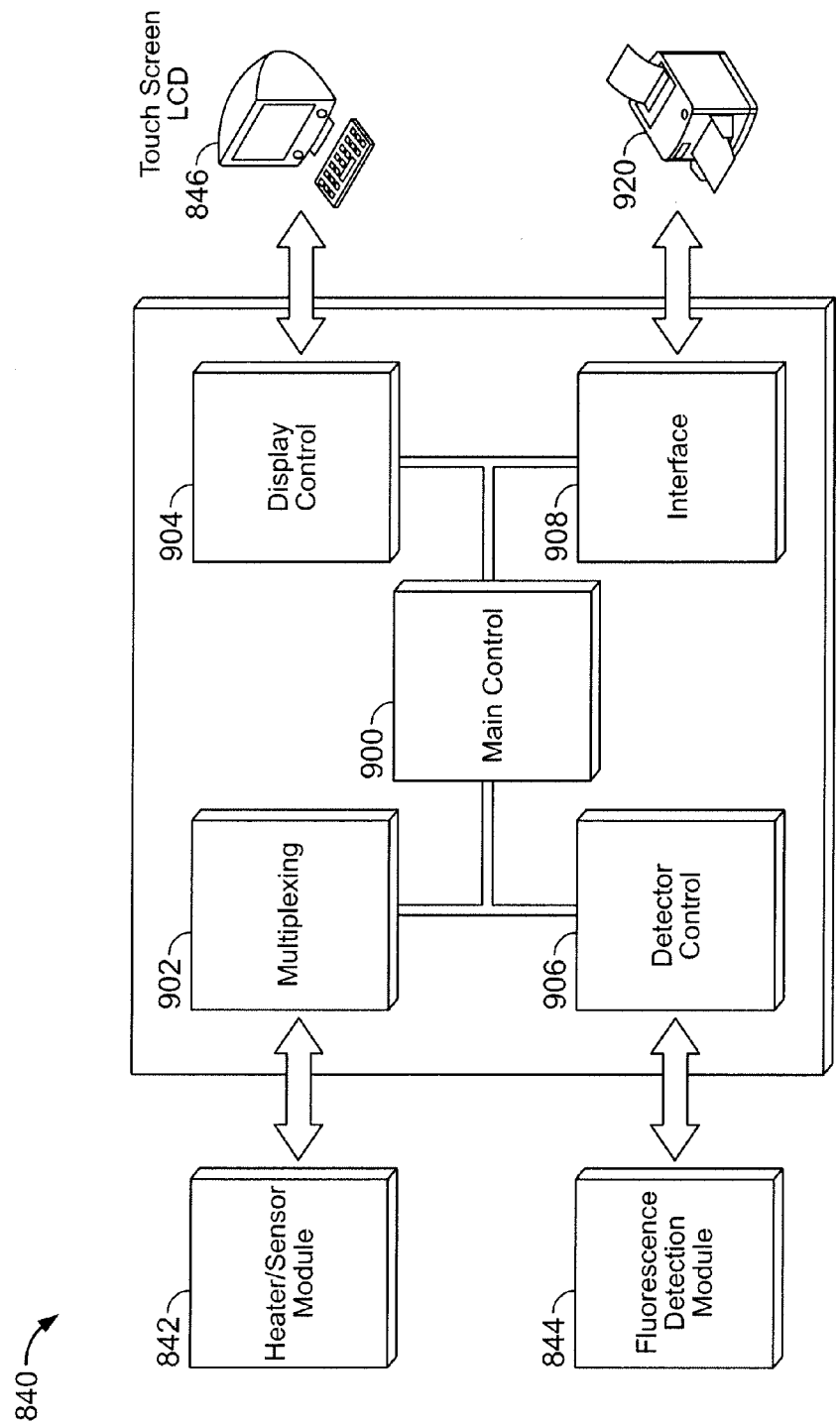
FIG. 8 shows a block diagram of control circuitry.

Control electronics 840, shown schematically in the block diagram in FIG. 8, can include one or more functions in various embodiments, for example for, main control 900, multiplexing 902, display control 904, detector control 906, and the like. The main control function may serve as the hub of control electronics 840 in apparatus 2000 and can manage communication and control of the various electronic functions. The main control function can also support electrical and communications interface 908 with a user or an output device such as a printer 920, as well as optional diagnostic and safety functions. In conjunction with main control function 900, multiplexer function 902 can control sensor data 914 and output current 916 to help control heater/sensor module 2020. The display control function 904 can control output to and, if applicable, interpret input from touch screen LCD 846, which can thereby provide a graphical interface to the user in certain embodiments. The detector function 906 can be implemented in control electronics 840 using typical control and processing circuitry to collect, digitize, filter, and/or transmit the data from a detector 2009 such as one or more fluorescence detection modules.

Microfluidic Cartridge

The present technology comprises a microfluidic cartridge that is configured to carry out an amplification, such as by PCR, of one or more polynucleotides from one or more samples. It is to be understood that, unless specifically made clear to the contrary, where the term PCR is used herein, any variant of PCR including but not limited to real-time and quantitative, and any other form of polynucleotide amplification is intended to be encompassed. The microfluidic cartridge need not be self-contained and can be designed so that it receives thermal energy from one or more heating elements present in an external apparatus with which the cartridge is in thermal communication. An exemplary such apparatus is further described herein; additional embodiments of such a system are found in U.S. patent application Ser. No. 11/940,310, entitled "Microfluidic Cartridge and Method of Making Same", and filed on even date herewith, the specification of which is incorporated herein by reference.

By cartridge is meant a unit that may be disposable, or reusable in whole or in part, and that is configured to be used in conjunction with some other apparatus that has been suitably and complementarily configured to receive and operate on (such as deliver energy to) the cartridge.

By microfluidic, as used herein, is meant that volumes of sample, and/or reagent, and/or amplified polynucleotide are from about 0.1 µl to about 999 µl, such as from 1-100 µl or from 2-25 µl. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide. Certain embodiments herein can also function with nanoliter volumes (in the range of 10-500 nanoliters, such as 100 nanoliters).

One aspect of the present technology relates to a microfluidic cartridge having two or more sample lanes arranged so that analyses can be carried out in two or more of the lanes in parallel, for example simultaneously, and wherein each lane is independently associated with a given sample.

A sample lane is an independently controllable set of elements by which a sample can be analyzed, according to methods described herein as well as others known in the art. A sample lane comprises at least a sample inlet, and a microfluidic network having one or more microfluidic components, as further described herein.

In various embodiments, a sample lane can include a sample inlet port or valve, and a microfluidic network that comprises, in fluidic communication one or more components selected from the group consisting of: at least one thermally actuated valve, a bubble removal vent, at least one thermally actuated pump, a gate, mixing channel, positioning element, microreactor, a downstream thermally actuated valve, and a PCR reaction chamber. The sample inlet valve can be configured to accept a sample at a pressure differential compared to ambient pressure of between about 70 and 100 kilopascals.

The cartridge can therefore include a plurality of microfluidic networks, each network having various components, and each network configured to carry out PCR on a sample in which the presence or absence of one or more polynucleotides is to be determined.

A multi-lane cartridge is configured to accept a number of samples in series or in parallel, simultaneously or consecutively, in particular embodiments 12 samples, wherein the samples include at least a first sample and a second sample, wherein the first sample and the second sample each contain one or more polynucleotides in a form suitable for amplification. The polynucleotides in question may be the same as, or different from one another, in different samples and hence in different lanes of the cartridge. The cartridge typically processes each sample by increasing the concentration of a polynucleotide to be determined and/or by reducing the concentration of inhibitors relative to the concentration of polynucleotide to be determined.

The multi-lane cartridge comprises at least a first sample lane having a first microfluidic network and a second lane having a second microfluidic network, wherein each of the first microfluidic network and the second microfluidic network is as elsewhere described herein, and wherein the first microfluidic network is configured to amplify polynucleotides in the first sample, and wherein the second microfluidic network is configured to amplify polynucleotides in the second sample.

In various embodiments, the microfluidic network can be configured to couple heat from an external heat source to a sample mixture comprising PCR reagent and neutralized polynucleotide sample under thermal cycling conditions suitable for creating PCR amplicons from the neutralized polynucleotide sample.

At least the external heat source may operate under control of a computer processor, configured to execute computer readable instructions for operating one or more components of each sample lane, independently of one another, and for receiving signals from a detector that measures fluorescence from one or more of the PCR reaction chambers.

Figure 9:
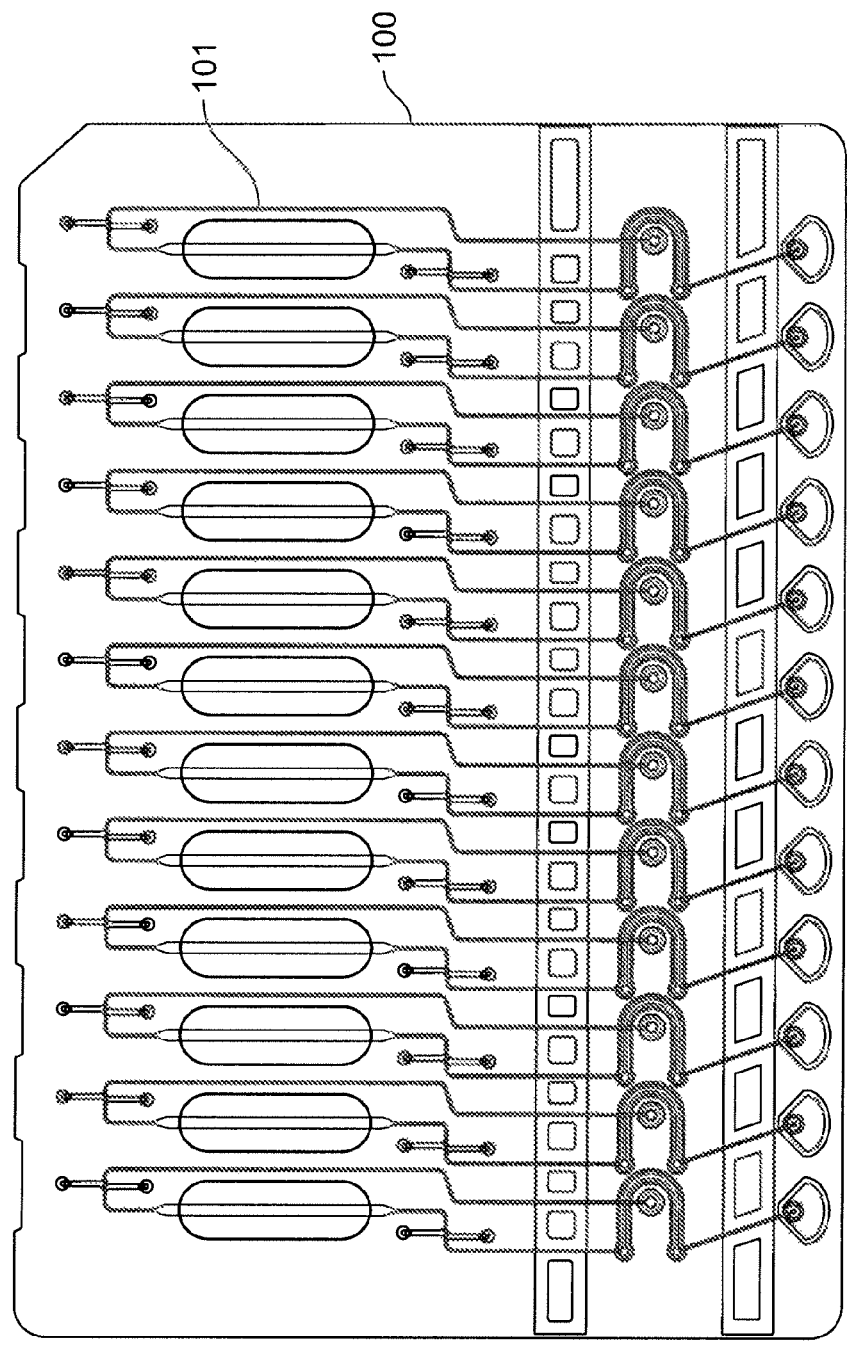
FIG. 9 shows a plan view of an exemplary multi-lane microfluidic cartridge.

For example, FIG. 9 shows a plan view of a microfluidic cartridge 100 containing twelve independent sample lanes 101 capable of simultaneous or successive processing. The microfluidic network in each lane is typically configured to carry out amplification, such as by PCR, on a PCR-ready sample, such as one containing nucleic acid extracted from a sample using other methods as further described herein. A PCR-ready sample is thus typically a mixture comprising the PCR reagents and the neutralized polynucleotide sample, suitable for subjecting to thermal cycling conditions that create PCR amplicons from the neutralized polynucleotide sample. For example, a PCR-ready sample can include a PCR reagent mixture comprising a polymerase enzyme, a positive control plasmid, a fluorogenic hybridization probe selective for at least a portion of the plasmid and a plurality of nucleotides, and at least one probe that is selective for a polynucleotide sequence. Exemplary probes are further described herein. Typically, the microfluidic network is configured to couple heat from an external heat source with the mixture comprising the PCR reagent and the neutralized polynucleotide sample under thermal cycling conditions suitable for creating PCR amplicons from the neutralized polynucleotide sample.

In various embodiments, the PCR reagent mixture can include a positive control plasmid and a plasmid fluorogenic hybridization probe selective for at least a portion of the plasmid, and the microfluidic cartridge can be configured to allow independent optical detection of the fluorogenic hybridization probe and the plasmid fluorogenic hybridization probe.

In various embodiments, the microfluidic cartridge can accommodate a negative control polynucleotide, wherein the microfluidic network can be configured to independently carry out PCR on each of a neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide. Each lane of a multi-lane cartridge as described herein can perform two reactions when used in conjunction with two fluorescence detection systems per lane. A variety of combinations of reactions can be performed in the cartridge, such as two sample reactions in one lane, a positive control and a negative control in two other lanes; or a sample reaction and an internal control in one lane and a negative control in a separate lane.

Figure 10A:
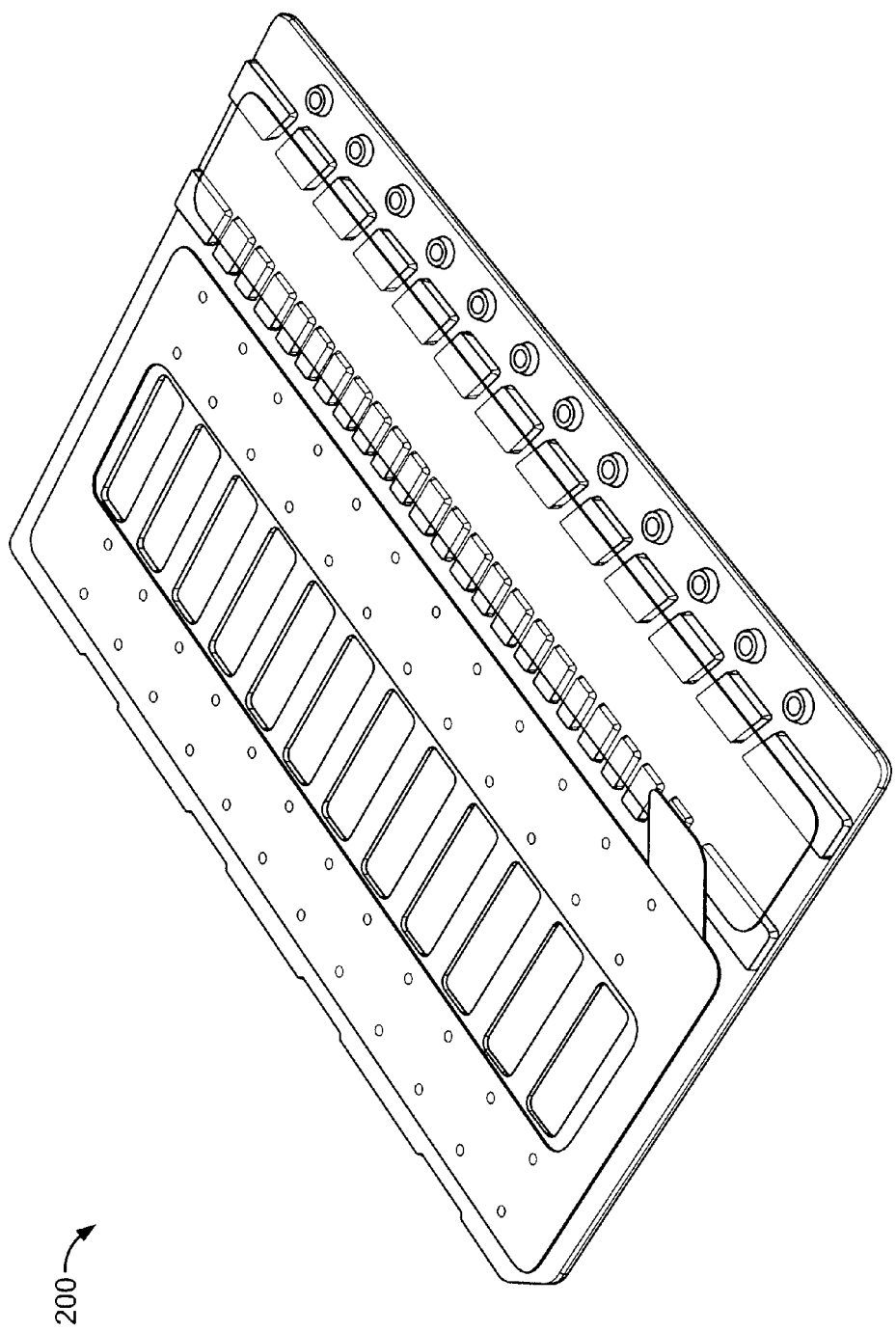
FIG. 10A shows an exemplary multi-lane cartridge.
Figure 10B:
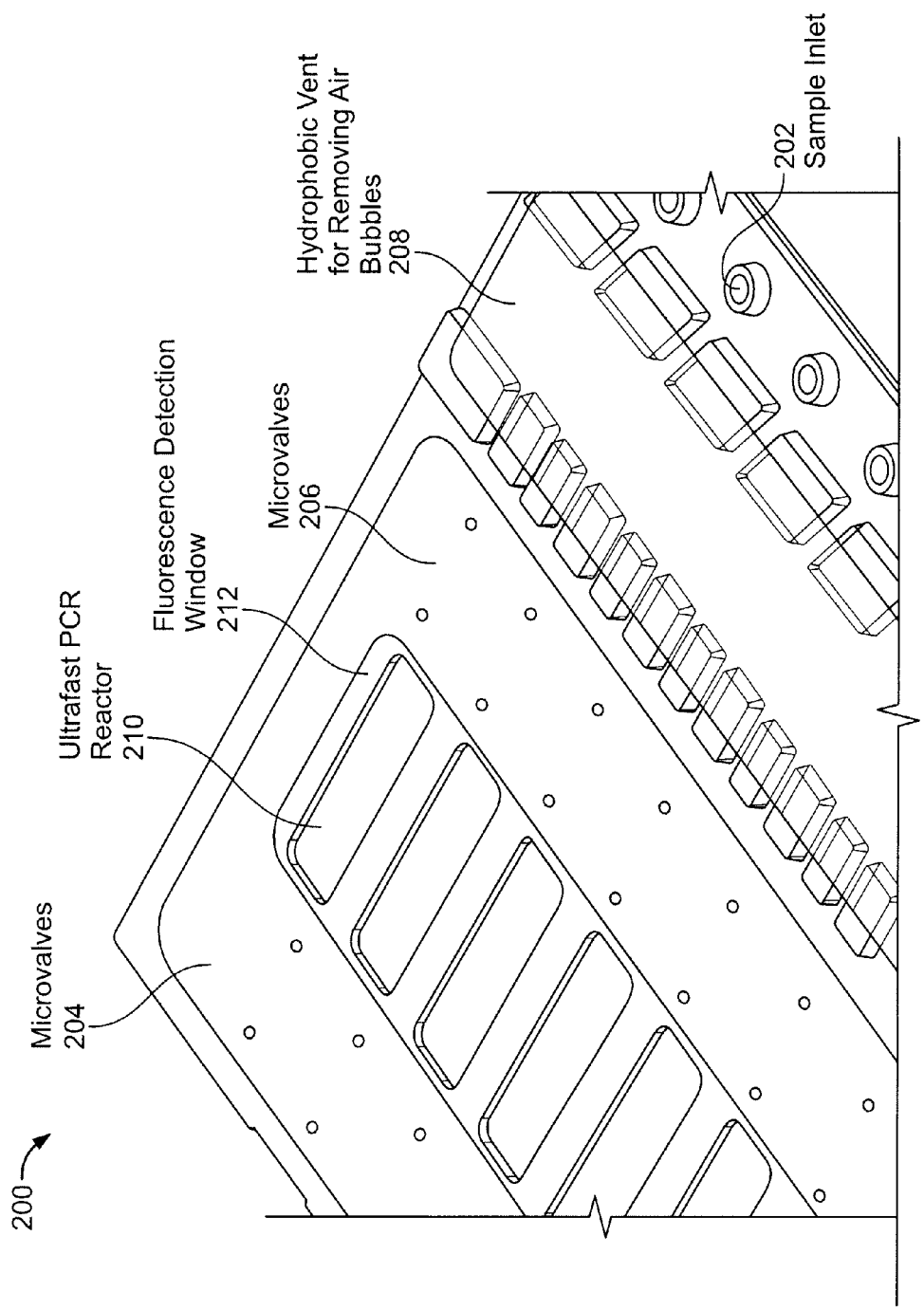
FIG. 10B shows a portion of an exemplary multi-lane cartridge.

FIG. 10A shows a perspective view of a portion of an exemplary microfluidic cartridge 200 according to the present technology. FIG. 10B shows a close-up view of a portion of the cartridge 200 of FIG. 10A illustrating various representative components. The cartridge 200 may be referred to as a multi-lane PCR cartridge with dedicated sample inlets 202. For example sample inlet 202 is configured to accept a liquid transfer member (not shown) such as a syringe, a pipette, or a PCR tube containing a PCR ready sample. More than one inlet 202 is shown in FIGS. 10A, 10B, wherein one inlet operates in conjunction with a single sample lane. Various components of microfluidic circuitry in each lane are also visible. For example, microvalves 204, and 206, and hydrophobic vents 208 for removing air bubbles, are parts of microfluidic circuitry in a given lane. Also shown is an ultrafast PCR reactor 210, which, as further described herein, is a microfluidic channel in a given sample lane that is long enough to permit PCR to amplify polynucleotides present in a sample. Above each PCR reactor 210 is a window 212 that permits detection of fluorescence from a fluorescent substance in PCR reactor 210 when a detector is situated above window 212. It is to be understood that other configurations of windows are possible including, but not limited to, a single window that straddles each PCR reactor across the width of cartridge 200.

In preferred embodiments, the multi-sample cartridge has a size substantially the same as that of a 96-well plate as is customarily used in the art. Advantageously, then, such a cartridge may be used with plate handlers used elsewhere in the art.

The sample inlets of adjacent lanes are reasonably spaced apart from one another to prevent any contamination of one sample inlet from another sample when a user introduces a sample into any one cartridge. In an embodiment, the sample inlets are configured so as to prevent subsequent inadvertent introduction of sample into a given lane after a sample has already been introduced into that lane. In certain embodiments, the multi-sample cartridge is designed so that a spacing between the centroids of sample inlets is 9 mm, which is an industry-recognized standard. This means that, in certain embodiments the center-to-center distance between inlet holes in the cartridge that accept samples from PCR tubes, as further described herein, is 9 mm. The inlet holes can be manufactured conical in shape with an appropriate conical angle so that industry-standard pipette tips (2 µl, 20 µl, 200 µl, volumes, etc.) fit snugly therein. The cartridge herein may be adapted to suit other, later-arising, industry standards not otherwise described herein, as would be understood by one of ordinary skill in the art.

In one embodiment, an exemplary microfluidic cartridge has 12 sample lanes. The inlet ports in this embodiment have a 6 mm spacing, so that, when used in conjunction with an automated sample loader having 4 heads, spaced equidistantly at 18 mm apart, the inlets can be loaded in three batches of four inlets: e.g., inlets 1, 4, 7, and 10 together, followed by 2, 5, 8, and 11, then finally 3, 6, 9, and 12, wherein the 12 inlets are numbered consecutively from one side of the cartridge to the other as shown.

A microfluidic cartridge as used herein may be constructed from a number of layers. Accordingly, one aspect of the present technology relates to a microfluidic cartridge that comprises a first, second, third, fourth, and fifth layers wherein one or more layers define a plurality of microfluidic networks, each network having various components configured to carry out PCR on a sample in which the presence or absence of one or more polynucleotides is to be determined. In various embodiments, one or more such layers are optional.

Figure 11A:
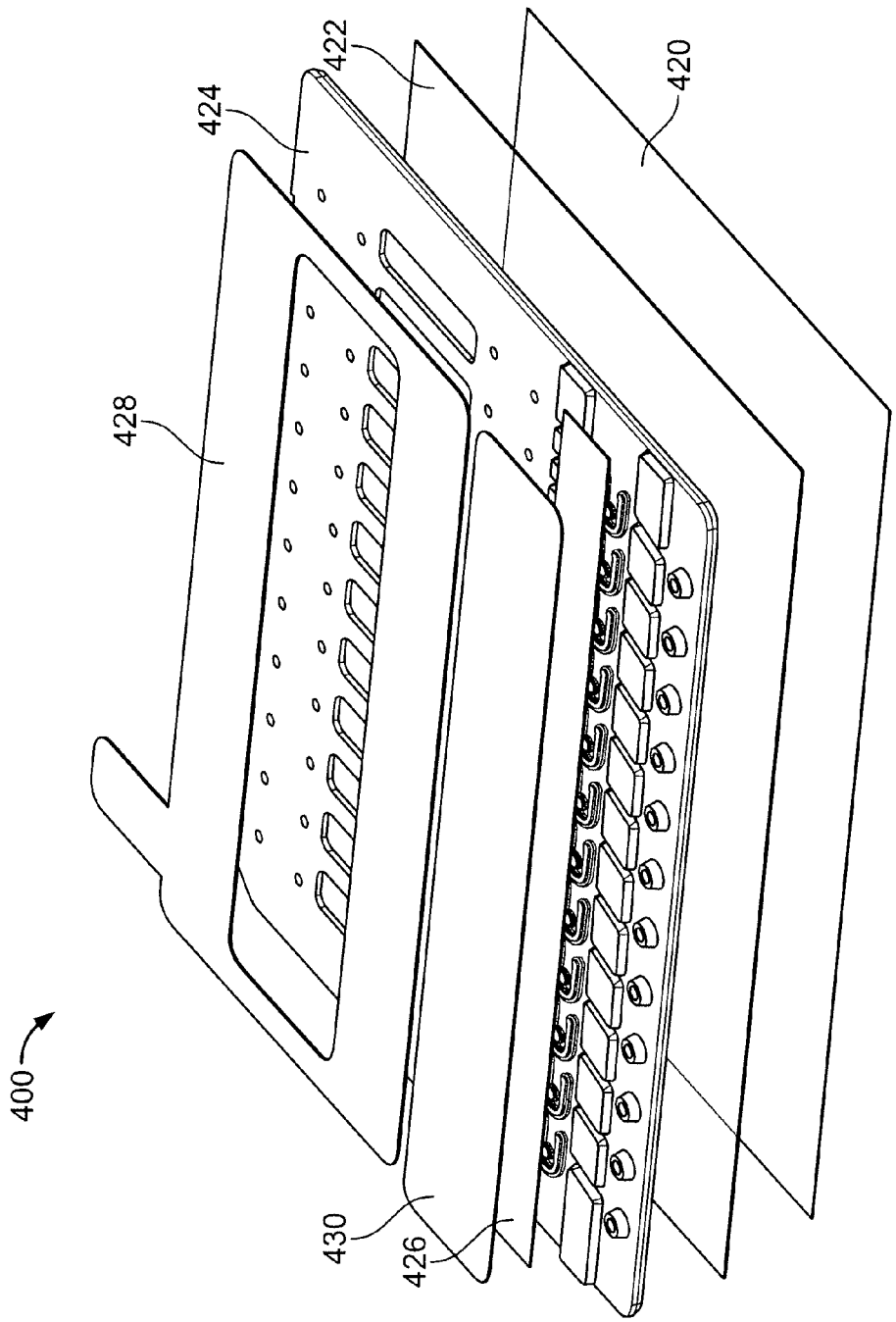
FIGS. 11A-C show exploded view of an exemplary microfluidic cartridge.
Figure 11B:
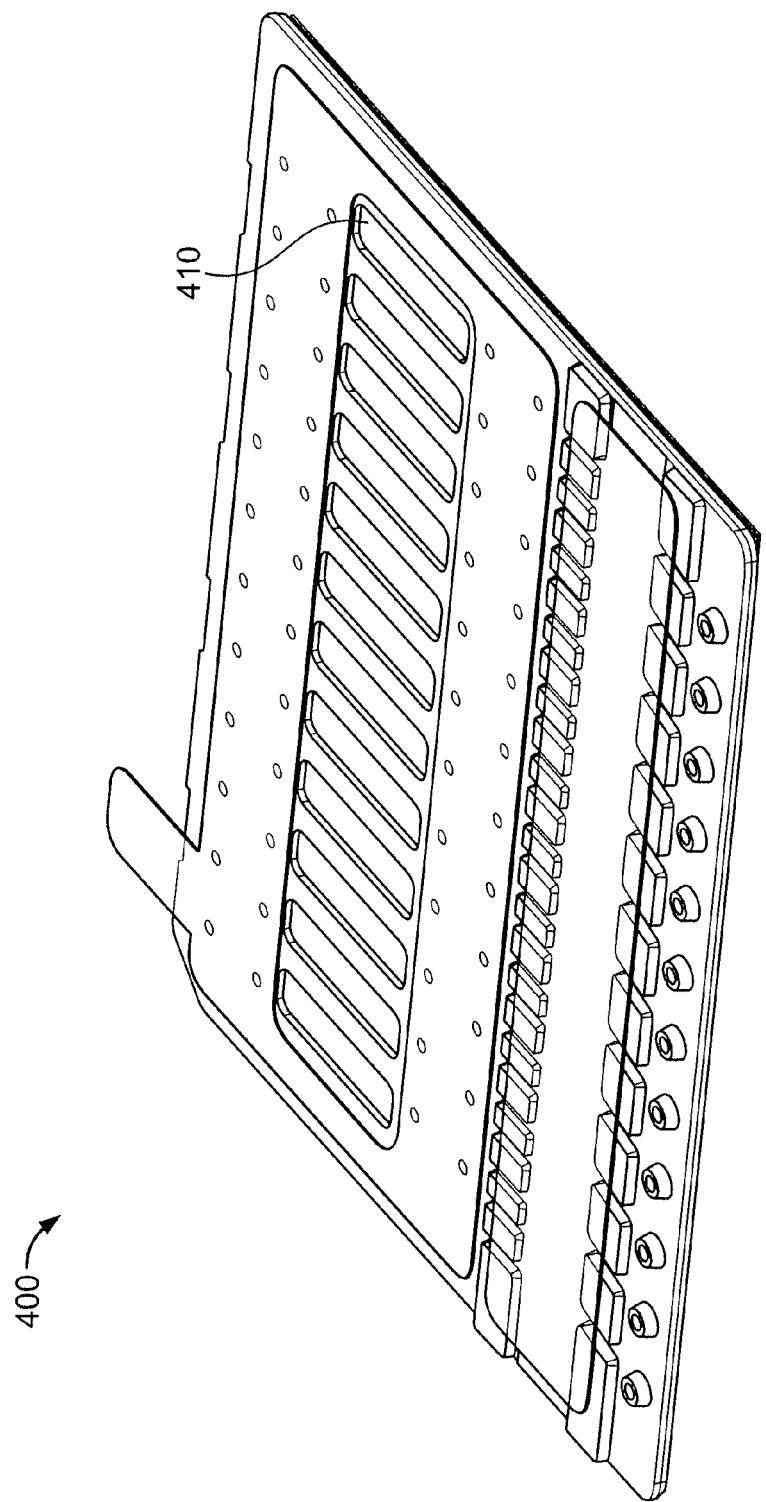
Figure 11C:
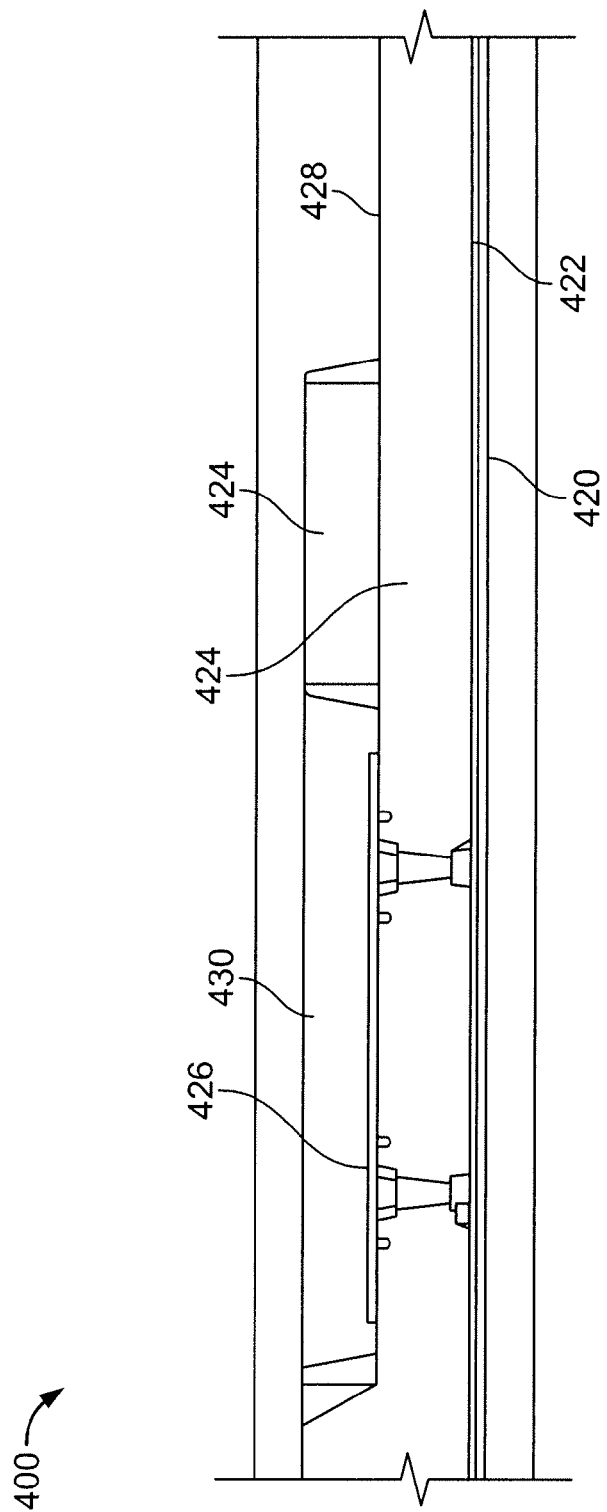

FIGS. 11A-C show various views of a layer structure of an exemplary microfluidic cartridge comprising a number of layers, as further described herein. FIG. 11A shows an exploded view; FIG. 11B shows a perspective view; and FIG. 11C shows a cross-sectional view of a sample lane in the exemplary cartridge. Referring to FIGS. 11A-C, an exemplary microfluidic cartridge 400 includes first 420, second 422, third 424, fourth 426, and fifth layers in two non-contiguous parts 428, 430 (as shown) that enclose a microfluidic network having various components configured to process multiple samples in parallel that include one or more polynucleotides to be determined.

Microfluidic cartridge 400 can be fabricated as desired. The cartridge can include a microfluidic substrate layer 424, typically injection molded out of a plastic, such as a zeonor plastic (cyclic olefin polymer), having a PCR channel and valve channels on a first side and vent channels and various inlet holes, including wax loading holes and liquid inlet holes, on a second side (disposed toward hydrophobic vent membrane 426). It is advantageous that all the microfluidic network defining structures, such as PCR reactors, valves, inlet holes, and air vents, are defined on the same single substrate 424. This attribute facilitates manufacture and assembly of the cartridge. Additionally, the material from which this substrate is formed is rigid or nondeformable, non-venting to air and other gases, and has a low autofluorescence to facilitate detection of polynucleotides during an amplification reaction performed in the microfluidic circuitry defined therein. Rigidity is advantageous because it facilitates effective and uniform contact with a heat unit as further described herein. Use of a non-venting material is also advantageous because it reduces the likelihood that the concentration of various species in liquid form will change during analysis. Use of a material having low auto-fluorescence is also important so that background fluorescence does not detract from measurement of fluorescence from the analyte of interest.

The cartridge can further include, disposed on top of the substrate 424, an oleophobic/hydrophobic vent membrane layer 426 of a porous material, such as 0.2 to 1.0 micron pore-size membrane of modified polytetrafluorethylene, the membrane being typically between about 25 and about 100 microns thick, and configured to cover the vent channels of microfluidic substrate 424, and attached thereto using, for example, heat bonding.

Typically, the microfluidic cartridge further includes a layer 428, 430 of polypropylene or other plastic label with pressure sensitive adhesive (typically between about 50 and 150 microns thick) configured to seal the wax loading holes of the valves in sustrate 424, trap air used for valve actuation, and serve as a location for operator markings. In FIG. 4A, this layer is shown in two separate pieces, 428, 430, though it would be understood by one of ordinary skill in the art that a single piece layer would be appropriate.

In various embodiments, the label is a computer-readable label. For example, the label can include a bar code, a radio frequency tag or one or more computer-readable characters. The label can be formed of a mechanically compliant material. For example, the mechanically compliant material of the label can have a thickness of between about 0.05 and about 2 millimeters and a Shore hardness of between about 25 and about 100. The label can be positioned such that it can be read by a sample identification verifier as further described herein.

The cartridge can further include a heat sealable laminate layer 422 (typically between about 100 and about 125 microns thick) attached to the bottom surface of the microfluidic substrate 424 using, for example, heat bonding. This layer serves to seal the PCR channels and vent channels in substrate 424. The cartridge can further include a thermal interface material layer 420 (typically about 125 microns thick), attached to the bottom of the heat sealable laminate layer using, for example, pressure sensitive adhesive. The layer 420 can be compressible and have a higher thermal conductivity than common plastics, thereby serving to transfer heat across the laminate more efficiently. Typically, however, layer 420 is not present.

The application of pressure to contact the cartridge to the heater of an instrument that receives the cartridge generally assists in achieving better thermal contact between the heater and the heat-receiveable parts of the cartridge, and also prevents the bottom laminate structure from expanding, as would happen if the PCR channel was only partially filled with liquid and the air entrapped therein would be thermally expanded during thermocycling.

In use, cartridge 400 is typically thermally associated with an array of heat sources configured to operate the components (e.g., valves, gates, actuators, and processing region 410) of the device. Exemplary such heater arrays are further described herein. Additional embodiments of heater arrays are described in U.S. patent application Ser. No. 11/940,315, entitled "Heater Unit for Microfluidic Diagnostic System" and filed on even date herewith, the specification of which is incorporated herein by reference in its entirety. In some embodiments, the heat sources are controlled by a computer processor and actuated according to a desired protocol. Processors configured to operate microfluidic devices are described in, e.g., U.S. application Ser. No. 09/819,105, filed Mar. 28, 2001, which application is incorporated herein by reference.

In various embodiments, during transport and storage, the microfluidic cartridge can be further surrounded by a sealed pouch. The microfluidic cartridge can be sealed in the pouch with an inert gas. The microfluidic cartridge can be disposable for example after one or more of its sample lanes have been used.

Highly Multiplexed Embodiments

Embodiments of the cartridge described herein may be constructed that have high-density microfluidic circuitry on a single cartridge that thereby permit processing of multiple samples in parallel, or in sequence, on a single cartridge. Preferred numbers of such multiple samples include 20, 24, 36, 40, 48, 50, 60, 64, 72, 80, 84, 96, and 100, but it would be understood that still other numbers are consistent with the apparatus and cartridge herein, where deemed convenient and practical.

Accordingly, different configurations of lanes, sample inlets, and associated heater networks than those explicitly depicted in the FIGURES and examples that can facilitate processing such numbers of samples on a single cartridge are within the scope of the instant disclosure. Similarly, alternative configurations of detectors and heating elements for use in conjunction with such a highly multiplexed cartridge are also within the scope of the description herein.

It is also to be understood that the microfluidic cartridges described herein are not to be limited to rectangular shapes, but can include cartridges having circular, elliptical, triangular, rhombohedral, square, and other shapes. Such shapes may also be adapted to include some irregularity, such as a cut-out, to facilitate placement in a complementary apparatus as further described herein.

Figure 12:
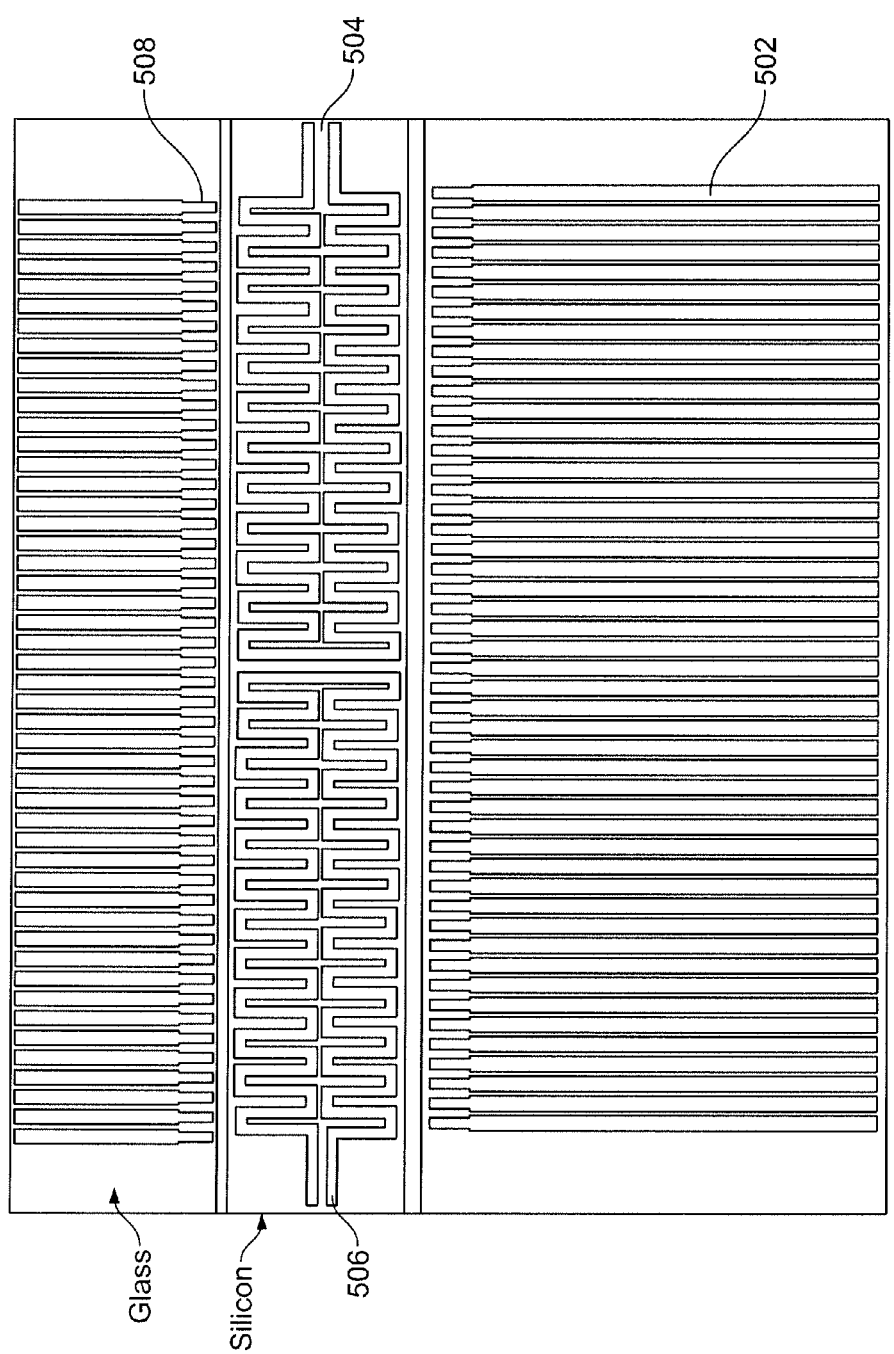
FIG. 12 shows an exemplary highly-multiplexed microfluidic cartridge.

In an exemplary embodiment, a highly multiplexed cartridge has 48 sample lanes, and permits independent control of each valve in each lane by suitably configured heater circuitry, with 2 banks of thermo cycling protocols per lane, as shown in FIG. 12. In the embodiment in FIG. 12, the heaters (shown superimposed on the lanes) are arranged in three arrays 502, 504, with 506, and 508. The heaters are themselves disposed within one or more substrates. Heater arrays 502, 508 in two separate glass regions only apply heat to valves in the microfluidic networks in each lane. Because of the low thermal conductivity of glass, the individual valves may be heated separately from one another. This permits samples to be loaded into the cartridge at different times, and passed to the PCR reaction chambers independently of one another. The PCR heaters 504,506 are mounted on a silicon substrate—and are not readily heated individually, but thereby permit batch processing of PCR samples, where multiple samples from different lanes are amplified by the same set of heating/cooling cycles. It is preferable for the PCR heaters to be arranged in 2 banks (the heater arrays 506 on the left and right 508 are not in electrical communication with one another), thereby permitting a separate degree of sample control.

Figure 13:
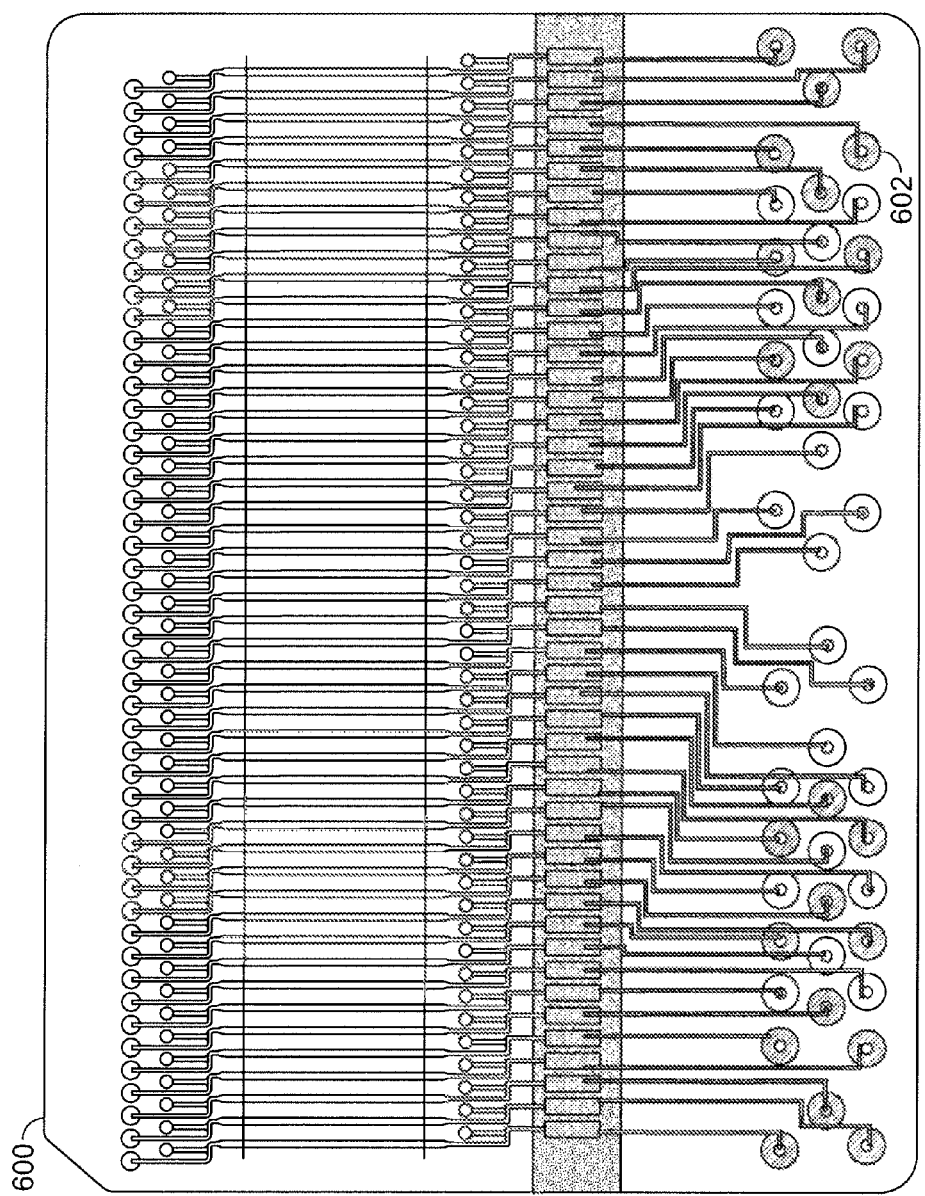
FIGS. 13-16 show various aspects of exemplary highly multiplexed microfluidic cartridges.

FIG. 13 shows a representative 48-sample cartridge 600 compatible with the heater arrays of FIG. 12, and having a configuration of inlets 602 different to that depicted o other cartridges herein. The inlet configuration is exemplary and has been designed to maximize efficiency of space usage on the cartridge. The inlet configuration can be compatible with an automatic pipetting machine that has dispensing heads situated at a 9 mm spacing. For example, such a machine having 4 heads can load 4 inlets at once, in 12 discrete steps, for the cartridge of FIG. 13. Other configurations of inlets though not explicitly described or depicted are compatible with the technology described herein.

Figure 14:
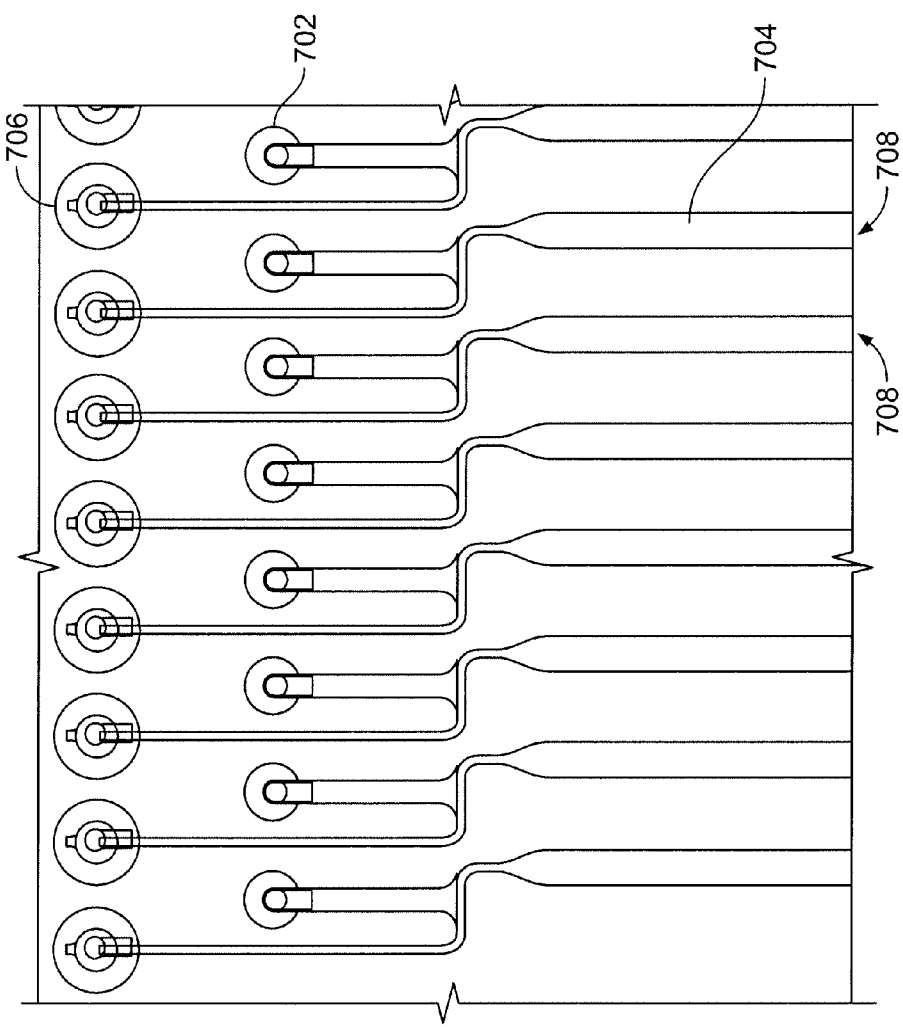

FIG. 14 shows, in close up, an exemplary spacing of valves 702, channels 704, and vents 796, in adjacent lanes 708 of a multi-sample microfluidic cartridge for example as shown in FIG. 13.

Figure 15:
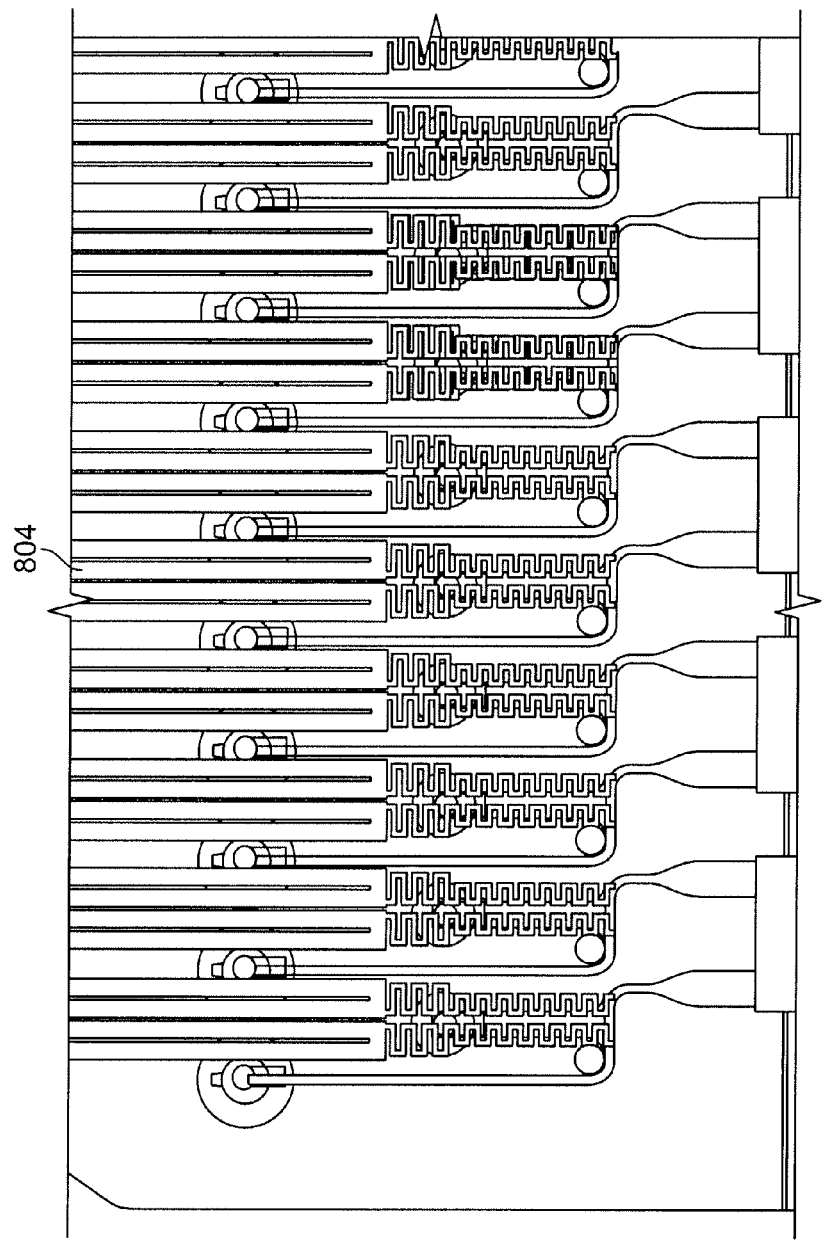
Figure 16:
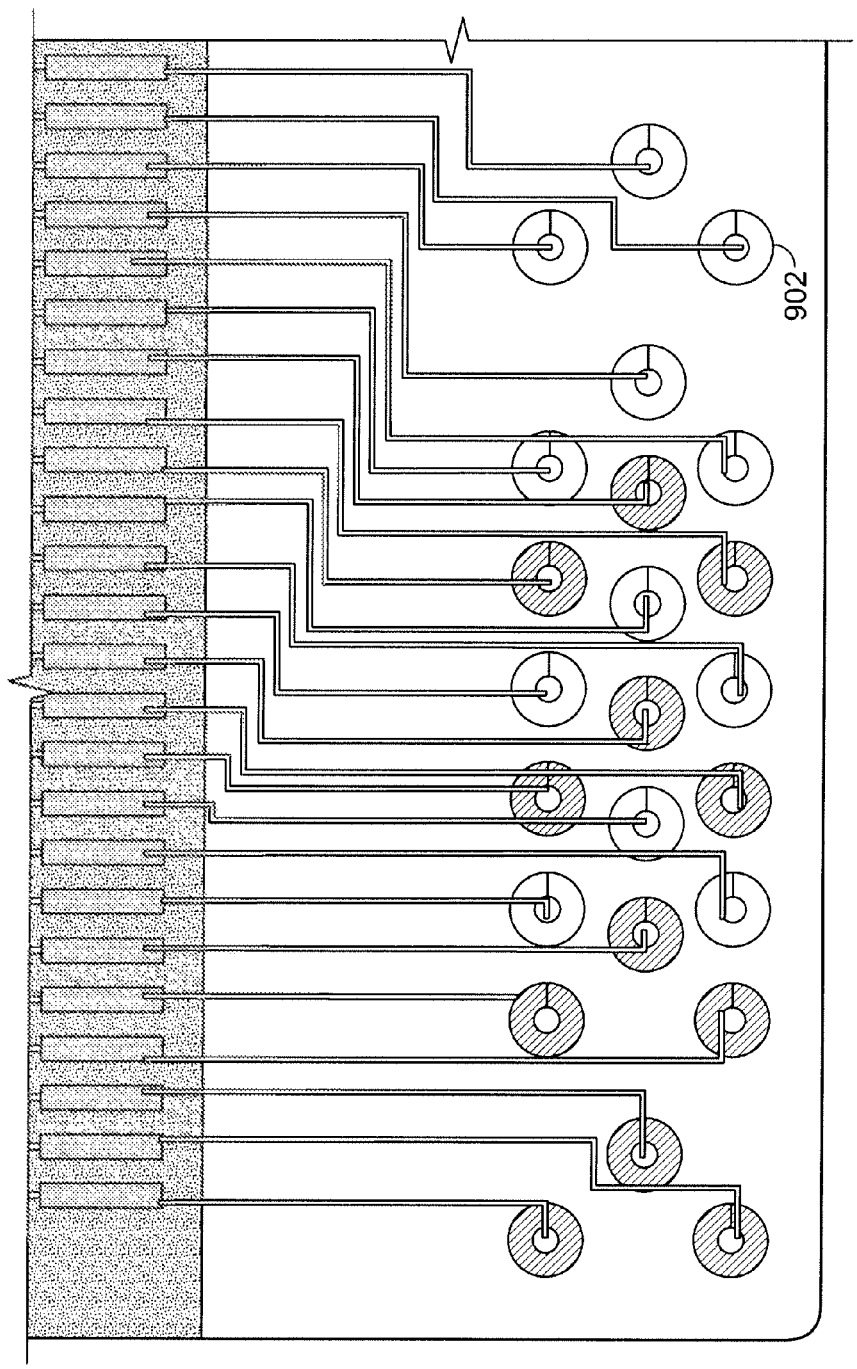

FIGS. 15 and 16 show close-ups of, respectively, heater arrays 804 compatible with, and inlets 902 on, the exemplary cartridge shown in FIG. 14.

Figure 17A:
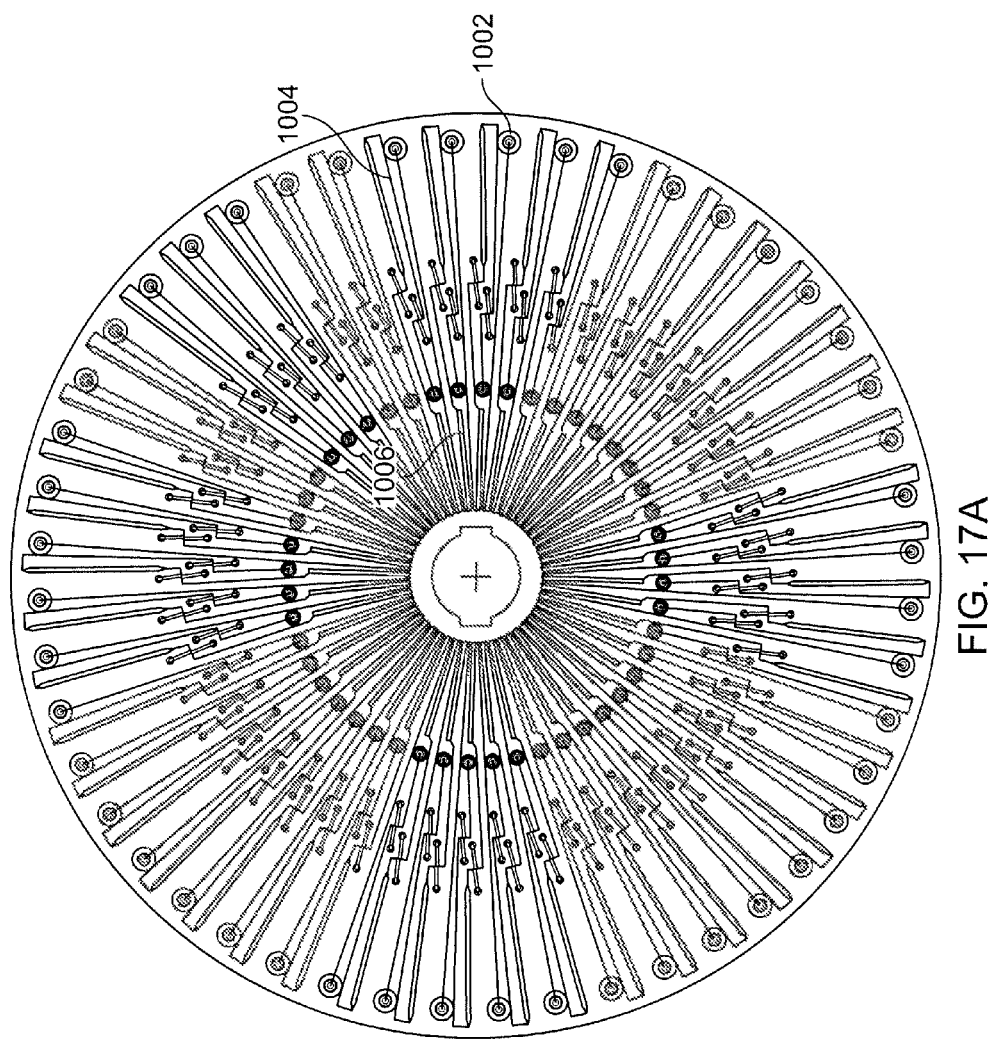
FIGS. 17A-C show various aspects of a radially configured highly multiplexed microfluidic cartridge.
Figure 17B:
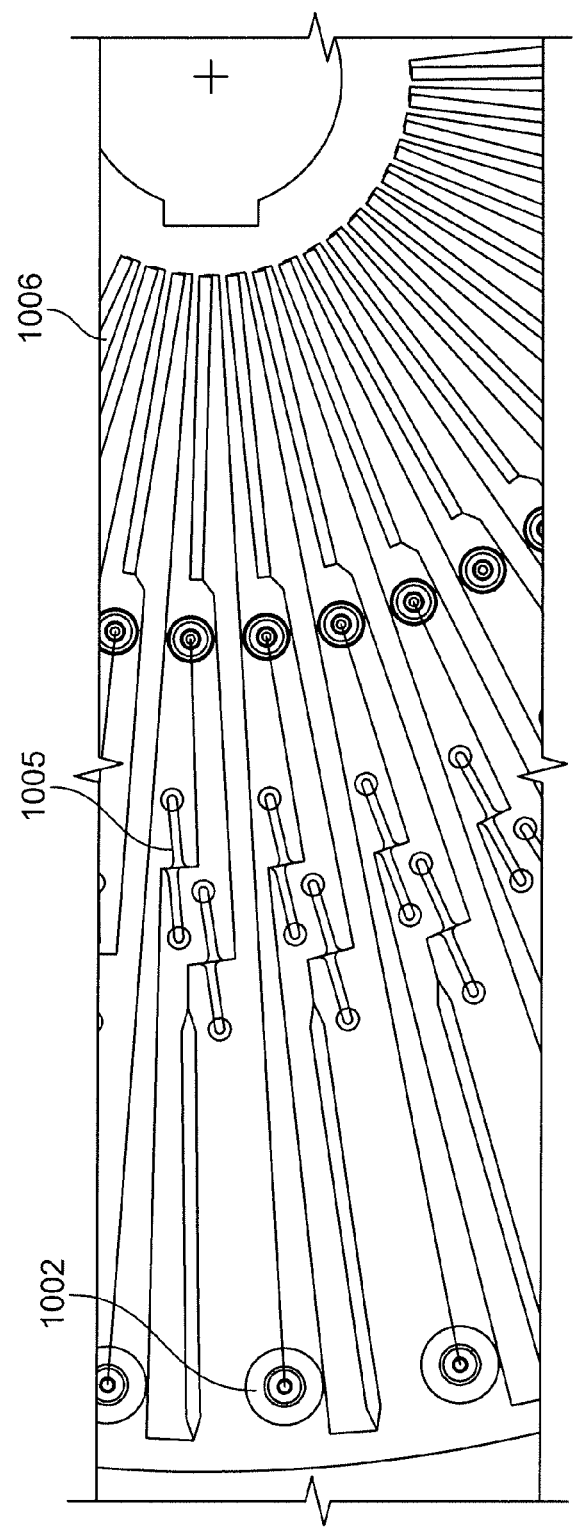
Figure 17C:
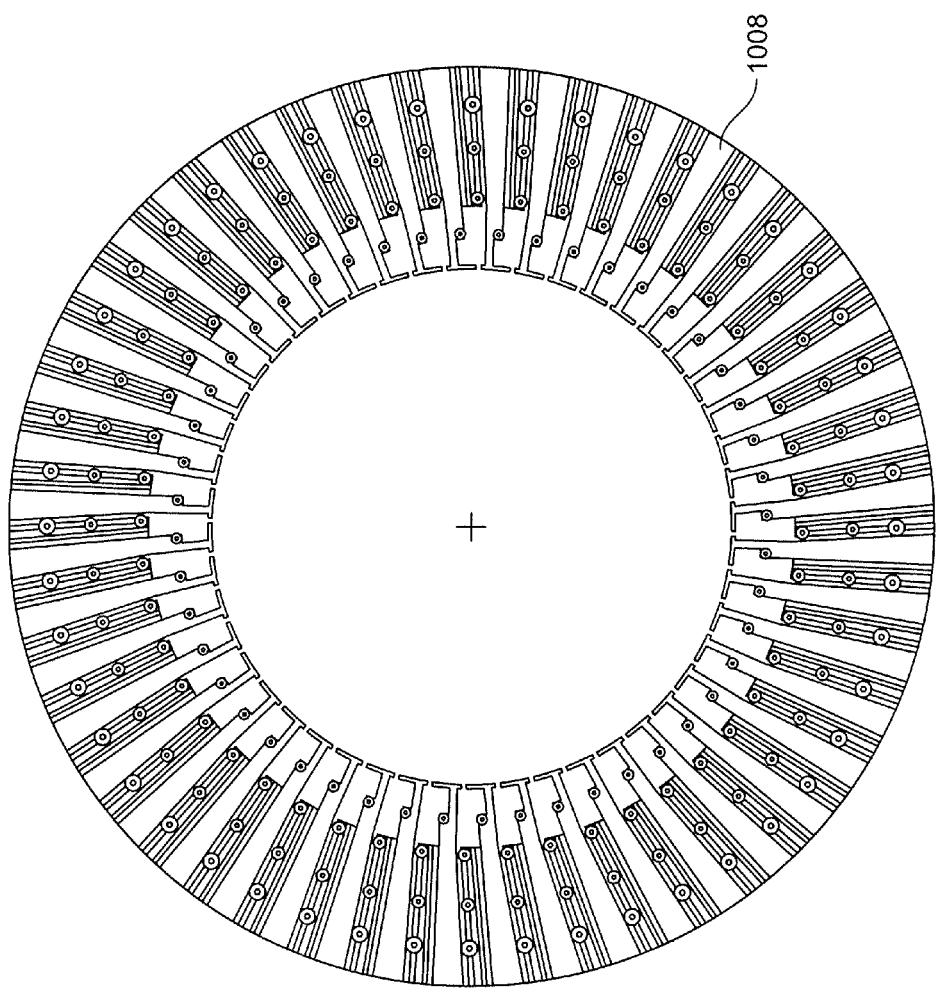

FIGS. 17A and 17B show various views of an embodiment of a radially-configured highly-multiplexed cartridge, having a number of inlets 1002, microfluidic lanes 1004, valves 1005, and PCR reaction chambers 1006. FIG. 17C shows an array of heater elements 1008 compatible with the cartridge layout of FIG. 17A.

The various embodiments shown in FIGS. 12-17C are compatible with liquid dispensers, receiving bays, and detectors that are configured differently from the other specific examples described herein.

During the design and manufacture of highly multiplexed cartridges, photolithographic processing steps such as etching, hole drilling/photo-chemical drilling/sand-blasting/ion-milling processes should be optimized to give well defined holes and microchannel pattern. Proper distances between channels should be identified and maintained to obtain good bonding between the microchannel substrate and the heat conducting substrate layer. In particular, it is desirable that minimal distances are maintained between pairs of adjacent microchannels to promote, reliable bonding of the laminate in between the channels.

The fabrication by injection molding of these complicated microfluidic structures having multiple channels and multiple inlet holes entails proper consideration of dimensional repeatability of these structures over multiple shots from the injection molding master pattern. Proper consideration is also attached to the placement of ejector pins to push out the structure from the mold without causing warp, bend or stretching of it. For example, impression of the ejector pins on the microfluidic substrate should not sink into the substrate thereby preventing planarity of the surface of the cartridge. The accurate placement of various inlet holes (such as sample inlet holes, valve inlet holes and vent holes) relative to adjacent microfluidic channels is also important because the presence of these holes can cause knit-lines to form that might cause unintended leak from a hole to a microchannel. Highly multiplexed microfluidic substrates may be fabricated in other materials such as glass, silicon.

The size of the substrate relative to the number of holes is also factor during fabrication because it is easy to make a substrate having just a simple microfluidic network with a few holes (maybe fewer than 10 holes) and a few microchannels, but making a substrate having over 24, or over 48, or over 72 holes, etc., is more difficult.

Microfluidic Networks

Particular components of exemplary microfluidic networks are further described herein.

Channels of a microfluidic network in a lane of cartridge typically have at least one sub-millimeter cross-sectional dimension. For example, channels of such a network may have a width and/or a depth of about 1 mm or less (e.g., about 750 microns or less, about 500 microns, or less, about 250 microns or less).

Figure 18:
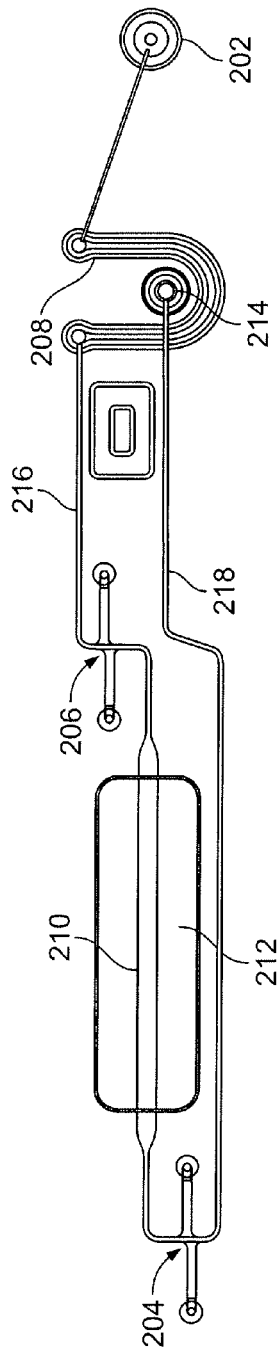
FIG. 18 shows an exemplary microfluidic network in a lane of a multi-lane cartridge.

FIG. 18 shows a plan view of a representative microfluidic circuit found in one lane of a multi-lane cartridge such as shown in FIGS. 10A and 10B. It would be understood by one skilled in the art that other configurations of microfluidic network would be consistent with the function of the cartridges and apparatus described herein. In operation of the cartridge, in sequence, sample is introduced through liquid inlet 202, optionally flows into a bubble removal vent channel 208 (which permits adventitious air bubbles introduced into the sample during entry, to escape), and continues along a channel 216. Typically, when using a robotic dispenser of liquid sample, the volume is dispensed accurately enough that formation of bubbles is not a significant problem, and the presence of vent channel 208 is not necessary. Thus, in certain embodiments, the bubble removal vent channel 208 is not present and sample flows directly into channel 216. Throughout the operation of cartridge 200, the fluid is manipulated as a microdroplet (not shown in the FIGURES). Valves 204 and 206 are initially both open, so that a microdroplet of sample-containing fluid can be pumped into PCR reactor channel 210 from inlet hole 202 under influence of force from the sample injection operation. Upon initiating of processing, the detector present on top of the PCR reactor 210 checks for the presence of liquid in the PCR channel, and then valves 204 and 206 are closed to isolate the PCR reaction mix from the outside. In one embodiment, the checking of the presence of liquid in the PCR channel is by measuring the heat ramp rate, such as by one or more temperature sensors in the heating unit. A channel with liquid absent will heat up faster than one in which, e.g., a sample, is present.

Both valves 204 and 206 are closed prior to thermocycling to prevent or reduce any evaporation of liquid, bubble generation, or movement of fluid from the PCR reactor. End vent 214 is configured to prevent a user from introducing an excess amount of liquid into the microfluidic cartridge, as well as playing a role of containing any sample from spilling over to unintended parts of the cartridge. A user may input sample volumes as small as an amount to fill the region from the bubble removal vent (if present) to the middle of the microreactor, or up to valve 204 or beyond valve 204. The use of microvalves prevents both loss of liquid or vapor thereby enabling even a partially filled reactor to successfully complete a PCR thermocycling reaction.

The reactor 210 is a microfluidic channel that is heated through a series of cycles to carry out amplification of nucleotides in the sample, as further described herein, and according to amplification protocols known to those of ordinary skill in the art. The inside walls of the channel in the PCR reactor are typically made very smooth and polished to a shiny finish (for example, using a polish selected from SPI A1, SPI A2, SPI A3, SPI B1, or SPI B2) during manufacture. This is in order to minimize any microscopic quantities of air trapped in the surface of the PCR channel, which would causing bubbling during the thermocycling steps. The presence of bubbles especially in the detection region of the PCR channel could also cause a false or inaccurate reading while monitoring progress of the PCR. Additionally, the PCR channel can be made shallow such that the temperature gradient across the depth of the channel is minimized.

The region of the cartridge 212 above PCR reactor 210 is a thinned down section to reduce thermal mass and autofluorescence from plastic in the cartridge. It permits a detector to more reliably monitor progress of the reaction and also to detect fluorescence from a probe that binds to a quantity of amplified nucleotide. Exemplary probes are further described herein. The region 212 can be made of thinner material than the rest of the cartridge so as to permit the PCR channel to be more responsive to a heating cycle (for example, to rapidly heat and cool between temperatures appropriate for denaturing and annealing steps), and so as to reduce glare, autofluorescence, and undue absorption of fluorescence.

After PCR has been carried out on a sample, and presence or absence of a polynucleotide of interest has been determined, it is preferred that the amplified sample remains in the cartridge and that the cartridge is either used again (if one or more lanes remain unused), or disposed of. Should a user wish to run a post amplification analysis, such as gel electrophoresis, the user may pierce a hole through the laminate of the cartridge, and recover an amount—typically about 1.5 microliter—of PCR product. The user may also place the individual PCR lane on a special narrow heated plate, maintained at a temperature to melt the wax in the valve, and then aspirate the reacted sample from the inlet hole of that PCR lane.

In various embodiments, the microfluidic network can optionally include at least one reservoir configured to contain waste.

Table 1 outlines typical volumes, pumping pressures, and operation times associated with various components of a microfluidic cartridge described herein.

TABLE 1

| Operation | Pumping Pressure | Displacement Volume | Time of Operation |
|---|---|---|---|
| Moving valve wax plugs | ~1-2 psi | <1 µl | 5-15 seconds |
| Operation | Pump Used | Pump Design | Pump Actuation |
| Moving valve wax plugs | Thermo-pneumatic pump | 1 µl of trapped air | Heat trapped air to ~70-90 C. |

Valves

A valve (sometimes referred to herein as a microvalve) is a component in communication with a channel, such that the valve has a normally open state allowing material to pass along a channel from a position on one side of the valve (e.g., upstream of the valve) to a position on the other side of the valve (e.g., downstream of the valve). Upon actuation of the valve, the valve transitions to a closed state that prevents material from passing along the channel from one side of the valve to the other. For example, in one embodiment, a valve can include a mass of a thermally responsive substance (TRS) that is relatively immobile at a first temperature and more mobile at a second temperature. The first and second temperatures are insufficiently high to damage materials, such as polymer layers of a microfluidic cartridge in which the valve is situated. A mass of TRS can be an essentially solid mass or an agglomeration of smaller particles that cooperate to obstruct the passage when the valve is closed. Examples of TRS's include a eutectic alloy (e.g., a solder), wax (e.g., an olefin), polymers, plastics, and combinations thereof. The TRS can also be a blend of variety of materials, such as an emulsion of thermoelastic polymer blended with air microbubbles (to enable higher thermal expansion, as well as reversible expansion and contraction), polymer blended with expancel material (offering higher thermal expansion), polymer blended with heat conducting microspheres (offering faster heat conduction and hence, faster melting profiles), or a polymer blended with magnetic microspheres (to permit magnetic actuation of the melted thermoresponsive material).

Generally, for such a valve, the second temperature is less than about 90° C. and the first temperature is less than the second temperature (e.g., about 70° C. or less). Typically, a chamber is in gaseous communication with the mass of TRS. The valve is in communication with a source of heat that can be selectively applied to the chamber of air and to the TRS. Upon heating gas (e.g., air) in the chamber and heating the mass of TRS to the second temperature, gas pressure within the chamber due to expansion of the volume of gas, forces the mass to move into the channel, thereby obstructing material from passing therealong.

Figure 19A:
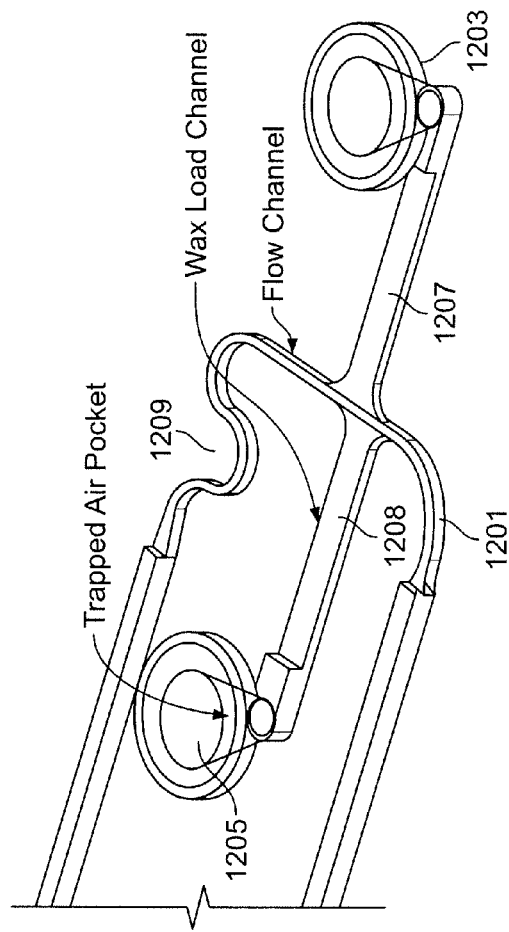
FIGS. 19A-19D show exemplary microfluidic valves.

An exemplary valve is shown in FIG. 19A. The valve of FIG. 19A has two chambers of air 1203, 1205 in contact with, respectively, each of two channels 1207, 1208 containing TRS. The air chambers also serve as loading ports for TRS during manufacture of the valve, as further described herein. In order to make the valve sealing very robust and reliable, the flow channel 1201 (along which, e.g., sample passes) at the valve junction is made narrow (typically 150 µm wide, and 150 µm deep or narrower), and the constricted portion of the flow channel is made at least 0.5 or 1 mm long such that the TRS seals up a long narrow channel thereby reducing any leakage through the walls of the channel. In the case of a bad seal, there may be leakage of fluid around walls of channel, past the TRS, when the valve is in the closed state. In order to minimize this, the flow channel is narrowed and elongated as much as possible. In order to accommodate such a length of channel on a cartridge where space may be at a premium, the flow channel can incorporate one or more curves 1209 as shown in FIG. 19A. The valve operates by heating air in the TRS-loading port, which forces the TRS forwards into the flow-channel in a manner so that it does not come back to its original position. In this way, both air and TRS are heated during operation.

Figure 19B:
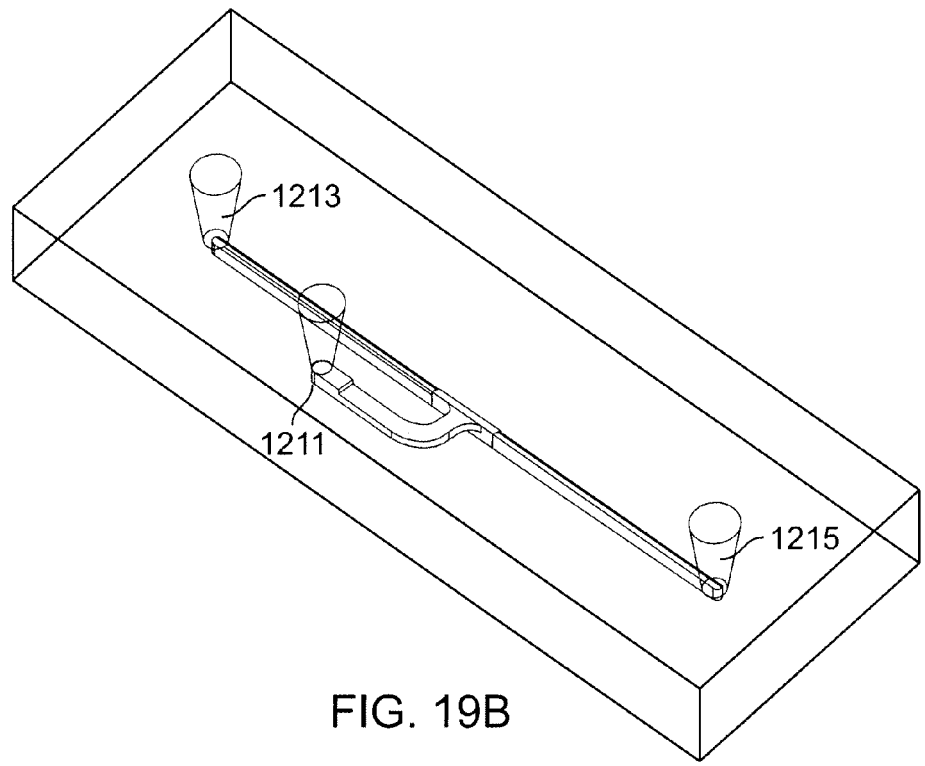

In various other embodiments, a valve for use with a microfluidic network in a microfluidic cartridge herein can be a bent valve as shown in FIG. 19B. Such a configuration reduces the footprint of the valve and hence reduces cost per part for highly dense microfluidic cartridges. A single valve loading hole 1211 is positioned in the center, that serves as an inlet for thermally responsive substance. The leftmost vent 1213 can be configured to be an inlet for, e.g., sample, and the rightmost vent 1215 acts as an exit for, e.g., air. This configuration can be used as a prototype for testing such attributes as valve and channel geometry and materials.

Figure 19C:
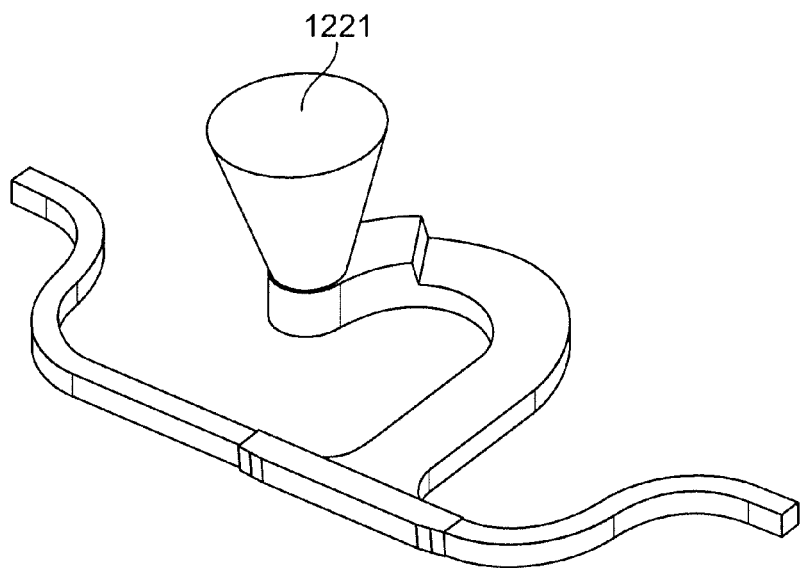

In various other embodiments, a valve for use with a microfluidic network can include a curved valve as shown in FIG. 19C, in order to reduce the effective cross-section of the valve, thereby enabling manufacture of cheaper dense microfluidic devices. Such a valve can function with a single valve loading hole and air chamber 1221 instead of a pair as shown in FIG. 19A.

Gates

Figure 19D:
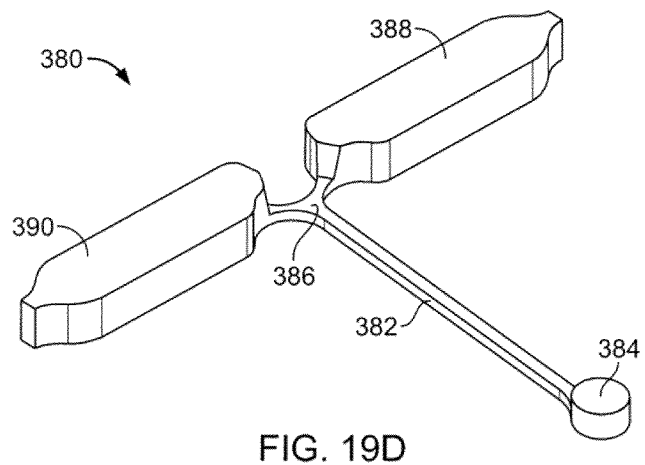

FIG. 19D shows an exemplary gate as may optionally be used in a microfluidic network herein. A gate can be a component that can have a closed state that does not allow material to pass along a channel from a position on one side of the gate to another side of the gate, and an open state that does allow material to pass along a channel from a position on one side of the gate to another side of the gate. Actuation of an open gate can transition the gate to a closed state in which material is not permitted to pass from one side of the gate (e.g., upstream of the gate) to the other side of the gate (e.g., downstream of the gate). Upon actuation, a closed gate can transition to an open state in which material is permitted to pass from one side of the gate (e.g., upstream of the gate) to the other side of the gate (e.g., downstream of the gate).

In various embodiments, a microfluidic network can include a narrow gate 380 as shown in FIG. 19D where a gate loading channel 382 used for loading wax from a wax loading hole 384 to a gate junction 386 can be narrower (e.g., approximately 150 µm wide and 100 microns deep). An upstream channel 388 as well as a downstream channel 390 of the gate junction 386 can be made wide (e.g., ~500 µm) and deep (e.g., ~500 µm) to help ensure the wax stops at the gate junction 386. The amount of gate material melted and moved out of the gate junction 386 may be minimized for optimal gate 380 opening. As an off-cartridge heater may be used to melt the thermally responsive substance in gate 380, a misalignment of the heater could cause the wax in the gate loading channel 382 to be melted as well. Therefore, narrowing the dimension of the loading channel may increase reliability of gate opening. In the case of excessive amounts of wax melted at the gate junction 386 and gate loading channel 382, the increased cross-sectional area of the downstream channel 390 adjacent to the gate junction 386 can prevent wax from clogging the downstream channel 390 during gate 380 opening. The dimensions of the upstream channel 388 at the gate junction 386 can be made similar to the downstream channel 390 to ensure correct wax loading during gate fabrication.

In various embodiments, the gate can be configured to minimize the effective area or footprint of the gate within the network and thus bent gate configurations, although not shown herein are consistent with the foregoing description.

Vents

In various embodiments, the microfluidic network can include at least one hydrophobic vent in addition to an end vent. A vent is a general outlet (hole) that may or may not be covered with a hydrophobic membrane. An exit hole is an example of a vent that need not be covered by a membrane.

A hydrophobic vent (e.g., a vent in FIG. 20) is a structure that permits gas to exit a channel while limiting (e.g., preventing) quantities of liquid from exiting the channel. Typically, hydrophobic vents include a layer of porous hydrophobic material (e.g., a porous filter such as a porous hydrophobic membrane from GE Osmonics, Minnetonka, Minn.) that defines a wall of the channel. As described elsewhere herein, hydrophobic vents can be used to position a microdroplet of sample at a desired location within a microfluidic network.

The hydrophobic vents of the present technology are preferably constructed so that the amount of air that escapes through them is maximized while minimizing the volume of the channel below the vent surface. Accordingly, it is preferable that the vent is constructed so as to have a hydrophobic membrane 1303 of large surface area and a shallow cross section of the microchannel below the vent surface.

Hydrophobic vents are useful for bubble removal and typically have a length of at least about 2.5 mm (e.g., at least about 5 mm, at least about 7.5 mm) along a channel 1305 (see FIG. 13). The length of the hydrophobic vent is typically at least about 5 times (e.g., at least about 10 times, at least about 20 times) larger than a depth of the channel within the hydrophobic vent. For example, in some embodiments, the channel depth within the hydrophobic vent is about 300 microns or less (e.g., about 250 microns or less, about 200 microns or less, about 150 microns or less).

The depth of the channel within the hydrophobic vent is typically about 75% or less (e.g., about 65% or less, about 60% or less) of the depth of the channel upstream 1301 and downstream (not shown) of the hydrophobic vent. For example, in some embodiments the channel depth within the hydrophobic vent is about 150 microns and the channel depth upstream and downstream of the hydrophobic vent is about 250 microns. Other dimensions are consistent with the description herein.

A width of the channel within the hydrophobic vent is typically at least about 25% wider (e.g., at least about 50% wider) than a width of the channel upstream from the vent and downstream from the vent. For example, in an exemplary embodiment, the width of the channel within the hydrophobic vent is about 400 microns, and the width of the channel upstream and downstream from the vent is about 250 microns. Other dimensions are consistent with the description herein.

Figure 20:
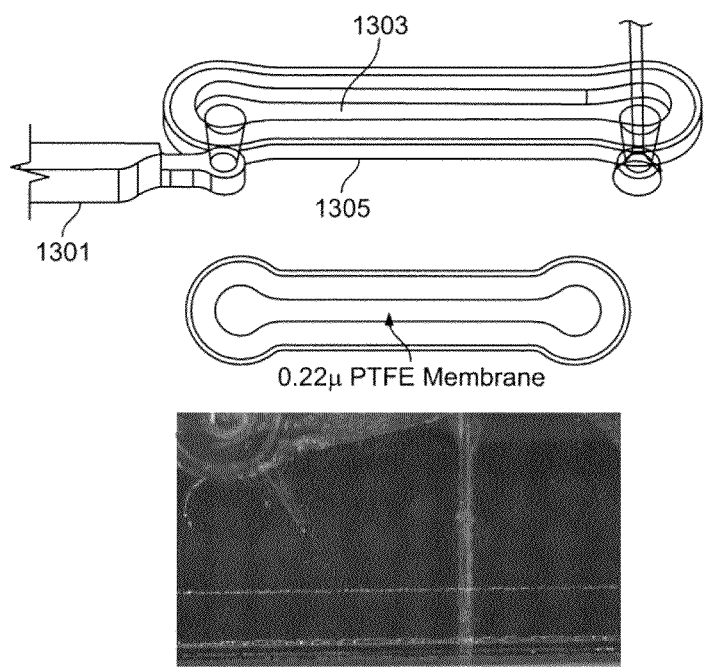
FIG. 20 shows an exemplary bubble vent.

The vent in FIG. 20 is shown in a linear configuration though it would be understood that it need not be so. A bent, kinked, curved, S-shaped, V-shaped, or U-shaped (as in item 208 FIG. 11) vent is also consistent with the manner of construction and operation described herein.

Figure 21:
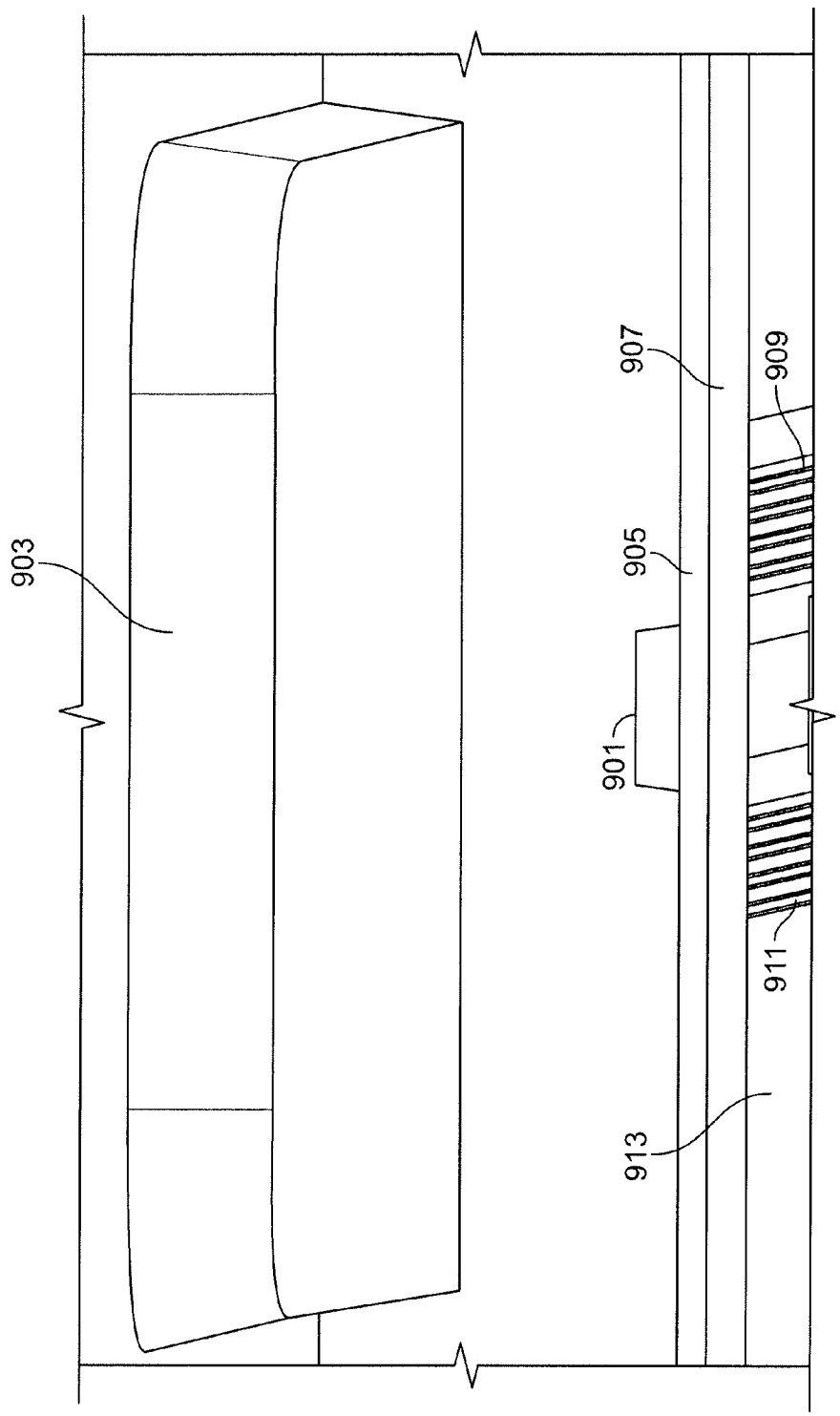
FIG. 21 shows a cross-section of a microfluidic cartridge, when in contact with a heater substrate.

Use of Cutaways in Cartridge and Substrate to Improve Rate of Cooling During PCR Cycling During a PCR amplification of a nucleotide sample, a number of thermal cycles are carried out. For improved efficiency, the cooling between each application of heat is preferably as rapid as possible. Improved rate of cooling can be achieved with various modifications to the heating substrate and/or the cartridge, as shown in FIG. 21.

Figure 22A:
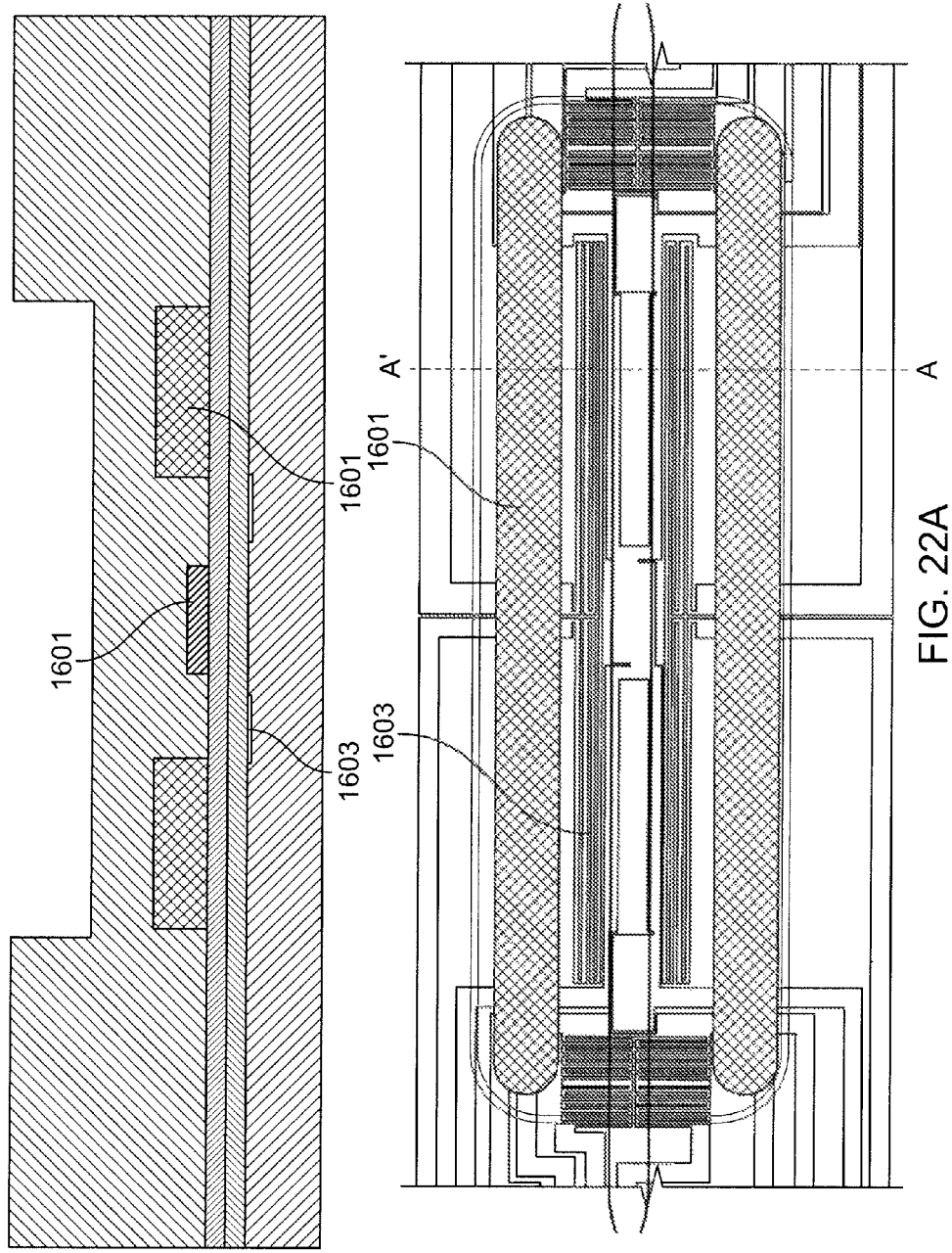
FIGS. 22A-22C shows various cut-away sections that can be used to improve cooling rates during PCR thermal cycling.

One way to achieve rapid cooling is to cutaway portions of the microfluidic cartridge substrate, as shown in FIG. 22A. The upper panel of FIG. 22A is a cross-section of an exemplary microfluidic cartridge taken along the dashed line A-A' as marked on the lower panel of FIG. 22A. PCR reaction chamber 1601, and representative heaters 1603 are shown. Also shown are two cutaway portions, one of which labeled 1601, that are situated alongside the heaters that are positioned along the long side of the PCR reaction chamber. Cutaway portions such as 1601 reduce the thermal mass of the cartridge, and also permit air to circulate within the cutaway portions. Both of these aspects permit heat to be conducted away quickly from the immediate vicinity of the PCR reaction chamber. Other configurations of cutouts, such as in shape, position, and number, are consistent with the present technology.

Figure 22B:
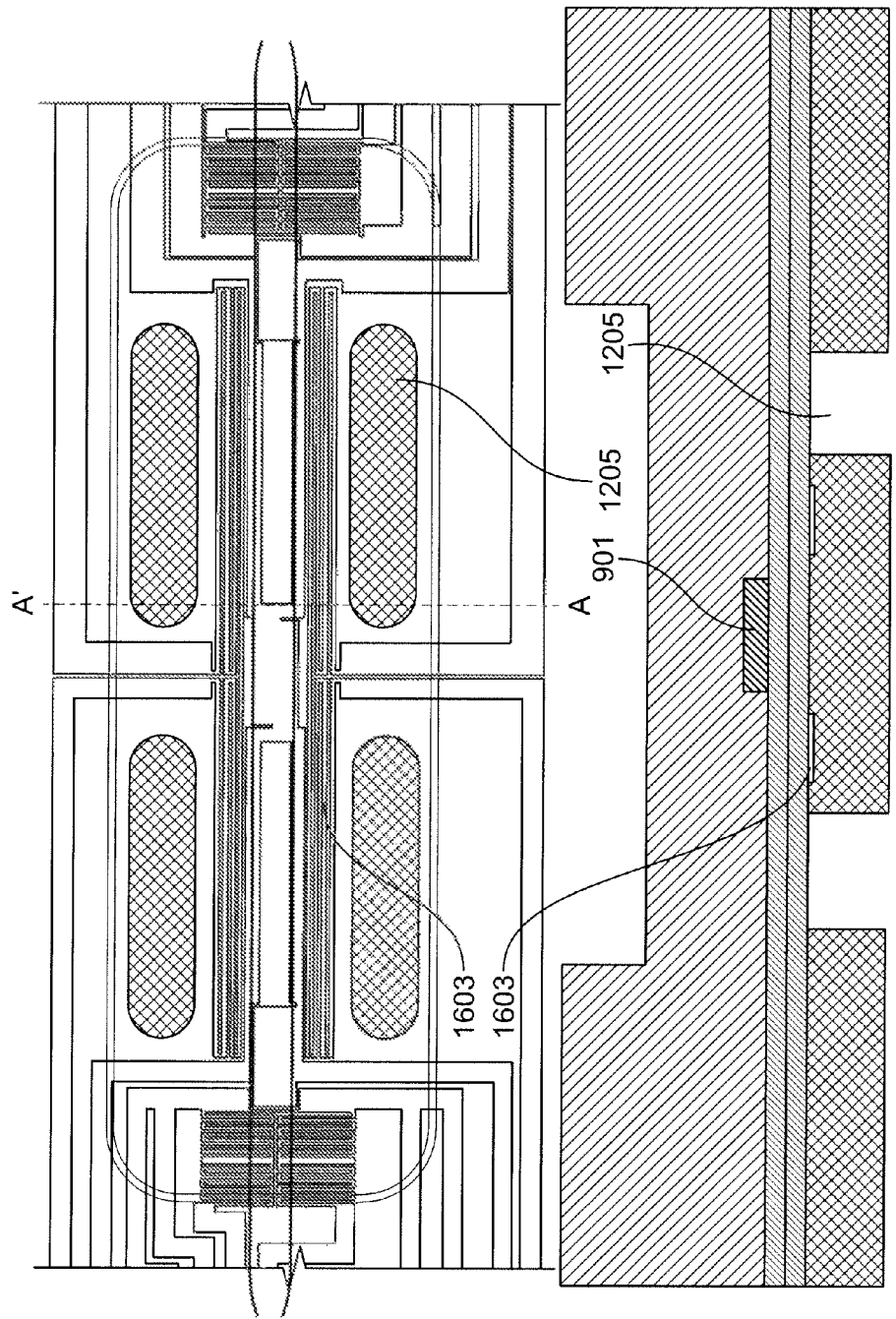

Another way to achieve rapid cooling is to cutaway portions of the heater substrate, as shown in FIG. 22B. The lower panel of FIG. 22B is a cross-section of an exemplary microfluidic cartridge and heater substrate taken along the dashed line A-A' as marked on the upper panel of FIG. 22B. PCR reaction chamber 901, and representative heaters 1003 are shown. Also shown are four cutaway portions, one of which labeled 1205, that are situated alongside the heaters that are situated along the long side of the PCR reaction chamber. Cutaway portions such as 1205 reduce the thermal mass of the heater substrate, and also permit air to circulate within the cutaway portions. Both of these aspects permit heat to be conducted away quickly from the immediate vicinity of the PCR reaction chamber. Four separate cutaway portions are shown in FIG. 22A so that control circuitry to the various heaters is not disrupted. Other configurations of cutouts, such as in shape, position, and number, are consistent with the present technology. These cutouts may be created by a method selected from: selective etching using wet etching processes, deep reactive ion etching, selective etching using $CO_2$ laser or femtosecond laser (to prevent surface cracks or stress near the surface), selective mechanical drilling, selective ultrasonic drilling, or selective abrasive particle blasting. Care has to be taken to maintain mechanically intergrity of the heater while reducing as much material as possible.

Figure 22C:
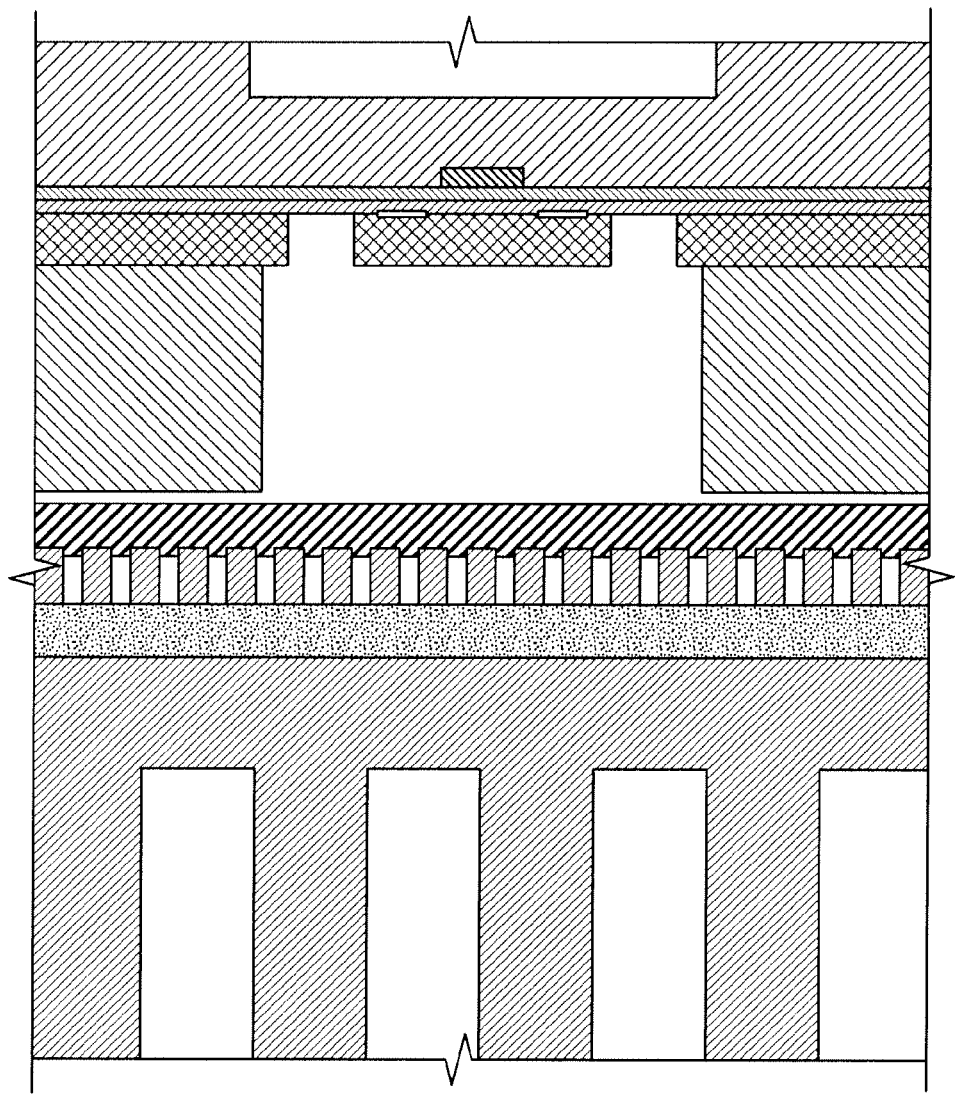

FIG. 22C shows a combination of cutouts and use of ambient air cooling to increase the cooling rate during the cooling stage of thermocycling. A substantial amount of cooling happens by convective loss from the bottom surface of the heater surface to ambient air. The driving force for this convective loss is the differential in temperatures between the glass surface and the air temperature. By decreasing the ambient air temperature by use of, for example, a peltier cooler, the rate of cooling can be increased. The convective heat loss may also be increased by keeping the air at a velocity higher than zero.

Figure 23:
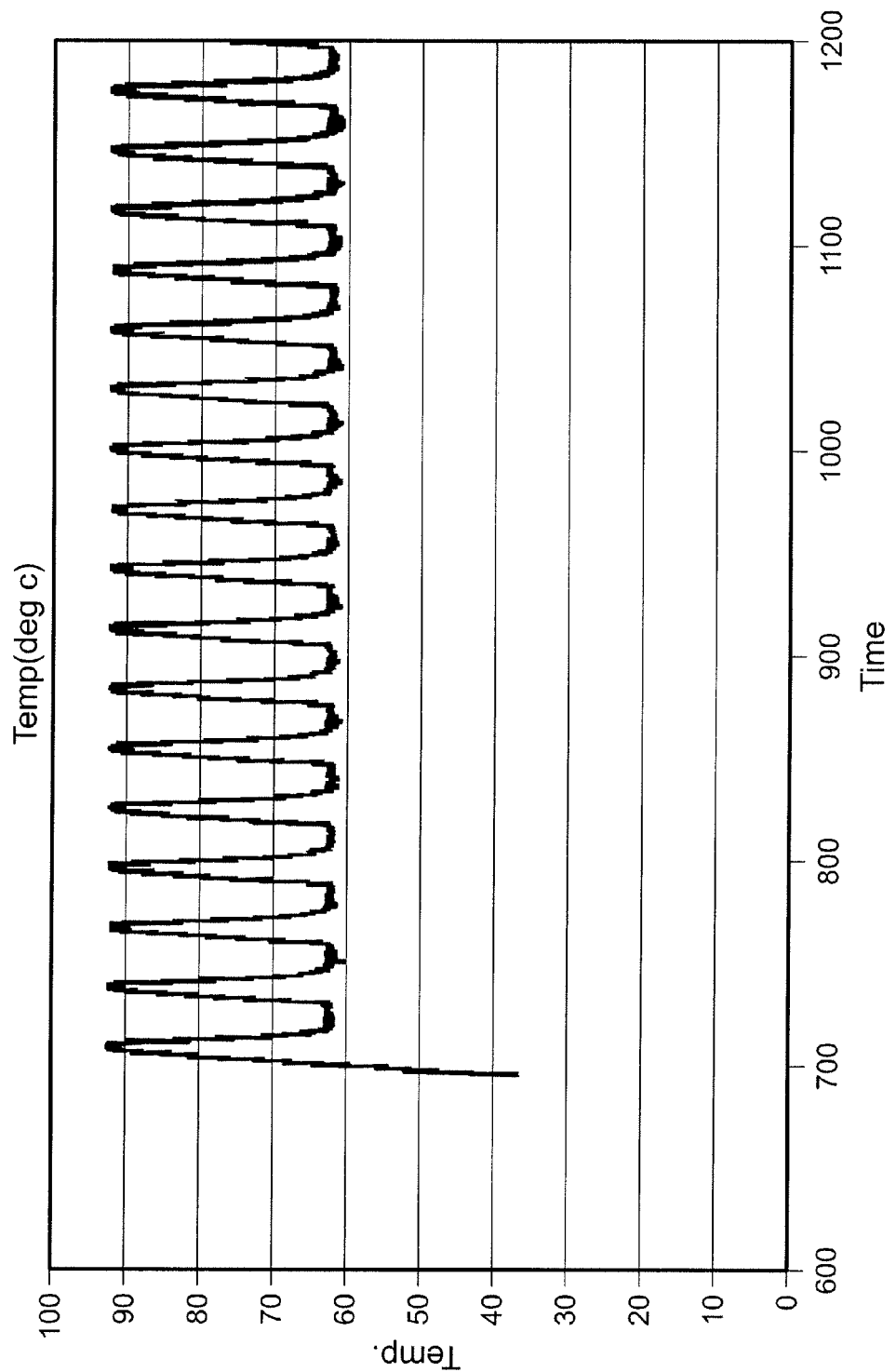
FIG. 23 shows a plot of temperature against time during a PCR process, as performed on a microfluidic cartridge as described herein.

An example of thermal cycling performance in a PCR reaction chamber obtained with a configuration as described herein, is shown in FIG. 23 for a protocol that is set to heat up the reaction mixture to 92° C., and maintain the temperature for 1 second, then cool to 62° C., and stay for 10 seconds. The cycle time shown is about 29 seconds, with 8 seconds required to heat from 62° C. and stabilize at 92° C., and 10 seconds required to cool from 92° C., and stabilize at 62° C. To minimize the overall time required for a PCR effective to produce detectable quantities of amplified material, it is important to minimize the time required for each cycle. Cycle times in the range 15-30 s, such as 18-25 s, and 20-22 s, are desirable. In general, an average PCR cycle time of 25 seconds as well as cycle times as low as 20 seconds are typical with the technology described herein. Using reaction volumes less than a microliter (such as a few hundred nanoliters or less) permits use of an associated smaller PCR chamber, and enables cycle times as low as 15 seconds. An average cycle time of 25 seconds and as low as 20 seconds can be achieved by technology described herein, even without any forced cooling or implementing any thermal mass reductions described elsewhere herein.

Manufacturing Process for Cartridge

Figure 24:
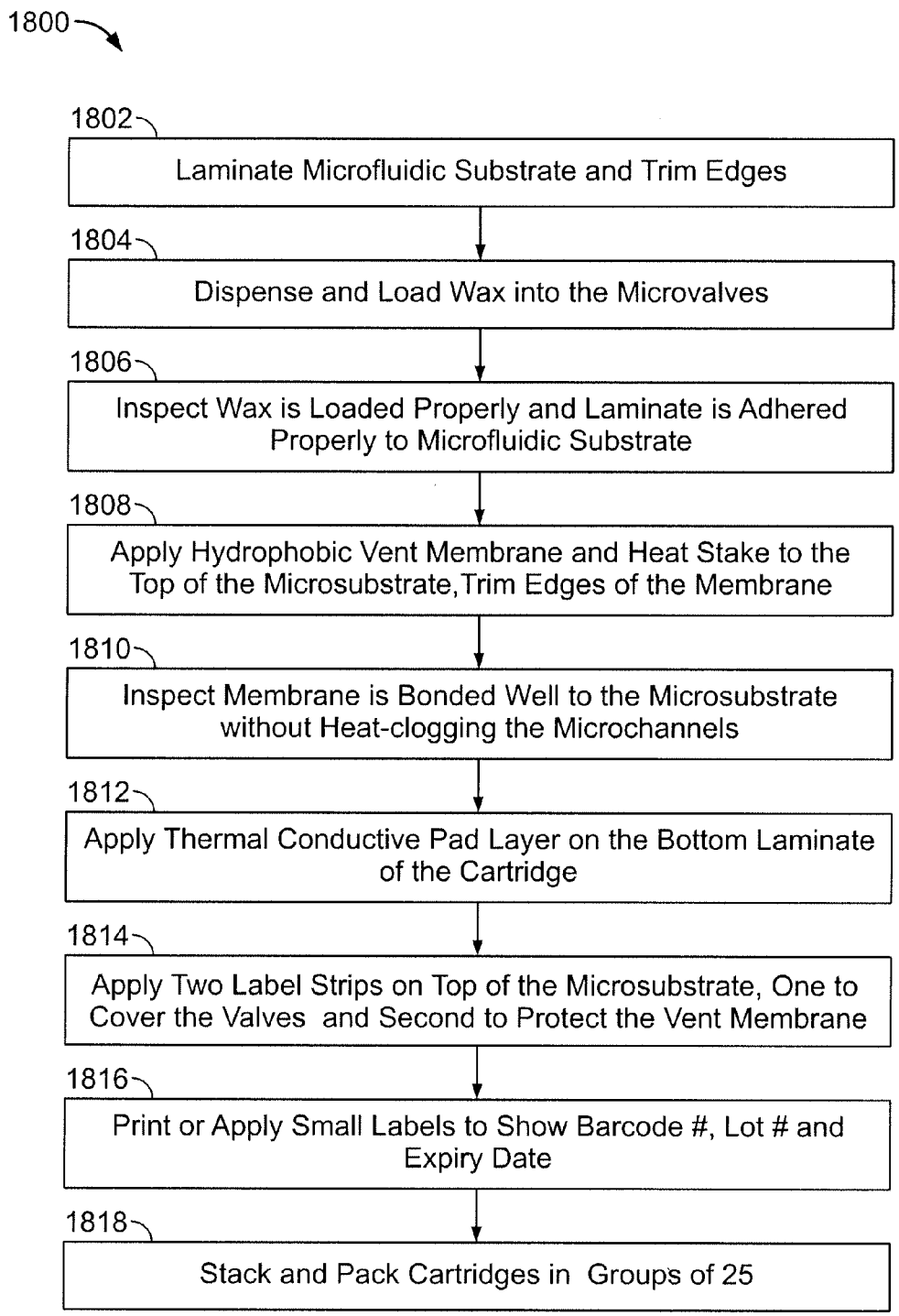
FIG. 24 shows an assembly process for a cartridge as further described herein.

FIG. 24 shows a flow-chart 1800 for an embodiment of an assembly process for an exemplary cartridge as shown in FIG. 11A herein. It would be understood by one of ordinary skill in the art, both that various steps may be performed in a different order from the order set forth in FIG. 24, and additionally that any given step may be carried out by alternative methods to those described in the figure. It would also be understood that, where separate serial steps are illustrated for carrying out two or more functions, such functions may be performed synchronously and combined into single steps and remain consistent with the overall process described herein.

At 1802, a laminate layer is applied to a microfluidic substrate that has previously been engineered, for example by injection molding, to have a microfluidic network constructed in it; edges are trimmed from the laminate where they spill over the bounds of the substrate.

At 1804, wax is dispensed and loaded into the microvalves of the microfluidic network in the microfluidic substrate. An exemplary process for carrying this out is further described herein.

At 1806, the substrate is inspected to ensure that wax from step 1804 is loaded properly and that the laminate from step 1802 adheres properly to it. If a substrate does not satisfy either or both of these tests, it is usually discarded. If substrates repeatedly fail either or both of these tests, then the wax dispensing, or laminate application steps, as applicable, are reviewed.

At 1808, a hydrophobic vent membrane is applied to, and heat bonded to, the top of the microfluidic substrate covering at least the one or more vent holes, and on the opposite face of the substrate from the laminate. Edges of the membrane that are in excess of the boundary of the substrate are trimmed.

At 1810, the assembly is inspected to ensure that the hydrophobic vent membrane is bonded well to the microfluidic substrate without heat-clogging the microfluidic channels. If any of the channels is blocked, or if the bond between the membrane and the substrate is imperfect, the assembly is discarded, and, in the case of repeated discard events, the foregoing process step 1808 is reviewed.

At 1812, optionally, a thermally conductive pad layer is applied to the bottom laminate of the cartridge.

At 1814, two label strips are applied to the top of the microfluidic substrate, one to cover the valves, and a second to protect the vent membranes. It would be understood that a single label strip may be devised to fulfill both of these roles.

At 1816, additional labels are printed or applied to show identifying characteristics, such as a barcode #, lot # and expiry date on the cartridge. Preferably one or more of these labels has a space and a writable surface that permits a user to make an identifying annotation on the label, by hand.

Optionally, at 1818, to facilitate transport and delivery to a customer, assembled and labeled cartridges are stacked, and cartridges packed into groups, such as groups of 25, or groups of 10, or groups of 20, or groups of 48 or 50. Preferably the packaging is via an inert and/or moisture-free medium.

Wax Loading in Valves

Figure 25A:
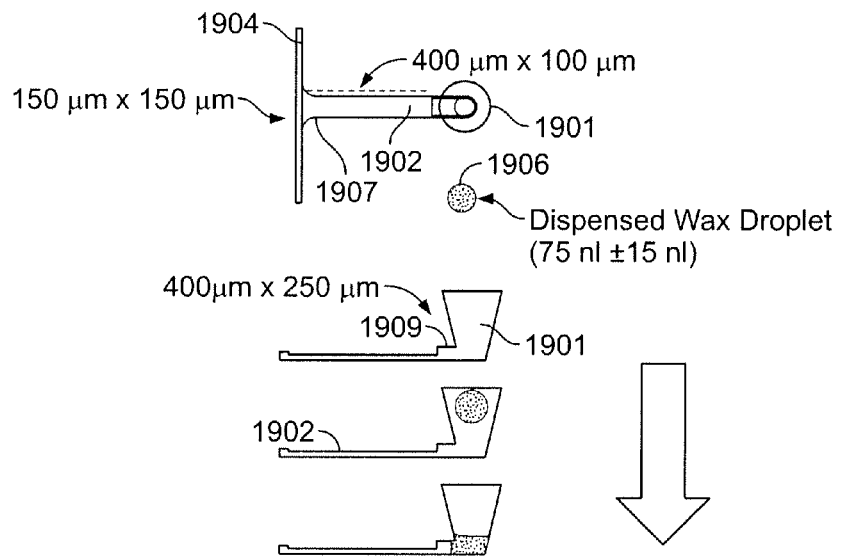
FIGS. 25A and 25B show exemplary deposition of wax droplets into microfluidic valves.
Figure 25B:
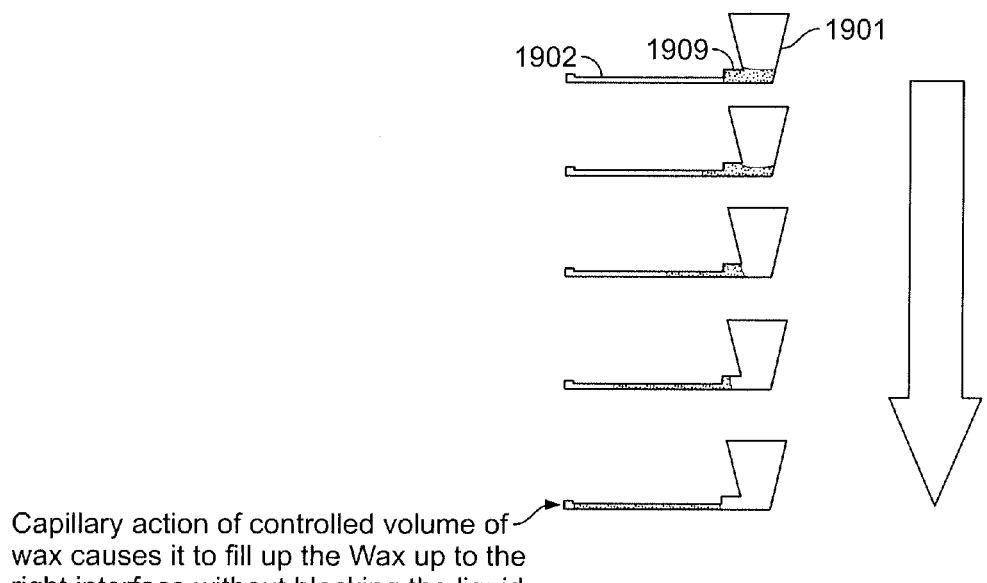

In general, a valve as shown in, e.g., FIGS. 25A-C, is constructed by depositing a precisely controlled amount of a TRS (such as wax) into a loading inlet machined in the microfluidic substrate. FIGS. 25A and 25B show how a combination of controlled hot drop dispensing into a heated microchannel device of the right dimensions and geometry is used to accurately load wax into a microchannel of a microfluidic cartridge to form a valve. The top of FIG. 25A shows a plan view of a valve inlet 190 and loading channel 1902, connecting to a flow channel 1904. The lower portions of FIG. 25A show the progression of a dispensed wax droplet 1906 (having a volume of 75 nl±15 nl) through the inlet 1901 and into the loading channel 1902.

To accomplish those steps, a heated dispenser head can be accurately positioned over the inlet hole of the micro channel in the microfluidic device, and can dispense molten wax drops in volumes as small as 75 nanoliters with an accuracy of 20%. A suitable dispenser is also one that can deposit amounts smaller than 100 nl with a precision of +/−20%. The dispenser should also be capable of heating and maintaining the dispensing temperature of the TRS to be dispensed. For example, it may have a reservoir to hold the solution of TRS. It is also desirable that the dispense head can have freedom of movement at least in a horizontal (x-y) plane so that it can easily move to various locations of a microfluidic substrate and dispense volumes of TRS into valve inlets at such locations without having to be re-set, repositioned manually, or recalibrated in between each dispense operation.

The inlet hole of the microfluidic cartridge, or other microchannel device, is dimensioned in such a way that the droplet of 75 nl can be accurately propelled to the bottom of the inlet hole using, for example, compressed air, or in a manner similar to an inkjet printing method. The microfluidic cartridge is maintained at a temperature above the melting point of the wax thereby permitting the wax to stay in a molten state immediately after it is dispensed. After the drop falls to the bottom of the inlet hole 1901, the molten wax is drawn into the narrow channel by capillary action, as shown in the sequence of views in FIG. 25B. A shoulder between the inlet hole 1901 and the loading channel can facilitate motion of the TRS. The volume of the narrow section can be designed to be approximately equal to a maximum typical amount that is dispensed into the inlet hole. The narrow section can also be designed so that even though the wax dispensed may vary considerably between a minimum and a maximum shot size, the wax always fills up to, and stops at, the micro channel junction 1907 because the T-junction provides a higher cross section than that of the narrow section and thus reduces the capillary forces.

PCR Reagent Mixtures

In various embodiments, the sample for introduction into a lane of the microfluidic cartridge can include a PCR reagent mixture comprising a polymerase enzyme and a plurality of nucleotides.

In various embodiments, preparation of a PCR-ready sample for use with an apparatus and cartridge as described herein can include contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid).

The PCR-ready sample can be prepared, for example, using the following steps: (1) collect sample in sample collection buffer, (2) transfer entire sample to lysis tube, mix, heat, and incubate for seven minutes, (3) place on magnetic rack, allow beads to separate, aspirate supernatant, (4) add 100 µl of Buffer 1, mix, place on magnetic rack, allow beads to separate, aspirate supernatant, (5) add 10 µl of Buffer 2, mix, place in high temperature heat block for 3 minutes, place on magnetic rack, allow beads to separate, transfer 5 µl supernatant, and (6) Add 5 µl of Buffer 3, transfer 1 to 10 µl of supernatant for PCR amplification and detection.

The PCR reagent mixture can be in the form of one or more lyophilized pellets and the steps by which the PCR-ready sample is prepared can involve reconstituting the PCR pellet by contacting it with liquid to create a PCR reagent mixture solution. In yet another embodiment, each of the PCR lanes may have dried down or lyophilized ASR reagents preloaded such that the user only needs to input prepared polynucleotide sample into the PCR. In another embodiment, the PCR lanes may have only the application-specific probes and primers pre-measured and pre-loaded, and the user inputs a sample mixed with the PCR reagents.

In various embodiments, the PCR-ready sample can include at least one probe that can be selective for a polynucleotide sequence, wherein the steps by which the PCR-ready sample is prepared involve contacting the neutralized polynucleotide sample or a PCR amplicon thereof with the probe. The probe can be a fluorogenic hybridization probe. The fluorogenic hybridization probe can include a polynucleotide sequence coupled to a fluorescent reporter dye and a fluorescence quencher dye.

In various embodiments, the PCR-ready sample further includes a sample buffer.

In various embodiments, the PCR-ready sample includes at least one probe that is selective for a polynucleotide sequence, e.g., the polynucleotide sequence that is characteristic of a pathogen selected from the group consisting of gram positive bacteria, gram negative bacteria, yeast, fungi, protozoa, and viruses.

In various embodiments, the PCR reagent mixture can further include a polymerase enzyme, a positive control plasmid and a fluorogenic hybridization probe selective for at least a portion of the plasmid.

In various embodiments, the probe can be selective for a polynucleotide sequence that is characteristic of an organism, for example any organism that employs deoxyribonucleic acid or ribonucleic acid polynucleotides. Thus, the probe can be selective for any organism. Suitable organisms include mammals (including humans), birds, reptiles, amphibians, fish, domesticated animals, wild animals, extinct organisms, bacteria, fungi, viruses, plants, and the like. The probe can also be selective for components of organisms that employ their own polynucleotides, for example mitochondria. In some embodiments, the probe is selective for microorganisms, for example, organisms used in food production (for example, yeasts employed in fermented products, molds or bacteria employed in cheeses, and the like) or pathogens (e.g., of humans, domesticated or wild mammals, domesticated or wild birds, and the like). In some embodiments, the probe is selective for organisms selected from the group consisting of gram positive bacteria, gram negative bacteria, yeast, fungi, protozoa, and viruses.

In various embodiments, the probe can be selective for a polynucleotide sequence that is characteristic of an organism selected from the group consisting of *Staphylococcus* spp., e.g., *S. epidermidis, S. aureus*, Methicillin-resistant *Staphylococcus aureus* (MRSA), Vancomycin-resistant *Staphylococcus; Streptococcus* (e.g., α, β or γ-hemolytic, Group A, B, C, D or G) such as *S. pyogenes, S. agalactiae; E. faecalis, E. durans*, and *E. faecium* (formerly *S. faecalis, S. durans, S. faecium*); nonenterococcal group D streptococci, e.g., *S. bovis* and *S. equines; Streptococci viridans*, e.g., *S. mutans, S. sanguis, S. salivarius, S. mitior, A. milleri, S. constellatus, S. intermedius*, and *S. anginosus; S. iniae; S. pneumoniae; Neisseria*, e.g., *N. meningitides, N. gonorrhoeae*, saprophytic *Neisseria* sp; *Erysipelothrix*, e.g., *E. rhusiopathiae; Listeria* spp., e.g., *L. monocytogenes*, rarely *L. ivanovii* and *L. seeligeri; Bacillus*, e.g., *B. anthracis, B. cereus, B. subtilis, B. subtilus niger, B. thuringiensis; Nocardia asteroids; Legionella*, e.g., *L. pneumonophilia, Pneumocystis*, e.g., *P. carinii;* Enterobacteriaceae such as *Salmonella, Shigella, Escherichia* (e.g., *E. coli, E. coli*O157:H7); *Klebsiella, Enterobacter, Serratia, Proteus, Morganella, Providencia, Yersinia*, and the like, e.g., *Salmonella*, e.g., *S. typhi S. paratyphi* A, B (*S. schottmuelleri*), and C (*S. hirschfeldii*), *S. dublin S. choleraesuis, S. enteritidis, S. typhimurium, S. heidelberg, S. newport, S. infantis, S. agona, S. montevideo*, and *S. saint-paul; Shigella* e.g., subgroups: A, B, C, and D, such as *S. flexneri, S. sonnei, S. boydii, S. dysenteriae; Proteus* (*P. mirabilis, P. vulgaris*, and *P. myxofaciens*), *Morganella* (*M. morganii*); *Providencia* (*P. rettgeri, P. alcalifaciens*, and *P. stuartii*); *Yersinia*, e.g., *Y. pestis, Y. enterocolitica; Haemophilus*, e.g., *H. influenzae, H. parainfluenzae H. aphrophilus, H. ducreyi; Brucella*, e.g., *B. abortus, B. melitensis, B. suis, B. canis; Francisella*, e.g., *F. tularensis; Pseudomonas*, e.g., *P. aeruginosa, P. paucimobilis, P. putida, P. fluorescens, P. acidovorans, Burkholderia* (*Pseudomonas*) *pseudomallei, Burkholderia mallei, Burkholderia cepacia* and *Stenotrophomonas maltophilia; Campylobacter*, e.g., *C. fetus fetus, C. jejuni, C. pylori* (*Helicobacter pylori*); *Vibrio*, e.g., *V. cholerae, V. parahaemolyticus, V. mimicus, V. alginolyticus, V. hollisae, V. vulnificus*, and the nonagglutinable vibrios; *Clostridia*, e.g., *C. perfringens, C. tetani, C. difficile, C. botulinum; Actinomyces*, e.g., *A. israelii; Bacteroides*, e.g., *B. fragilis, B. thetaiotaomicron, B. distasonis, B. vulgatus, B. ovatus, B. caccae*, and *B. merdae; Prevotella*, e.g., *P. melaminogenica;* genus *Fusobacterium; Treponema*, e.g. *T. pallidum* subspecies *endemicum, T. pallidum* subspecies *pertenue, T. carateum*, and *T. pallidum* subspecies *pallidum;* genus *Borrelia*, e.g., *B burgdorferi;* genus *Leptospira; Streptobacillus*, e.g., *S. moniliformis; Spirillum*, e.g., *S. minus; Mycobacterium*, e.g., *M. tuberculosis, M. bovis, M. africanum, M. avium M. intracellulare, M. kansasii, M. xenopi, M. marinum, M. ulcerans*, the *M. fortuitum* complex (*M. fortuitum* and *M. chelonei*), *M. leprae, M. asiaticum, M. chelonei* subsp. *abscessus, M. fallax, M. fortuitum, M. malmoense, M. shimoidei, M. simiae, M. szulgai, M. xenopi; Mycoplasma*, e.g., *M. hominis, M. orale, M. salivarium, M. fermentans, M. pneumoniae, M. bovis, M. tuberculosis, M. avium, M. leprae; Mycoplasma*, e.g., *M. genitalium; Ureaplasma*, e.g., *U. urealyticum; Trichomonas*, e.g., *T. vaginalis; Cryptococcus*, e.g., *C. neoformans; Histoplasma*, e.g., *H. capsulatum; Candida*, e.g., *C. albicans; Aspergillus* sp; *Coccidioides*, e.g., *C. immitis; Blastomyces*, e.g. *B. dermatitidis; Paracoccidioides*, e.g., *P. brasiliensis; Penicillium*, e.g., *P. marneffei; Sporothrix*, e.g., *S. schenckii; Rhizopus, Rhizomucor, Absidia*, and *Basidiobolus;* diseases caused by *Bipolaris, Cladophialophora, Cladosporium, Drechslera, Exophiala, Fonsecaea, Phialophora, Xylohypha, Ochroconis, Rhinocladiella, Scolecobasidium*, and *Wangiella; Trichosporon*, e.g., *T. beigelii; Blastoschizomyces*, e.g., *B. capitatus; Plasmodium*, e.g., *P. falciparum, P. vivax, P. ovale*, and *P. malariae; Babesia* sp; protozoa of the genus *Trypanosoma*, e.g., *T. cruzi; Leishmania*, e.g., *L. donovani, L. major L. tropica, L. mexicana, L. braziliensis, L. viannia braziliensis; Toxoplasma*, e.g., *T. gondii;* Amoebas of the genera *Naegleria* or *Acanthamoeba; Entamoeba histolytica; Giardia lamblia;* genus *Cryptosporidium*, e.g., *C. parvum; Isospora belli; Cyclospora cayetanensis; Ascaris lumbricoides; Trichuris trichiura; Ancylostoma duodenale* or *Necator americanus; Strongyloides stercoralis Toxocara*, e.g., *T. canis, T. cati; Baylisascaris*, e.g., *B. procyonis; Trichinella*, e.g., *T. spiralis; Dracunculus*, e.g., *D. medinensis;* genus *Filarioidea; Wuchereria bancrofti; Brugia*, e.g., *B. malayi*, or *B. timori; Onchocerca volvulus; Loa boa; Dirofilaria immitis;* genus *Schistosoma*, e.g., *S. japonicum, S. mansoni, S. mekongi, S. intercalatum, S. haematobium; Paragonimus*, e.g., *P. Westermani, P. Skriabini; Clonorchis sinensis; Fasciola hepatica; Opisthorchis* sp; *Fasciolopsis buski; Diphyllobothrium latum; Taenia*, e.g., *T. saginata, T. solium; Echinococcus*, e.g., *E. granulosus, E. multilocularis;* Picornaviruses, rhinoviruses echoviruses, coxsackieviruses, influenza virus; paramyxoviruses, e.g., types 1, 2, 3, and 4; adnoviruses; Herpesviruses, e.g., HSV-1 and HSV-2; varicella-zoster virus; human T-lymphotrophic virus (type I and type II); Arboviruses and Arenaviruses; Togaviridae, Flaviviridae, Bunyaviridae, Reoviridae; Flavivirus; Hantavirus; Viral encephalitis (alphaviruses [e.g., Venezuelan equine encephalitis, eastern equine encephalitis, western equine encephalitis]); Viral hemorrhagic fevers (filoviruses [e.g., Ebola, Marburg] and arenaviruses [e.g., Lassa, Machupo]); Smallpox (variola); retroviruses e.g., human immunodeficiency viruses 1 and 2; human papillomavirus [HPV] types 6, 11, 16, 18, 31, 33, and 35.

In various embodiments, the probe can be selective for a polynucleotide sequence that is characteristic of an organisms selected from the group consisting of *Pseudomonas aeruginosa, Proteus mirabilis, Klebsiella oxytoca, Klebsiella pneumoniae, Escherichia coli, Acinetobacter Baumannii, Serratia marcescens, Enterobacter aerogenes, Enterococcus faecium*, vancomycin-resistant *enterococcus* (VRE), *Staphylococcus aureus*, methecillin-resistant *Staphylococcus aureus*(MRSA), *Streptococcus viridans, Listeria monocytogenes, Enterococcus* spp., *Streptococcus* Group B, *Streptococcus* Group C, *Streptococcus* Group G, *Streptococcus* Group F, *Enterococcus faecalis, Streptococcus pneumoniae, Staphylococcus epidermidis, Gardenerella vaginalis, Micrococcus* sps., *Haemophilus influenzae, Neisseria gonorrhoeee, Moraxella catarrahlis, Salmonella* sps., *Chlamydia trachomatis, Peptostreptococcus productus, Peptostreptococcus anaerobius, Lactobacillus fermentum, Eubacterium lentum, Candida glabrata, Candida albicans, Chlamydia* spp., *Camplobacter* spp., *Salmonella* spp., smallpox (variola major), Yersina Pestis, Herpes Simplex Virus I (HSV I), and Herpes Simplex Virus II (HSV II).

In various embodiments, the probe can be selective for a polynucleotide sequence that is characteristic of Group B *Streptococcus*.

In various embodiments, a method of carrying out PCR on a sample can further include one or more of the following steps: heating the biological sample in the microfluidic cartridge; pressurizing the biological sample in the microfluidic cartridge at a pressure differential compared to ambient pressure of between about 20 kilopascals and 200 kilopascals, or in some embodiments, between about 70 kilopascals and 110 kilopascals.

In some embodiments, the method for sampling a polynucleotide can include the steps of: placing a microfluidic cartridge containing a PCR-ready sample in a receiving bay of a suitably configured apparatus; carrying out PCR on the sample under thermal cycling conditions suitable for creating PCR amplicons from the neutralized polynucleotide in the sample, the PCR-ready sample comprising a polymerase enzyme, a positive control plasmid, a fluorogenic hybridization probe selective for at least a portion of the plasmid, and a plurality of nucleotides; contacting the neutralized polynucleotide sample or a PCR amplicon thereof with the at least one fluorogenic probe that is selective for a polynucleotide sequence, wherein the probe is selective for a polynucleotide sequence that is characteristic of an organism selected from the group consisting of gram positive bacteria, gram negative bacteria, yeast, fungi, protozoa, and viruses; and detecting the fluorogenic probe, the presence of the organism for which the one fluorogenic probe is selective is determined.

Carrying out PCR on a PCR-ready sample can additionally include: independently contacting each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; and/or contacting the neutralized polynucleotide sample or a PCR amplicon thereof and the negative control polynucleotide or a PCR amplicon thereof with at least one probe that is selective for a polynucleotide sequence.

In various embodiments, a method of using the apparatus and cartridge described herein can further include one or more of the following steps: determining the presence of a polynucleotide sequence in the biological sample, the polynucleotide sequence corresponding to the probe, if the probe is detected in the neutralized polynucleotide sample or a PCR amplicon thereof; determining that the sample was contaminated if the probe is detected in the negative control polynucleotide or a PCR amplicon thereof; and/or in some embodiments, wherein the PCR reagent mixture further comprises a positive control plasmid and a plasmid probe selective for at least a portion of the plasmid, the method further including determining that a PCR amplification has occurred if the plasmid probe is detected.

Kit

In various embodiments, the microfluidic cartridge as described herein can be provided in the form of a kit, wherein the kit can include a microfluidic cartridge, and a liquid transfer member (such as a syringe or a pipette). In various embodiments, the kit can further include instructions to employ the liquid transfer member to transfer a sample containing extracted nucleic acid from a sample container via a sample inlet to the microfluidic network on the microfluidic cartridge. In some embodiments, the microfluidic cartridge and the liquid transfer member can be sealed in a pouch with an inert gas.

Typically when transferring a sample from liquid dispenser, such as a pipette tip, to an inlet on the microfluidic cartridge, a volume of air is simultaneously introduced into the microfluidic network, the volume of air being between about 0.5 mL and about 5 mL. Presence of air in the microfluidic network, however, is not essential to operation of the cartridge described herein.

In various embodiments, the kit can further include at least one computer-readable label on the cartridge. The label can include, for example, a bar code, a radio frequency tag or one or more computer-readable characters. When used in conjunction with a similar computer-readable label on a sample container, such as a vial or a pouch, matching of diagnostic results with sample is thereby facilitated.

In some embodiments, a sample identifier of the apparatus described elsewhere herein is employed to read a label on the microfluidic cartridge and/or a label on the biological sample.

Heater Unit

Figure 26:
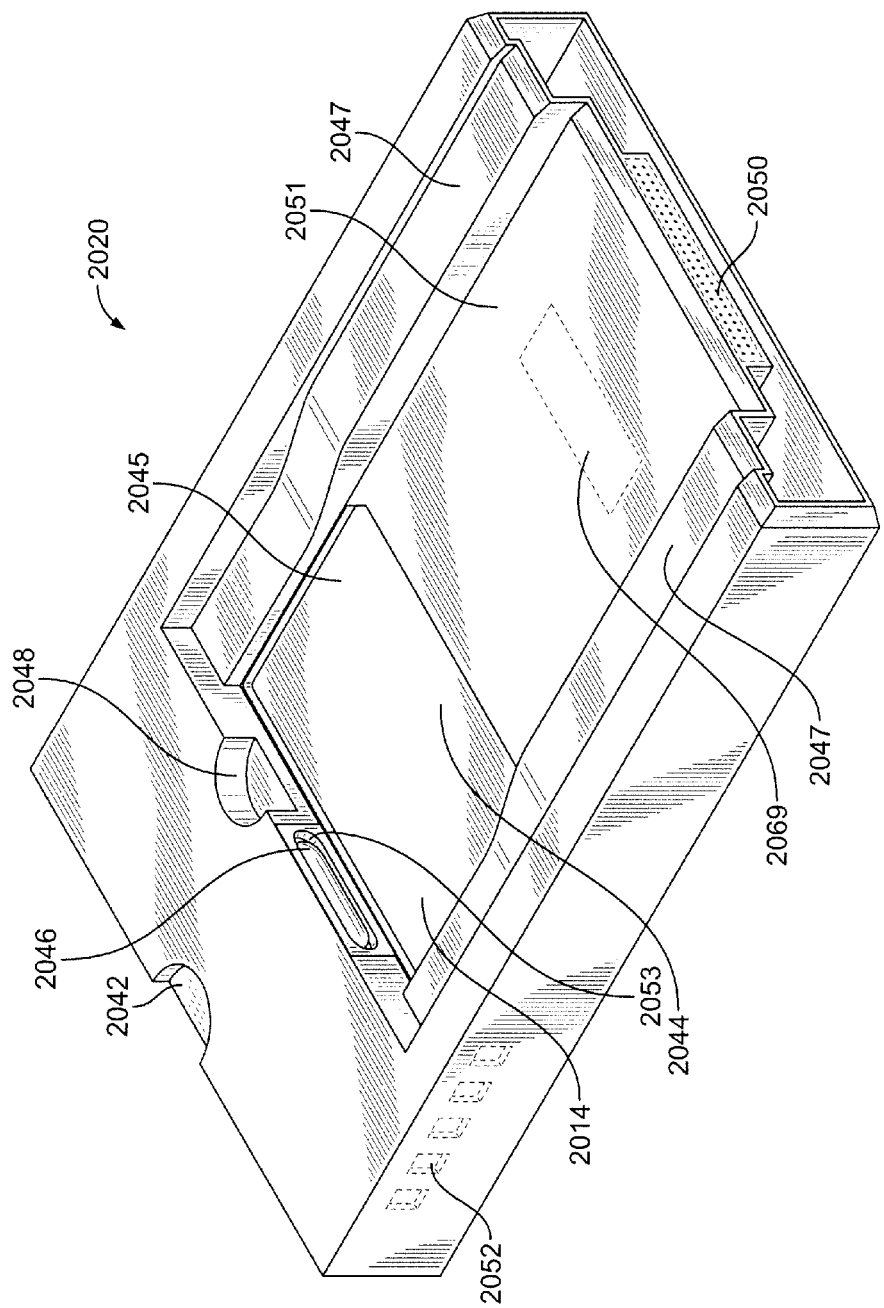
FIG. 26 shows an exemplary heater unit.

An exemplary heater unit 2020 is shown in FIG. 26. The unit is configured to deliver localized heat to various selected regions of a cartridge received in a receiving bay 2014. Heater unit 2020 is configured to be disposed within a diagnostic apparatus during operation, as further described herein, and in certain embodiments is removable from that apparatus, for example to facilitate cleaning, or to permit reconfiguration of the heater circuitry. In various embodiments, heater unit 2020 can be specific to particular designs of microfluidic networks and microfluidic substrate layouts.

Shown in FIG. 26 is a heater unit having a recessed surface 2044 that provides a platform for supporting a microfluidic cartridge when in receiving bay 2014. In one embodiment, the cartridge rests directly on surface 2044. Surface 2044 is shown as recessed, in FIG. 2, but need not be so and, for example, may be raised or may be flush with the surrounding area of the heater unit. Surface 2044 is typically a layer of material that overlies a heater chip or board, or a heater substrate, that contains heater micro-circuitry configured to selectively and specifically heat regions of a microfluidic substrate, such as in a cartridge, in the receiving bay 2014.

Area 2044 is configured to accept a microfluidic cartridge in a single orientation. Therefore area 2044 can be equipped with a registration member such as a mechanical key that prevents a user from placing a cartridge into receiving bay 2014 in the wrong configuration. Shown in FIG. 26 as an exemplary mechanical key 2045 is a diagonally cutout corner of area 2044 into which a complementarily cutoff corner of a microfluidic cartridge fits. Other registration members are consistent with the heater unit described herein, for example, a feature engineered on one or more edges of a cartridge including but not limited to: several, such as two or more, cut-out corners, one or more notches cut into one or more edges of the cartridge; or one or more protrusions fabricated into one or more edges of the cartridge. Alternative registration members include one or more lugs or bumps engineered into an underside of a cartridge, complementary to one or more recessed sockets or holes in surface 2044 (not shown in the embodiment of FIG. 26). Alternative registration members include one or more recessed sockets or holes engineered into an underside of a cartridge, complementary to one or more lugs or bumps on surface 2044. In general, the pattern of features is such that the cartridge possesses at least one element of asymmetry so that it can only be inserted in a single orientation into the receiving bay.

Also shown in FIG. 26 is a hand-grasp 2042 that facilitates removal and insertion of the heater unit into an apparatus by a user. Cutaway 2048 permits a user to easily remove a cartridge from receiving bay 2014 after a processing run where, e.g., a user's thumb or finger when grabbing the top of the cartridge, is afforded comfort space by cutaway 2048. Both cutaways 2042 and 2048 are shown as semicircular recesses in the embodiment of FIG. 26, but it would be understood that they are not so limited in shape. Thus, rectangular, square, triangular, half-oval, contoured, and other shaped recesses are also consistent with a heater unit as described herein.

In the embodiment of FIG. 26, which is designed to be compatible with an exemplary apparatus as further described herein, the front of the heater unit is at the left of the figure. At the rear of heater unit 2020 is an electrical connection 2050, such as an RS-232 connection, that permits electrical signals to be directed to heaters located at specific regions of area 2044 during sample processing and analysis, as further described herein. Thus, underneath area 2044 and not shown in FIG. 2 can be an array of heat sources, such as resistive heaters, that are configured to align with specified locations of a microfluidic cartridge properly inserted into the receiving bay. Surface 2044 is able to be cleaned periodically, for example with common cleaning agents (e.g., a 10% bleach solution), to ensure that any liquid spills that may occur during sample handling do not cause any short circuiting. Such cleaning can be carried out frequently when the heater unit is disposed in a diagnostic apparatus, and less frequently but more thoroughly when the unit is removed.

Other non-essential features of heater unit 2020 are as follows. One or more air vents 2052 can be situated on one or more sides (such as front, rear, or flanking) or faces (such as top or bottom) of heater unit 2020, to permit excess heat to escape, when heaters underneath receiving bay 2014, are in operation. The configuration of air vents in FIG. 26, as a linear array of square vents, is exemplary and it would be understood that other numbers and shapes thereof are consistent with routine fabrication and use of a heater unit. For example, although 5 square air vents are shown, other numbers such as 1, 2, 3, 4, 6, 8, or 10 air vents are possible, arranged on one side, or spread over two or more sides and/or faces of the heater unit. In further embodiments, air vents may be circular, rectangular, oval, triangular, polygonal, and having curved or squared vertices, or still other shapes, including irregular shapes. In further embodiments two or more vents need not be disposed in a line, parallel with one another and with an edge of the heater unit but may be disposed offset from one another.

Heater unit 2020 may further comprise one or more guiding members 2047 that facilitate inserting the heater unit into an apparatus as further described herein, for an embodiment in which heater unit 2020 is removable by a user. Heater unit is advantageously removable because it permits system 2000 to be easily reconfigured for a different type of analysis, such as employing a different cartridge with a different registration member and/or microfluidic network, in conjunction with the same or a different sequence of processing operations. In other embodiments, heater unit 2020 is designed to be fixed and only removable, e.g., for cleaning, replacement, or maintenance, by the manufacturer or an authorized maintenance agent, and not routinely by the user. Guiding members 2047 may perform one or more roles of ensuring that the heater unit is aligned correctly in the apparatus, and ensuring that the heater unit makes a tight fit and does not significantly move during processing and analysis of a sample, or during transport of the apparatus.

Guiding members shown in the embodiment of FIG. 26 are on either side of receiving bay 2044 and stretch along a substantial fraction of the length of unit 2020, but such an arrangement of guiding members is exemplary. Other guiding members are consistent with use herein, and include but are not limited to other numbers of guiding members such as 1, 3, 4, 5, 6, or 8, and other positions thereof, including positioned in area 2051 of unit 2020, and need not stretch along as much of the length of unit 2020 as shown in FIG. 26, or may stretch along its entire length. Guiding members 2047 are shown having a non-constant thickness along their lengths. It is consistent herein that other guiding members may have essentially constant thickness along their lengths. At the end of the heater unit that is inserted into an apparatus, in the embodiment shown, the edges are beveled to facilitate proper placement.

Also shown in FIG. 26 is an optional region of fluorescent material, such as optically fluorescent material 2069, on area 2051 of heater unit 2020. The region of fluorescent material is configured to be detected by a detection system further described herein. The region 2069 is used for verifying the state of optics in the detection system prior to sample processing and analysis and therefore acts as a control, or a standard. For example, in one embodiment a lid of the apparatus in which the heater unit is disposed, when in an open position, permits ambient light to reach region 2069 and thereby cause the fluorescent material to emit a characteristic frequency or spectrum of light that can be measured by the detector for, e.g., standardization or calibration purposes. In another embodiment, instead of relying on ambient light to cause the fluorescent material to fluoresce, light source from the detection system itself, such as one or more LED's, is used to shine on region 2069. The region 2069 is therefore positioned to align with a position of a detector. Region 2069 is shown as rectangular, but may be configured in other shapes such as square, circular, elliptical, triangular, polygonal, and having curved or squared vertices. It is also to be understood that the region 2069 may be situated at other places on the heater unit 2020, according to convenience and in order to be complementary to the detection system deployed.

In particular and not shown in FIG. 26, heater/sensor unit 2020 can include, for example, a multiplexing function in a discrete multiplexing circuit board (MUX board), one or more heaters (e.g., a microheater), one or more temperature sensors (optionally combined together as a single heater/sensor unit with one or more respective microheaters, e.g., as photolithographically fabricated on fused silica substrates). The micro-heaters can provide thermal energy that can actuate various microfluidic components on a suitably positioned microfluidic cartridge. A sensor (e.g., as a resistive temperature detector (RTD)) can enable real time monitoring of the micro-heaters, for example through a feedback based mechanism to allow for rapid and accurate control of the temperature. One or more microheaters can be aligned with corresponding microfluidic components (e.g., valves, pumps, gates, reaction chambers) to be heated on a suitably positioned microfluidic cartridge. A microheater can be designed to be slightly bigger than the corresponding microfluidic component(s) on the microfluidic cartridge so that even though the cartridge may be slightly misaligned, such as off-centered, from the heater, the individual components can be heated effectively.

Heater Configurations to Ensure Uniform Heating of a Region

The microfluidic substrates described herein are configured to accept heat from a contact heat source, such as found in a heater unit described herein. The heater unit typically comprises a heater board or heater chip that is configured to deliver heat to specific regions of the microfluidic substrate, including but not limited to one or more microfluidic components, at specific times. For example, the heat source is configured so that particular heating elements are situated adjacent to specific components of the microfluidic network on the substrate. In certain embodiments, the apparatus uniformly controls the heating of a region of a microfluidic network. In an exemplary embodiment, multiple heaters can be configured to simultaneously and uniformly heat a region, such as the PCR reaction chamber, of the microfluidic substrate. The term heater unit, as used herein, may be used interchangeably to describe either the heater board or an item such as shown in FIG. 26.

Figure 27A:
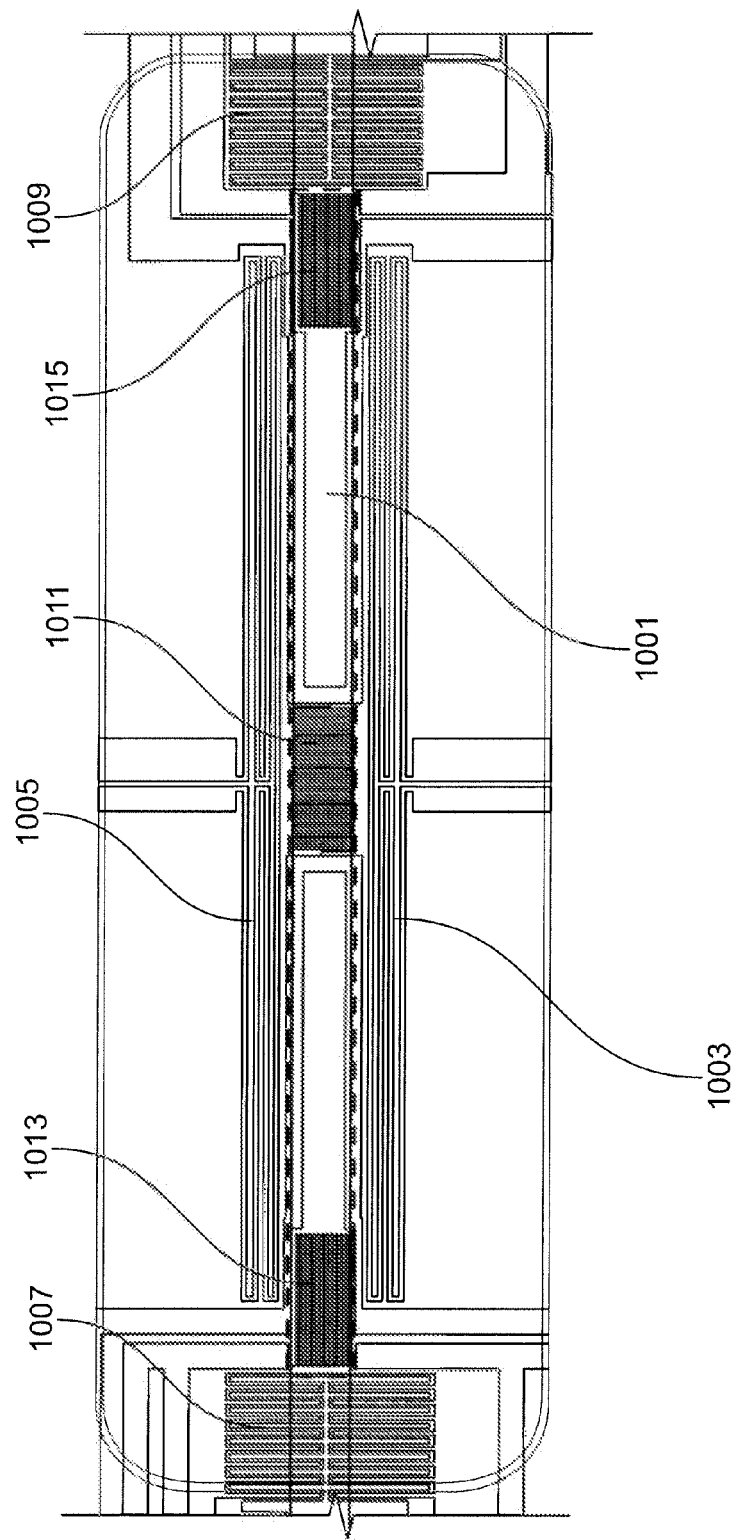
FIGS. 27A and 27B show a plan view of heater circuitry adjacent to a PCR reaction chamber.
Figure 27B:
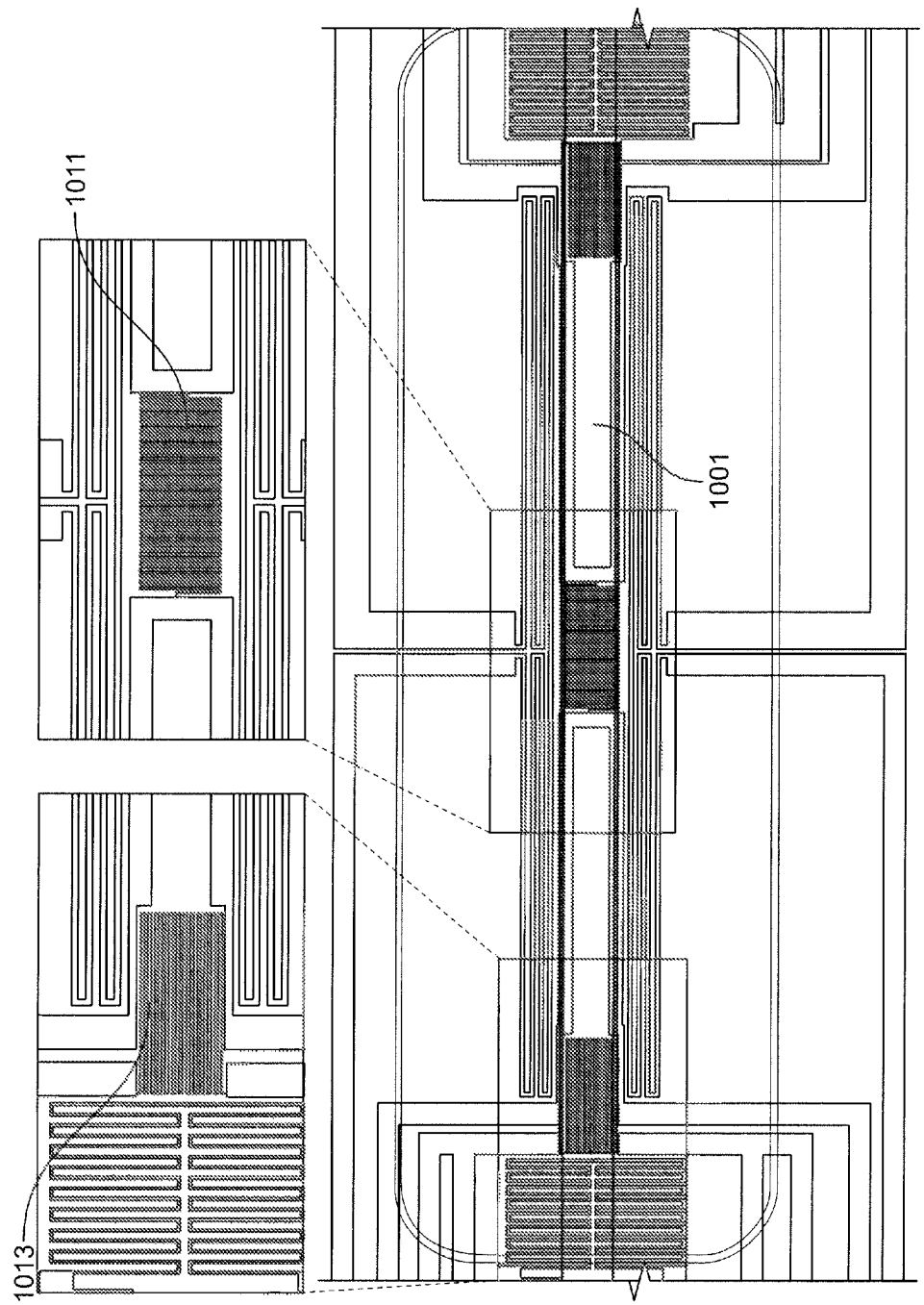

Referring to FIGS. 27A and 27B, an exemplary set of heaters configured to heat, cyclically, PCR reaction chamber 1001 is shown. It is to be understood that heater configurations to actuate other regions of a microfluidic cartridge such as other gates, valves, and actuators, may be designed and deployed according to similar principles to those governing the heaters shown in FIGS. 27A and 27B.

Referring to FIGS. 27A and 27B, an exemplary PCR reaction chamber 1001 in a microfluidic substrate, typically a chamber or channel having a volume ~1.6 µl, is configured with a long side and a short side, each with an associated heating element. A PCR reaction chamber may also be referred to as a PCR reactor, herein, and the region of a cartridge in which the reaction chamber is situated may be called a zone. The heater substrate therefore includes four heaters disposed along the sides of, and configured to heat, a given PCR reaction chamber, as shown in the exemplary embodiment of FIG. 27A: long top heater 1005, long bottom heater 1003, short left heater 1007, and short right heater 1009. The small gap between long top heater 1005 and long bottom heater 1003 results in a negligible temperature gradient (less than 1° C. difference across the width of the PCR channel at any point along the length of the PCR reaction chamber) and therefore an effectively uniform temperature throughout the PCR reaction chamber. The heaters on the short edges of the PCR reactor provide heat to counteract the gradient created by the two long heaters from the center of the reactor to the edge of the reactor.

It would be understood by one of ordinary skill in the art that still other configurations of one or more heater(s) situated about a PCR reaction chamber are consistent with the methods and apparatus described herein. For example, a 'long' side of the reaction chamber can be configured to be heated by two or more heaters. Specific orientations and configurations of heaters are used to create uniform zones of heating even on substrates having poor thermal conductivity because the poor thermal conductivity of glass, or quartz, polyimide, FR4, ceramic, or fused silica substrates is utilized to help in the independent operation of various microfluidic components such as valves and independent operation of the various PCR lanes. It would be further understood by one of ordinary skill in the art, that the principles underlying the configuration of heaters around a PCR reaction chamber are similarly applicable to the arrangement of heaters adjacent to other components of the microfluidic cartridge, such as actuators, valves, and gates.

Generally, the heating of microfluidic components, such as a PCR reaction chamber, is controlled by passing currents through suitably configured microfabricated heaters. Under control of suitable circuitry, the lanes of a multi-lane cartridge can then be controlled independently of one another. This can lead to a greater energy efficiency of the apparatus, because not all heaters are heating at the same time, and a given heater is receiving current for only that fraction of the time when it is required to heat. Control systems and methods of controllably heating various heating elements are further described in U.S. patent application Ser. No. 11/940,315, filed Nov. 14, 2007 and entitled "Heater Unit for Microfluidic Diagnostic System".

In certain embodiments, each heater has an associated temperature sensor. In the embodiment of FIG. 27A, a single temperature sensor 1011 is used for both long heaters. A temperature sensor 1013 for short left heater, and a temperature sensor 1015 for short right heater are also shown. The temperature sensor in the middle of the reactor is used to provide feedback and control the amount of power supplied to the two long heaters, whereas each of the short heaters has a dedicated temperature sensor placed adjacent to it in order to control it. As further described herein, temperature sensors are preferably configured to transmit information about temperature in their vicinity to a processor in the apparatus at such times as the heaters are not receiving current that causes them to heat. This can be achieved with appropriate control of current cycles.

In order to reduce the number of sensor or heater elements required to control a PCR heater, the heaters may be used to sense as well as heat, and thereby obviate the need to have a separate dedicated sensor for each heater. In another embodiment, each of the four heaters may be designed to have an appropriate wattage, and connect the four heaters in series or in parallel to reduce the number of electronically-controllable elements from four to just one, thereby reducing the burden on the associated electronic circuitry.

FIG. 27B shows expanded views of heaters and temperature sensors used in conjunction with a PCR reaction chamber of FIG. 27A. Temperature sensors 1001 and 1013 are designed to have a room temperature resistance of approximately 200-300 ohms. This value of resistance is determined by controlling the thickness of the metal layer deposited (e.g., a sandwich of 400 Å TiW/3,000Å Au/400 Å TiW), and etching the winding metal line to have a width of approximately 10-25 µm and 20-40 mm length. The use of metal in this layer gives it a temperature coefficient of resistivity of the order of 0.5-20° C./ohms, preferably in the range of 1.5-3° C./ohms. Measuring the resistance at higher temperatures enables determination of the exact temperature of the location of these sensors.

The configuration for uniform heating, shown in FIG. 27A for a single PCR reaction chamber, can also be applied to a multi-lane PCR cartridge in which multiple independent PCR reactions occur.

Figure 27C:
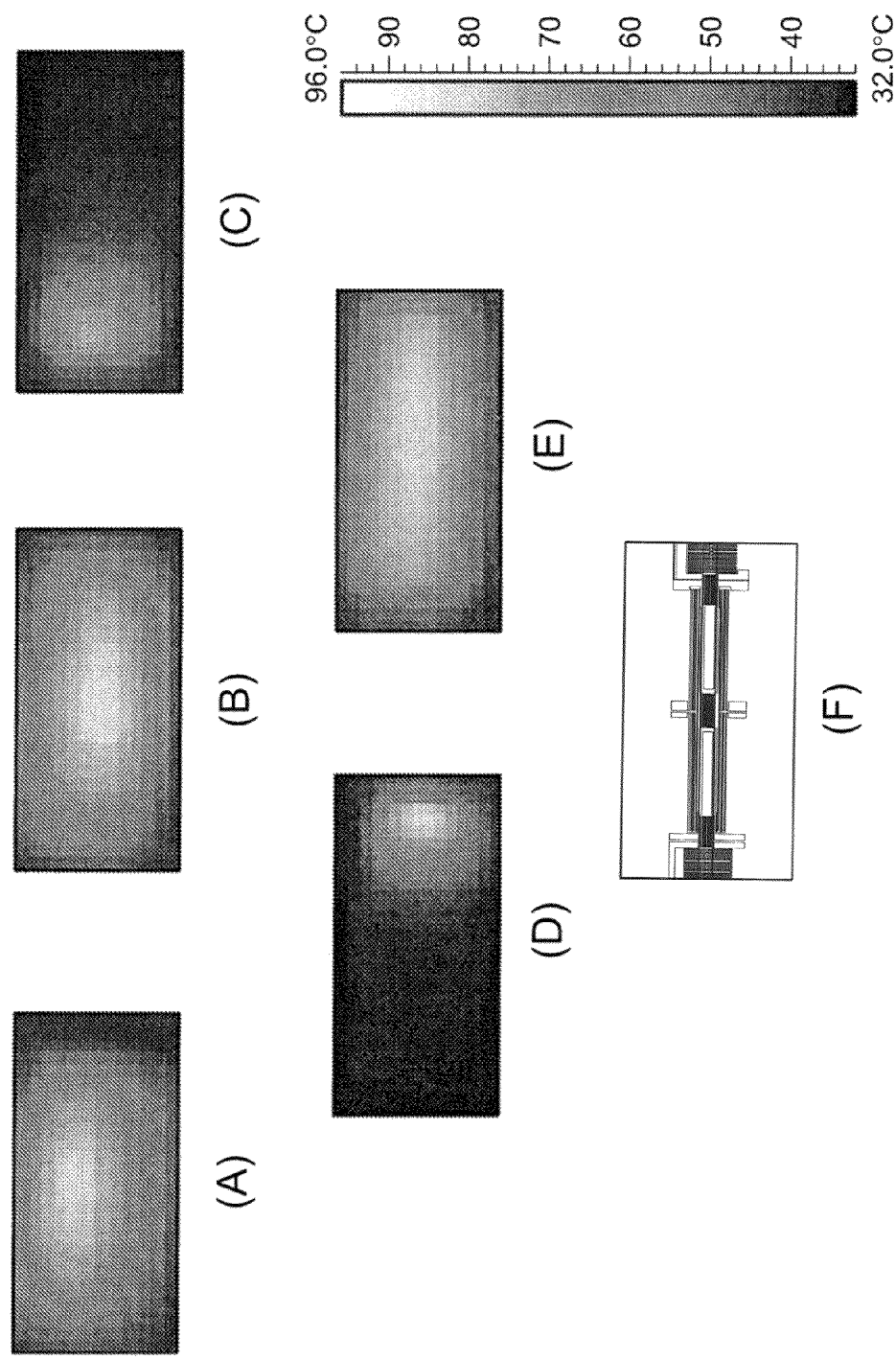
FIG. 27C shows thermal images of heater circuitry in operation.

Each heater can be independently controlled by a processor and/or control circuitry used in conjunction with the apparatus described herein. FIG. 27C shows thermal images, from the top surface of a microfluidic cartridge when heated by heaters configured as in FIGS. 27A and 27B, when each heater in turn is activated, as follows: (A): Long Top only; (B) Long Bottom only; (C) Short Left only; (D) Short Right only; and (E) All Four Heaters on. Panel (F) shows a view of the reaction chamber and heaters on the same scale as the other image panels in FIG. 27C. Also shown in the figure is a temperature bar.

The configuration for uniform heating, shown in FIG. 27A for a single PCR reaction chamber, can be applied to a multi-lane PCR cartridge in which multiple independent PCR reactions occur. See, e.g., FIG. 28, which shows an array of heater elements suitable to heat a cartridge herein.

Heater Multiplexing (Under Software Control)

Another aspect of the heater unit described herein, relates to a control of heat within the system and its components. The method leads to a greater energy efficiency of the apparatus described herein, because not all heaters are heating at the same time, and a given heater is receiving current for only part of the time.

Generally, the heating of microfluidic components, such as a PCR reaction chamber, is controlled by passing currents through suitably configured microfabricated heaters. The heating can be further controlled by periodically turning the current on and off with varying pulse width modulation (PWM), wherein pulse width modulation refers to the on-time/off-time ratio for the current. The current can be supplied by connecting a microfabricated heater to a high voltage source (for example, 30 V), which can be gated by the PWM signal. In some embodiments, the device includes 48 PWM signal generators. Operation of a PWM generator includes generating a signal with a chosen, programmable, period (the end count) and a particular granularity. For instance, the signal can be 4000 μs (micro-seconds) with a granularity of 1 μs, in which case the PWM generator can maintain a counter beginning at zero and advancing in increments of 1 μs until it reaches 4000 μs, when it returns to zero. Thus, the amount of heat produced can be adjusted by adjusting the end count. A high end count corresponds to a greater length of time during which the microfabricated heater receives current and therefore a greater amount of heat produced. It would be understood that the granularity and signal width can take values other than those provided here without departing from the principles described herein.

Fluorescence Detection System, Including Lenses and Filters, and Multiple Parallel Detection for a Multi-Lane Cartridge The detection system herein is configured to monitor fluorescence coming from one or more species involved in a biochemical reaction. The system can be, for example, an optical detector having a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof, as further described elsewhere herein. Alternatively, the optical detector can include a bandpass-filtered diode that selectively emits light in the absorption band of the fluorescent dye and a bandpass filtered photodiode that selectively detects light in the emission band of the fluorescent dye. For example, the optical detector can be configured to independently detect a plurality of fluorescent dyes having different fluorescent emission spectra, wherein each fluorescent dye corresponds to a fluorescent polynucleotide probe or a fragment thereof. For example, the optical detector can be configured to independently detect a plurality of fluorescent dyes at a plurality of different locations of, for example, a microfluidic substrate, wherein each fluorescent dye corresponds to a fluorescent polynucleotide probe or a fragment thereof. The detector further has potential for 2, 3 or 4 color detection and is controlled by software, preferably custom software, configured to sample information from the detector.

The detection system described herein is capable of detecting a fluorescence signal from nanoliter scale PCR reactions. Advantageously, the detector is formed from inexpensive components, having no moving parts. The detector can be configured to couple to a microfluidic cartridge as further described herein, and can also be part of a pressure application system, such as a sliding lid on an apparatus in which the detector is situated, that keeps the cartridge in place.

Figure 31A:
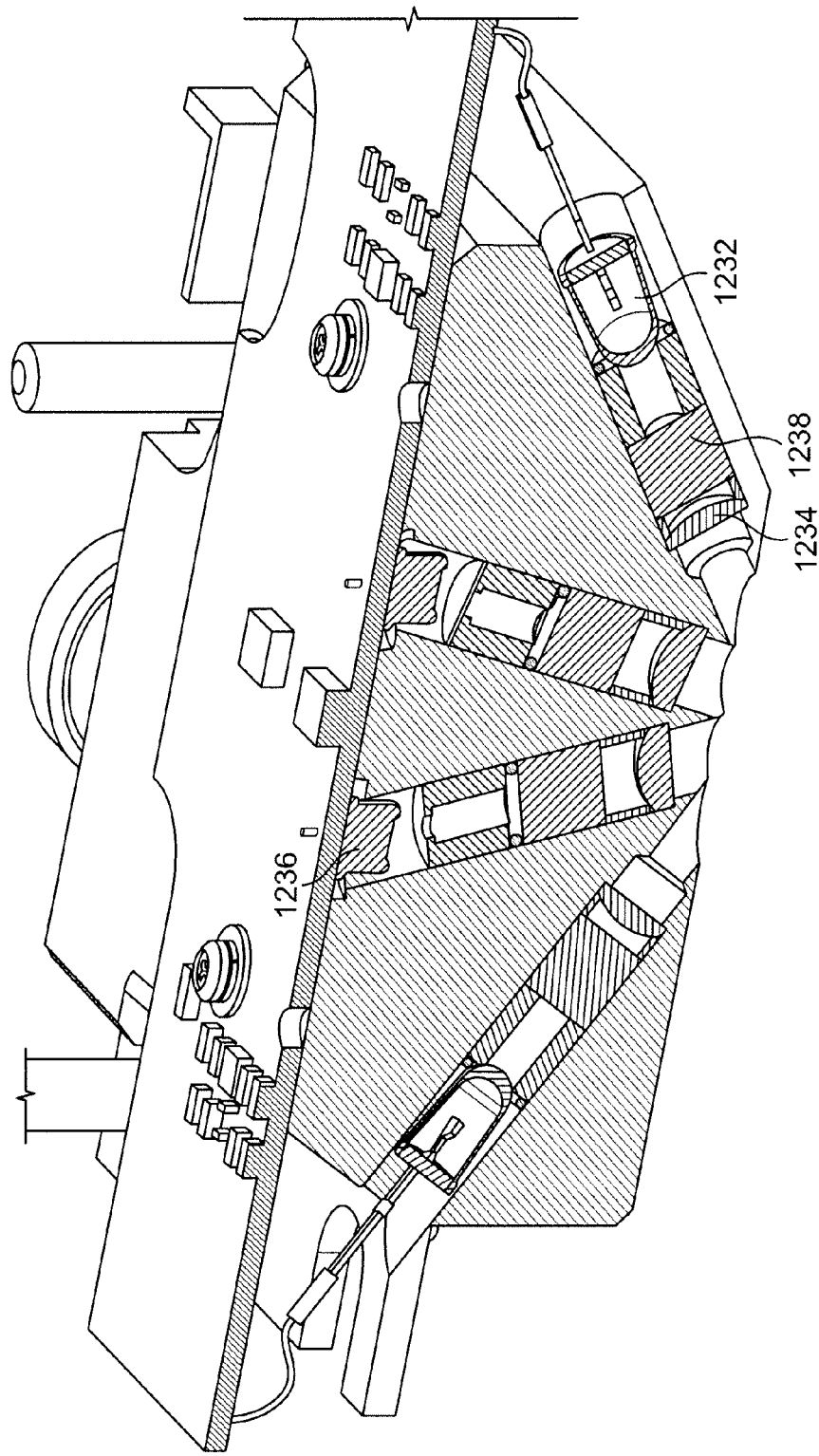
FIG. 31A, 31B shows a cutaway view of an exemplary detector in a read-head.
Figure 31B:
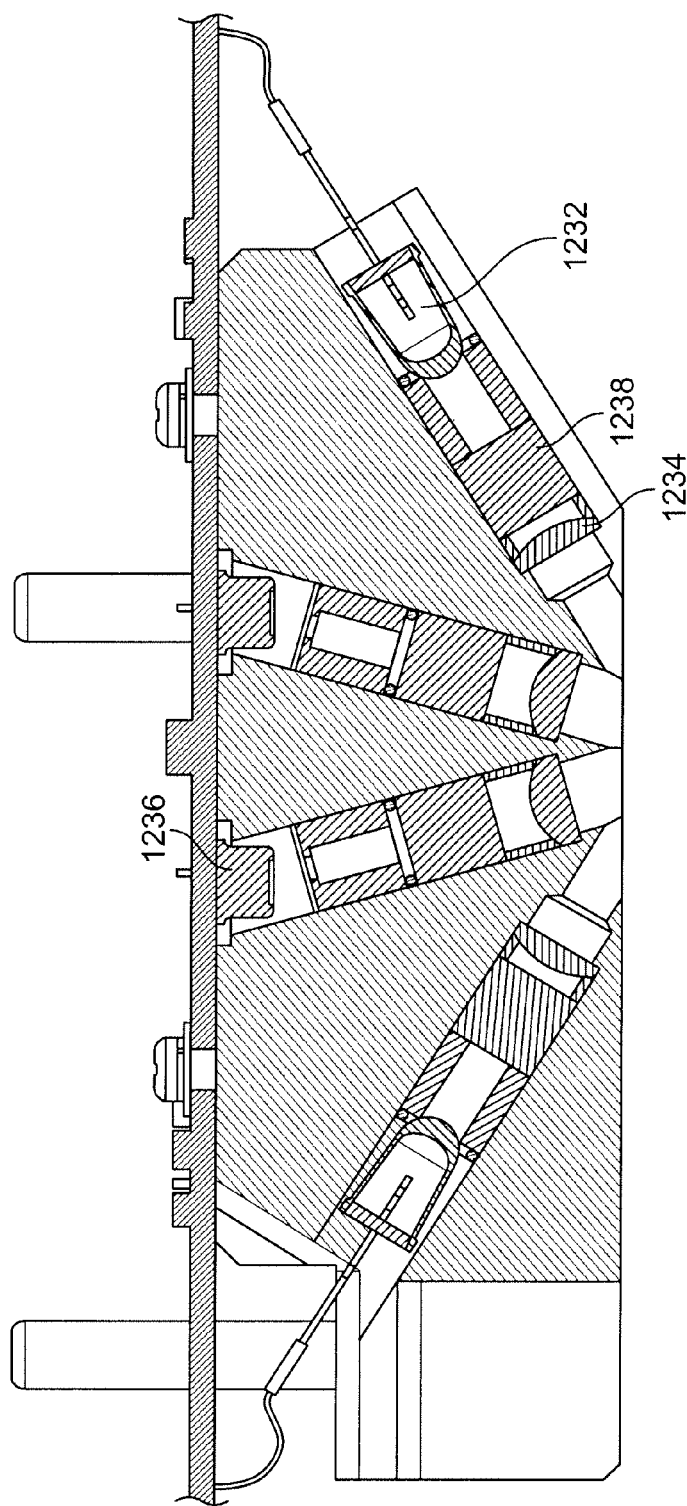

FIGS. 29-31B depict an embodiment of a highly sensitive fluorescence detection system that includes light emitting diodes (LED's), photodiodes, and filters/lenses for monitoring, in real-time, one or more fluorescent signals emanating from the microfluidic channel. The embodiment in FIGS. 29-31B displays a two-color detection system having a modular design that couples with a single microfluidic channel found, for example, in a microfluidic cartridge. It would be understood by one skilled in the art that the description herein could also be adapted to create a detector that just detects a single color of light. FIGS. 31A and 31B show elements of optical detector elements 1220 including light sources 1232 (for example, light emitting diodes), lenses 1234, light detectors 1236 (for example, photodiodes) and filters 1238. The detector comprises two LED's (blue and red, respectively) and two photodiodes. The two LED's are configured to transmit a beam of focused light on to a particular region of the cartridge. The two photo diodes are configured to receive light that is emitted from the region of the cartridge. One photodiode is configured to detect emitted red light, and the other photodiode is configured to detect emitted blue light. Thus, in this embodiment, two colors can be detected simultaneously from a single location. Such a detection system can be configured to receive light from multiple microfluidic channels by being mounted on an assembly that permits it to slide over and across the multiple channels. The filters can be, for example, bandpass filters, the filters at the light sources corresponding to the absorption band of one or more fluorogenic probes and the filters at the detectors corresponding to the emission band of the fluorogenic probes.

Figure 32:
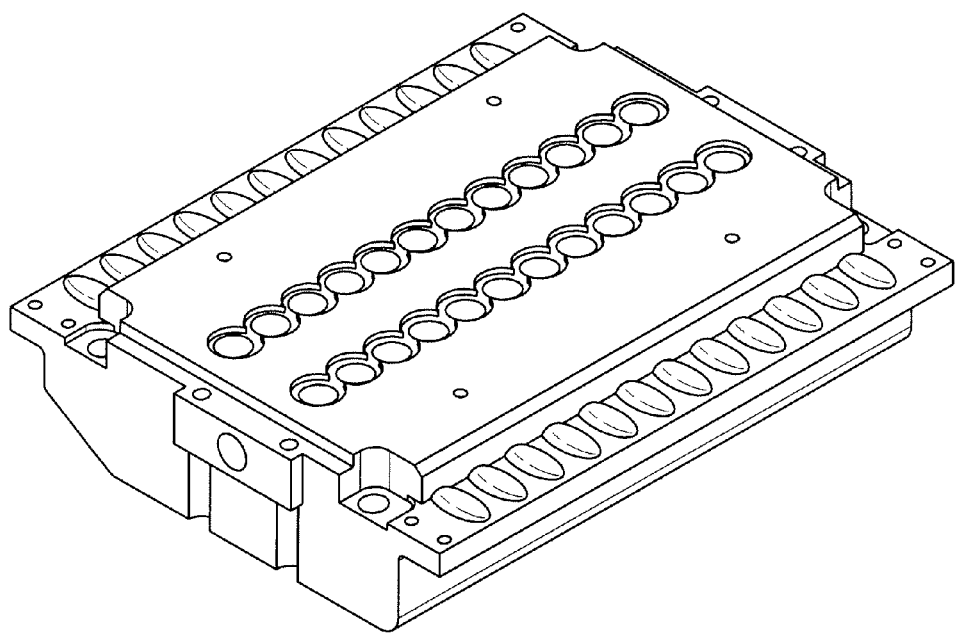
FIG. 32 shows an exterior view of an exemplary multiplexed read-head with an array of detectors therein.
Figure 33:
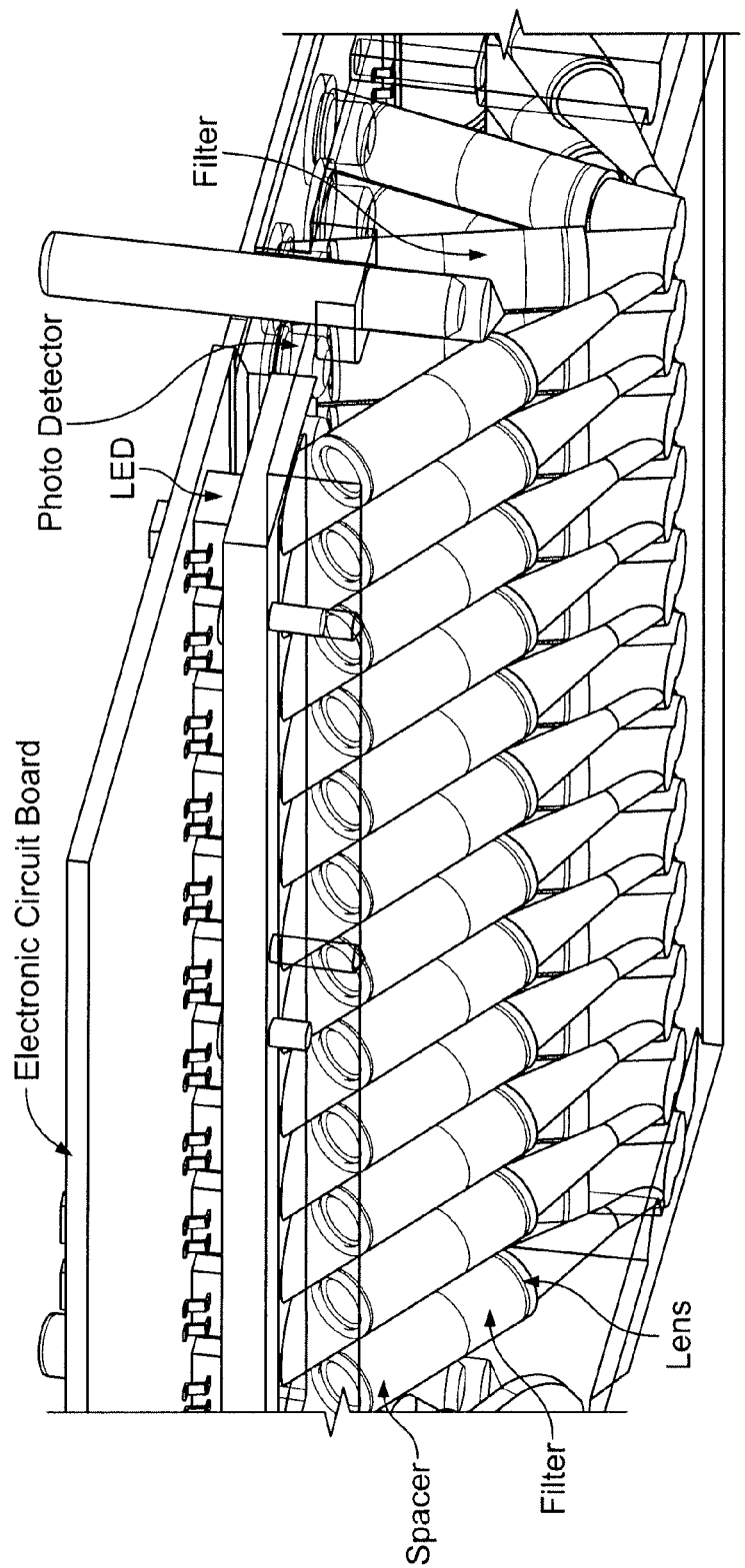
FIG. 33 shows a cutaway view of an exemplary multiplexed read-head, as in FIG. 18.

FIGS. 32 and 33 show an exemplary read-head comprising a multiplexed 2 color detection system that is configured to mate with a multi-lane microfluidic cartridge. FIG. 32 shows a view of the exterior of a multiplexed read-head. FIG. 33 is an exploded view that shows how various detectors are configured within an exemplary multiplexed read head, and in communication with an electronic circuit board.

Each of the detection systems multiplexed in the assembly of FIGS. 32 and 33 is similar in construction to the embodiment of FIGS. 29-31B. The module in FIGS. 32 and 33 is configured to detect fluorescence from each of 12 microfluidic channels, as found in, for example, the respective lanes of a 12-lane microfluidic cartridge. Such a module therefore comprises 24 independently controllable detectors, arranged as 12 pairs of identical detection elements. Each pair of elements is then capable of dual-color detection of a pre-determined set of fluorescent probes. It would be understood by one of ordinary skill in the art that other numbers of pairs of detectors are consistent with the apparatus described herein. For example, 4, 6, 8, 10, 16, 20, 24, 25, 30, 32, 36, 40, and 48 pairs are also consistent and can be configured according to methods and criteria understood by one of ordinary skill in the art.

Detection Sensitivity, Time Constant and Gain

A typical circuit that includes a detector as described herein includes, in series, a preamplifier, a buffer/inverter, a filter, and a digitizer. Sensitivity is important so that high gain is very desirable. In one embodiment of the preamplifier, a very large, for example 100 GΩ, resistor is placed in parallel with the diode. Other values of a resistor would be consistent with the technology herein: such values typically fall in the range 0.5-100 GΩ, such as 1-50 GΩ, or 2-10 GΩ. An exemplary pre-amplifier circuit configured in this way is shown in FIG. 7. Symbols in the figure have their standard meanings in electronic circuit diagrams.

Figure 34:
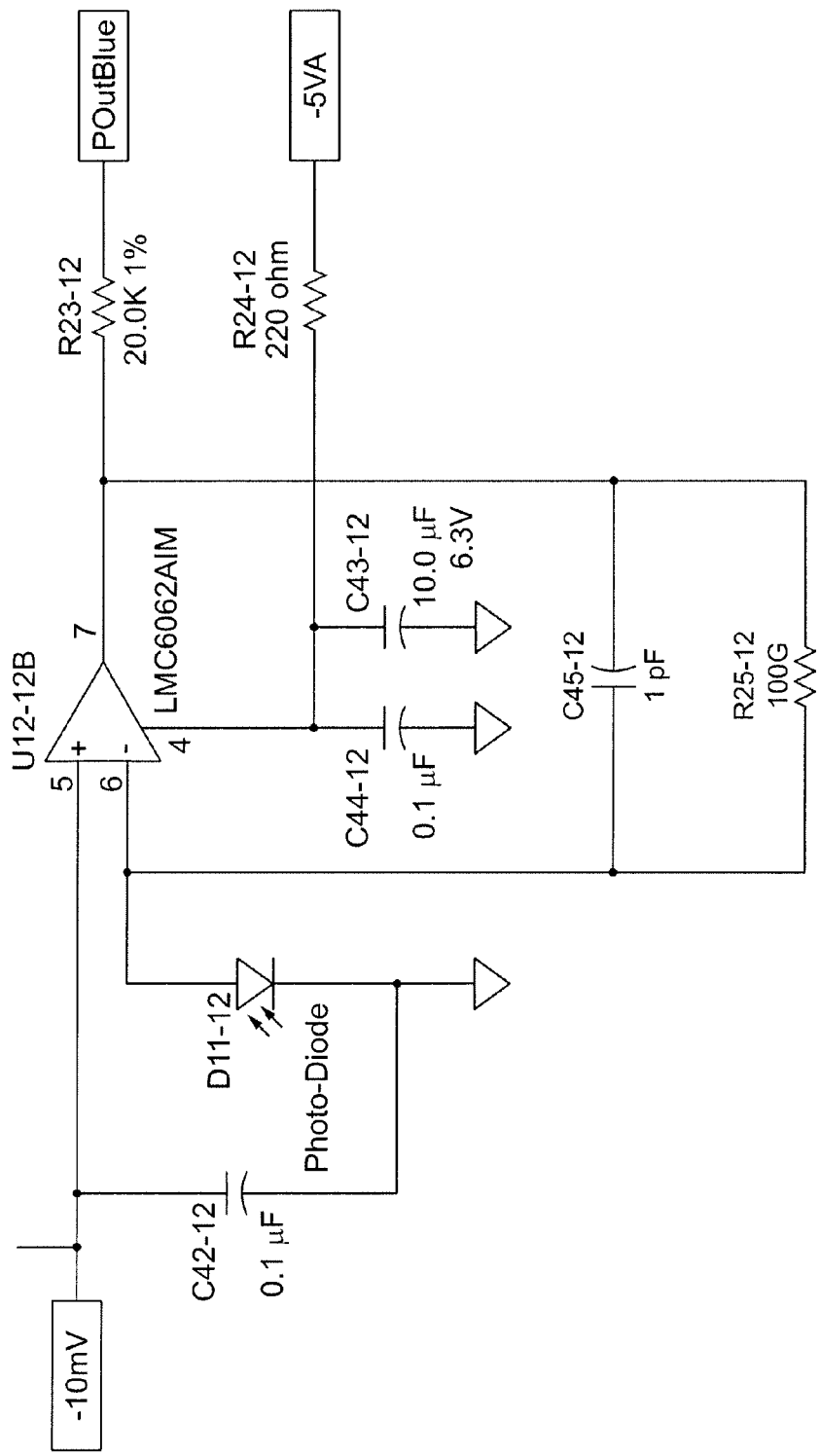
FIG. 34 shows exemplary pre-amplifier circuitry for a fluorescence detector.

The FIG. 34 shows a current-to-voltage converter/pre-amplifier circuit suitable for use with the detection system. D11 is the photodetector that collects the fluorescent light coming from the microfluidic channel and converts it into an electric current. The accompanying circuitry is used to convert these fluorescent currents into voltages suitable for measurement and output as a final measure of the fluorescence.

A resistor-capacitor circuit in FIG. 34 contains capacitor C45 and resistor R25. Together, the values of capacitance of C45 and resistance of R25 are chosen so as to impact the time constant $\tau_c$ (equal to the product of R25 and C45) of the circuit as well as gain of the detection circuit. The higher the time constant, the more sluggish is the response of the system to incident light. It typically takes the duration of a few time constants for the photodetector to completely charge to its maximum current or to discharge to zero from its saturation value. It is important for the photo current to decay to zero between measurements, however. As the PCR systems described herein are intended to afford rapid detection measurements, the product $R_{25}C_{45}$ should therefore be made as low as possible. However, the gain of the pre-amplifier whose circuitry is shown is directly proportional to the (fluorescent-activated) current generated in the photodetector and the resistance $R_{25}$. As the fluorescence signal from the microfluidic channel device is very faint (due to low liquid volume as well as small path lengths of excitation), it is thus important to maximize the value of $R_{25}$. In some embodiments, $R_{25}$ is as high as 100 Giga-Ohms (for example, in the range 10-100 G$\Omega$), effectively behaving as an open-circuit. With such values, the time-constant can take on a value of approximately 50-100 ms by using a low-value capacitor for C45. For example, the lowest possible available standard off-the-shelf capacitor has a value of 1 pF (1 picoFarad). A time-constant in the range 50-100 ms ensures that the photocurrent decays to zero in approximately 0.5 s (approx. 6 cycles) and therefore that approximately 2 samplings can be made per second. Other time constants are consistent with effective use of the technology herein, such as in the range 10 ms-1 s, or in the range 50 ms-500 ms, or in the range 100-200 ms. The actual time constant suitable for a given application will vary according to circumstance and choice of capacitor and resistor values. Additionally, the gain achieved by the pre-amplifier circuit herein may be in the range of $10^7$-$5\times10^9$, for example may be $1\times10^9$.

As the resistance value for R25 is very high ($\sim100$ G$\Omega$), the manner of assembly of this resistor on the optics board is important for the overall efficiency of the circuit. Effective cleaning of the circuit during assembly and before use is important to achieve an optimal time-constant and gain for the optics circuit.

It is also important to test each photo-diode that is used, because many do not perform acccording to specification.

Sensitivity and Aperturing

The LED light passes through a filter before passing through the sample in the microfluidic channel (as described herein, typically 300µ deep). This is a very small optical path-length for the light in the sample. The generated fluorescence then also goes through a second filter, and into a photo-detector. Ultimately, then, the detector must be capable of detecting very little fluorescence. Various aspects of the detector configuration can improve sensitivity, however.

The illumination optics can be designed so that the excitation light falling on the PCR reactor is incident along an area that is similar to the shape of the reactor. As the reactor is typically long and narrow, the illumination spot should be long and narrow, i.e., extended, as well. The length of the spot can be adjusted by altering a number of factors, including: the diameter of the bore where the LED is placed (the tube that holds the filter and lens has an aperturing effect); the distance of the LED from the PCR reactor; and the use of proper lens at the right distance in between. As the width of the beam incident on the reactor is determined by the bore of the optical element (approximately 6 mm in diameter), it is typical to use an aperture (a slit having a width approximately equal to the width of the reactor, and a length equal to the length of the detection volume) to make an optimal illumination spot. A typical spot, then, is commensurate with the dimensions of a PCR reaction chamber, for example 1.5 mm wide by 7 mm long. FIG. 35A shows the illumination spot across 12 PCR reactors for the two different colors used. A typical aperture is made of anodized aluminum and has very low autofluorescence in the wavelengths of interest. FIG. 35B illustrates a cross-section of a detector, showing an exemplary location for an aperture 802.

The optimal spot size and intensity is importantly dependent on the ability to maintain the correct position of the LED's with respect to the center of the optical axis. Special alignment procedures and checks can be utilized to optimize this. The different illuminations can also be normalized with respect to each other by adjusting the power current through each of the LED's or adjusting the fluorescence collection time (the duration for which the photodetector is on before measuring the voltage) for each detection spot. It is also important to align the detectors with the axis of the microchannels.

The aperturing is also important for successful fluorescence detection because as the cross-sectional area of the incident beam increases in size, so the background fluorescence increases, and the fluorescence attributable only to the molecules of interest (PCR probes) gets masked. Thus, as the beam area increases, the use of an aperture increases the proportion of collected fluorescence that originates only from the PCR reactor. Note that the aperture used in the detector herein not only helps collect fluorescence only from the reaction volume but it correspondingly adjusts the excitation light to mostly excite the reaction volume. The excitation and emission aperture is, of course, the same.

Based on a typical geometry of the optical excitation and emission system and aperturing, show spot sizes as small as 0.5 mm by 0.5 mm and as long as 8 mm×1.5 mm have been found to be effective. By using a long detector (having an active area 6 mm by 1 mm) and proper lensing, the aperture design can extend the detection spot to as long as 15-20 mm, while maintaining a width of 1-2 mm using an aperture. Correspondingly, the background fluorescence decreases as the spot size is decreased, thereby increasing the detection sensitivity.

Use of Detection System to Measure/Detect Fluid in PCR Chamber

The fluorescence detector is sensitive enough to be able to collect fluorescence light from a PCR chamber of a microfluidic substrate. The detector can also be used to detect the presence of liquid in the chamber, a measurement that provides a determination of whether or not to carry out a PCR cycle for that chamber. For example, in a multi-sample cartridge, not all chambers will have been loaded with sample; for those that are not, it would be unnecessary to apply a heating protocol thereto. One way to determine presence or absence of a liquid is as follows. A background reading is taken prior to filling the chamber with liquid. Another reading is taken after microfluidic operations have been performed that should result in filling the PCR chamber with liquid. The presence of liquid alters the fluorescence reading from the chamber. A programmable threshold value can be used to tune an algorithm programmed into a processor that controls operation of the apparatus as further described herein (for example, the second reading has to exceed the first reading by 20%). If the two readings do not differ beyond the programmed margin, the liquid is deemed to not have entered the chamber, and a PCR cycle is not initiated for that chamber. Instead, a warning is issued to a user.

Exemplary Electronics and Software

Figure 36:
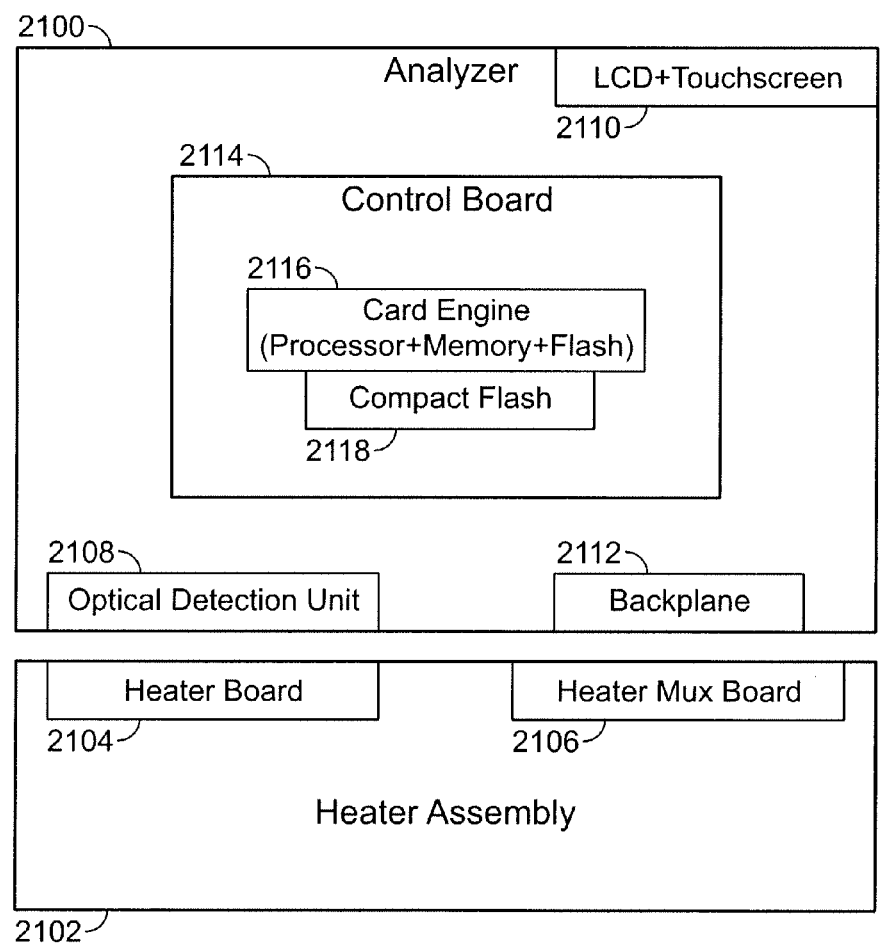
FIG. 36 shows an exemplary layout for electronics and software components, as further described herein.

The heater unit described herein can be controlled by various electronics circuitry, itself operating on receipt of computer-controlled instructions. FIG. 36 illustrates exemplary electronics architecture modules for operating a heater unit and diagnostic apparatus. It would be understood by one of ordinary skill in the art that other configurations of electronics components are consistent with operation of the apparatus as described herein. In the exemplary embodiment, the electronics architecture is distributed across two components of the apparatus: the Analyzer 2100 and a Heater unit 2102. The Analyzer apparatus as further described herein contains, for example, an Optical Detection Unit 2108, a Control Board 2114, a Backplane 2112, and a LCD Touchscreen 2110. The Control Board includes a Card Engine 2116 further described herein, and Compact Flash memory 2118, as well as other components. The Heater Assembly includes a Heater Board 2104 and a Heater Mux Board 2106, both further described herein.

In one embodiment, the Card Engine electronics module 2116 is a commercial, off the shelf "single board computer" containing a processor, memory, and flash memory for operating system storage.

The optional LCD+Touchscreen electronics module 2110 is a user interface, for example, driven through a touchscreen, such as a 640 pixel by 480 pixel 8 inch LCD and 5-wire touchscreen.

The Compact Flash electronics module 2118 is, for example, a 256 megabyte commercial, off the shelf, compact flash module for application and data storage. Other media are alternatively usable, such as USB-drive, smart media card, memory stick, and smart data-card having the same or other storage capacities.

The Backplane electronics module 2112 is a point of connection for the removable heater assembly 2102. Bare PC boards with two connectors are sufficient to provide the necessary level of connectivity.

The Control Board electronics module 2114 supports peripherals to the Card Engine electronics module 2116. In one embodiment, the peripherals include such devices as a USB host+slave or hub, a USB CDROM interface, serial ports, and ethernet ports. The Control Board 2114 can include a power monitor with a dedicated processor. The Control Board may also include a real time clock. The Control Board may further include a speaker. The Control Board 2114 also includes a CPLD to provide SPI access to all other modules and programming access to all other modules. The Control Board includes a programmable high voltage power supply. The Control Board includes a Serial-Deserializer interface to the LCD+Touchscreen electronics module 2110 and to the Optical Detection Unit electronics module 2108. The Control Board also includes module connectors.

In the exemplary embodiment, the optical detection unit electronics module 2108 contains a dedicated processor. The optical detection unit 2108 contains a serializer-deserializer interface. The optical detection unit 2108 contains LED drivers. The optical detection unit also contains high gain-low noise photodiode amplifiers. The optical detection unit can have power monitoring capability. The optical detection unit can also be remotely reprogrammable.

The Heater Board electronics module 2104 is preferably a glass heater board. The Heater Board has PCB with bonding pads for glass heater board and high density connectors.

In embodiment, the heater mux ('multiplex') board electronics module 2106 has 24 high-speed ADC, 24 precision current sources, and 96 optically isolated current drivers for heating. The heater mux board has the ability to time-multiplex heating/measurement. The heater mux board has multiplexer banks to multiplex inputs to ADC, and to multiplex current source outputs. The heater mux board has a FPGA with a soft processor core and SDRAM. The heater mux board has a Power Monitor with a dedicated processor. The Heater Mux Board can be remotely reprogrammable.

In another embodiment, control electronics can be spread over four different circuit board assemblies. These include the MAIN board: Can serve as the hub of the Analyzer control electronics and manages communication and control of the other various electronic subassemblies. The main board can also serve as the electrical and communications interface with the external world. An external power supply (12V DC/10A; UL certified) can be used to power the system. The unit can communicate via 5 USB ports, a serial port and an Ethernet port. Finally, the main board can incorporate several diagnostic/safety features to ensure safe and robust operation of the Analyzer.

MUX Board: Upon instruction from the main board, the MUX board can perform all the functions typically used for accurate temperature control of the heaters and can coordinate the collection of fluorescence data from the detector board.

LCD Board: Can contain the typical control elements to light up the LCD panel and interpret the signals from the touch sensitive screen. The LCD/touch screen combination can serve as a mode of interaction with the user via a Graphical User Interface.

Detector Board: Can house typical control and processing circuitry that can be employed to collect, digitize, filter, and transmit the data from the fluorescence detection modules.

Certain software can be executed in each electronics module. The Control Board Electronics Module executes, for example, Control Board Power Monitor software. The Card Engine electronics module executes an operating system, graphical user interface (GUI) software, an analyzer module, and an application program interface (api). The Optical Detection Unit electronics module executes an optics software module. The Heater Mux Board electronics module executes dedicated Heater Mux software, and Heater Mux Power Monitor software. Each of the separate instances of software can be modular and under a unified control of, for example, driver software.

The exemplary electronics can use Linux, UNIX, Windows, or MacOS, including any version thereof, as the operating system. The operating system is preferably loaded with drivers for USB, Ethernet, LCD, touchscreen, and removable media devices such as compact flash. Miscellaneous programs for configuring the Ethernet interface, managing USB connections, and updating via CD-ROM can also be included.

In the embodiment of FIG. 36, the analyzer module is the driver for specific hardware. The analyzer module provides access to the Heater Mux Module, the Optical Detection Unit, the Control Board Power Monitor, the Real Time Clock, the High Voltage Power Supply, and the LCD backlight. The analyzer module provides firmware programming access to the Control Board power monitor, the Optical Detection Unit, and the Heater Mux Module.

The API provides uniform access to the analyzer module driver. The API is responsible for error trapping, and interrupt handling. The API is typically programmed to be thread safe.

The GUI software can be based on a commercial, off-the-shelf PEG graphics library. The GUI can use the API to coordinate the self-test of optical detection unit and heater assembly. The GUI starts, stops, and monitors test progress.

The GUI can also implement an algorithm to arrive on diagnosis from fluorescence data. The GUI provides access control to unit and in some embodiments has an HIS/LIS interface.

The Control Board Power Monitor software monitors power supplies, current and voltage, and signals error in case of a fault.

The Optics Software performs fluorescence detection which is precisely timed to turn on/off of LED with synchronous digitization of the photodetector outputs. The Optics Software can also monitor power supply voltages. The Optics Software can also have self test ability.

The Heater Mux Module software implements a "protocol player" which executes series of defined "steps" where each "step" can turn on sets of heaters to implement a desired microfluidic action. The Heater Mux Module software also has self test ability. The Heater Mux Module software contains a fuzzy logic temperature control algorithm.

The Heater Mux Power Monitor software monitors voltage and current levels. The Heater Mux Power Monitor software can participate in self-test, synchronous, monitoring of the current levels while turning on different heaters.

EXAMPLES

The following are exemplary aspects of various parts and functions of the system described herein.

Additional embodiments of a cartridge are found in U.S. patent application Ser. No. 11/940,310, entitled "Microfluidic Cartridge and Method of Making Same", and filed on even date herewith, the specification of which is incorporated herein by reference.

Additional embodiments of heater units and arrays are described in U.S. patent application Ser. No. 11/940,315, entitled "Heater Unit for Microfluidic Diagnostic System" and filed on even date herewith, the specification of which is incorporated herein by reference in its entirety.

Further description of suitably configured detectors are described in U.S. patent application Ser. No. 11/940,321, filed on Nov. 14, 2007 and entitled "Fluorescence Detector for Microfluidic Diagnostic System", incorporated herein by reference.

Example 1

Analyzer Having Removable Heater Unit

This non-limiting example describes pictorially, various embodiments of an apparatus, showing incorporation of a heater unit and a microfluidic cartridge operated on by the heater unit.

Figure 37:
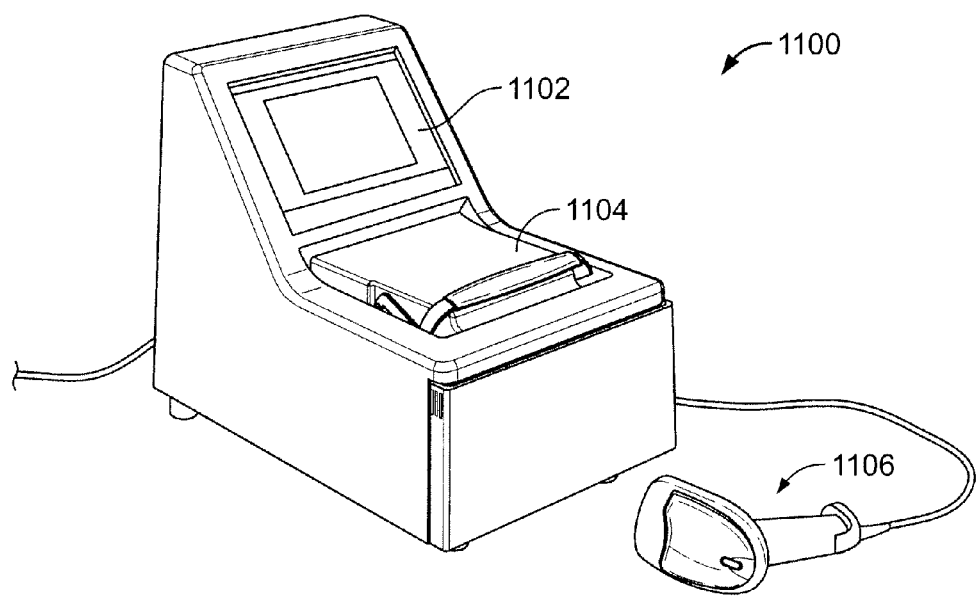
FIG. 37 shows an exemplary apparatus, a microfluidic cartridge, and a read head, as further described herein.
Figure 38:
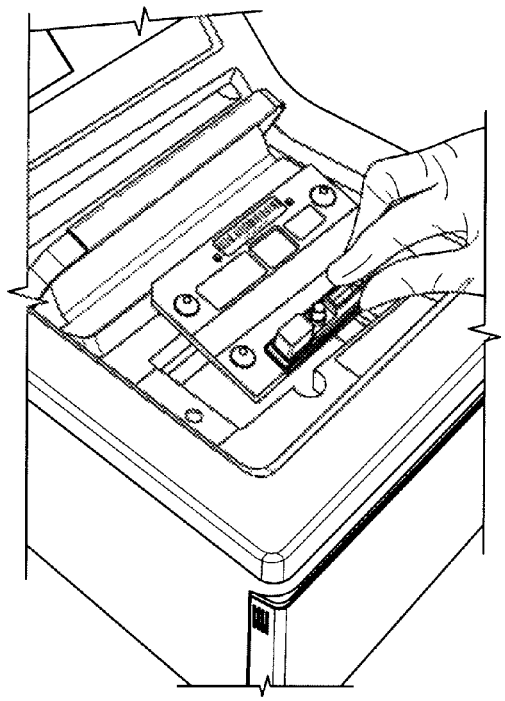
FIGS. 38-39 show positioning of a cartridge in an exemplary apparatus.
Figure 39:
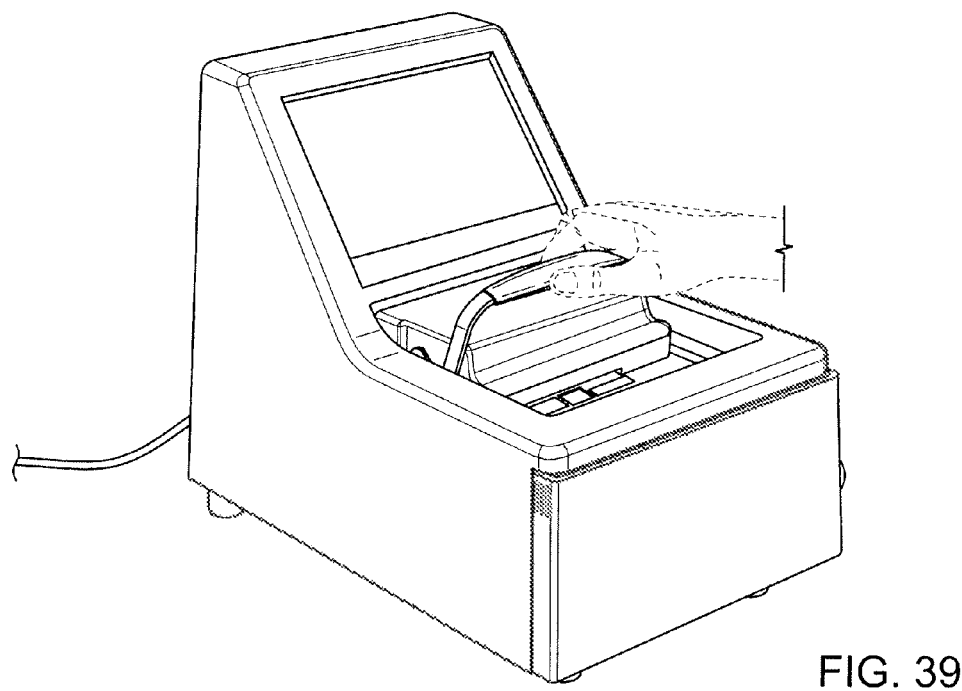

FIG. 37 shows an apparatus 1100 that includes a housing having a display output 1102, an openable lid 1104, and a bar code reader 1106. The cartridge is positioned in a single orientation in a receiving bay under the lid, FIG. 38. The lid of the apparatus can be closed to apply pressure to the cartridge, as shown in FIG. 39. The unit currently weighs about 20 lbs. and is approximately 10" wide by 16" deep by 13" high.

Figure 40:
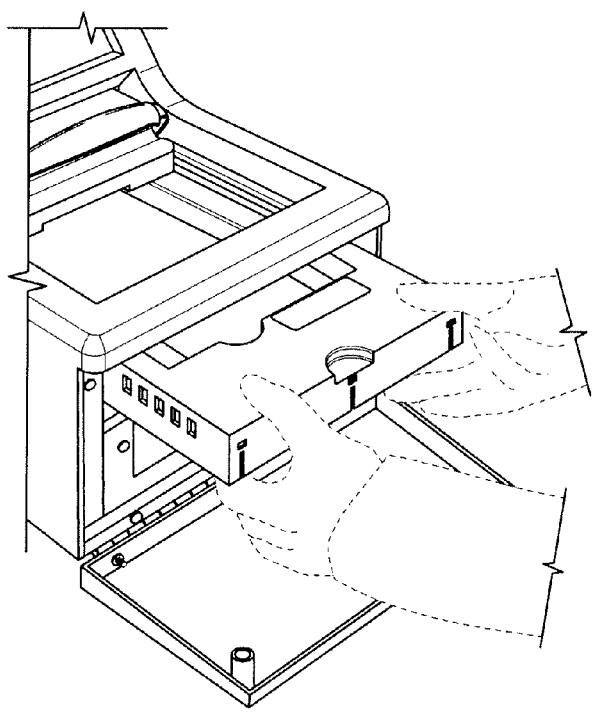
FIGS. 40 and 41 show removal of a heater unit from an exemplary apparatus.
Figure 41:
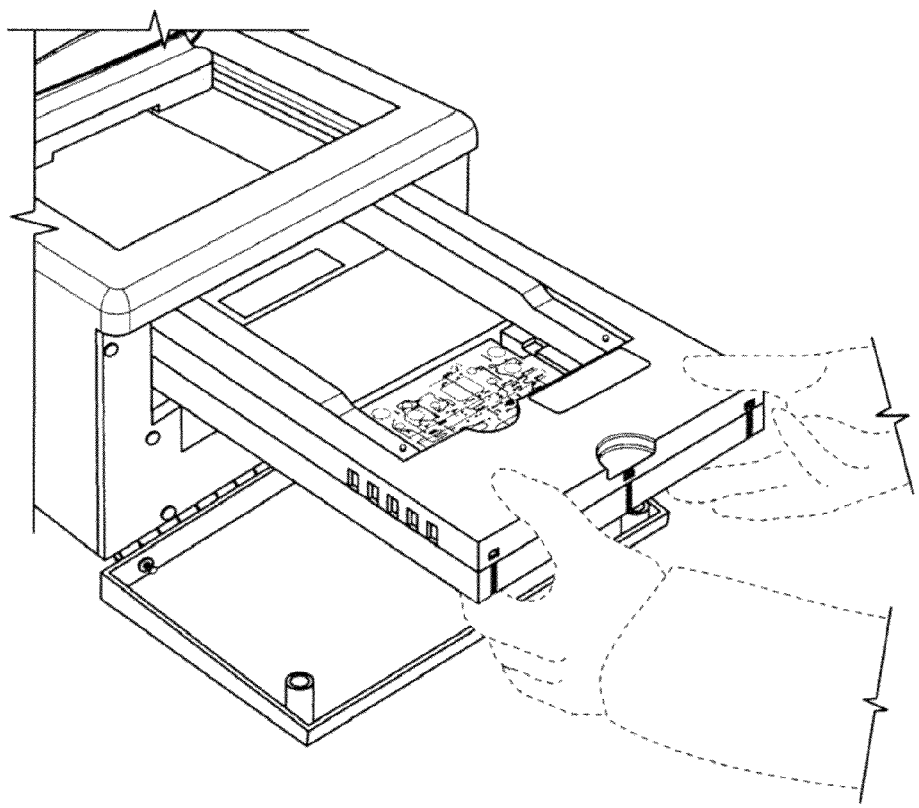

FIGS. 40 and 41: The heating stage of the apparatus can be removable for cleaning, maintenance, or to replace a custom heating stage for a particular microfluidic cartridge. FIGS. 40 and 41 also show how a heater unit is insertable and removable from a front access door to an analyzer apparatus.

Example 2

Assembly of an Exemplary Heater Unit

Figure 42B:
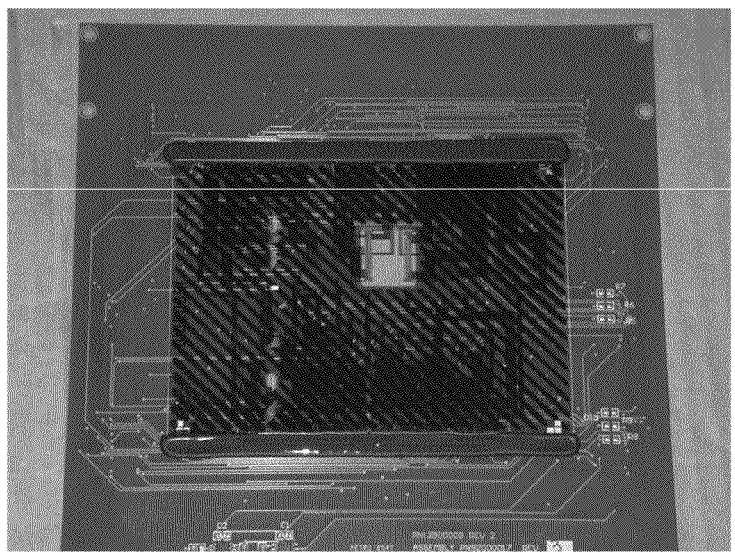
FIGS. 42A and 42B show an exemplary heater unit and heater substrate.
Figure 42A:
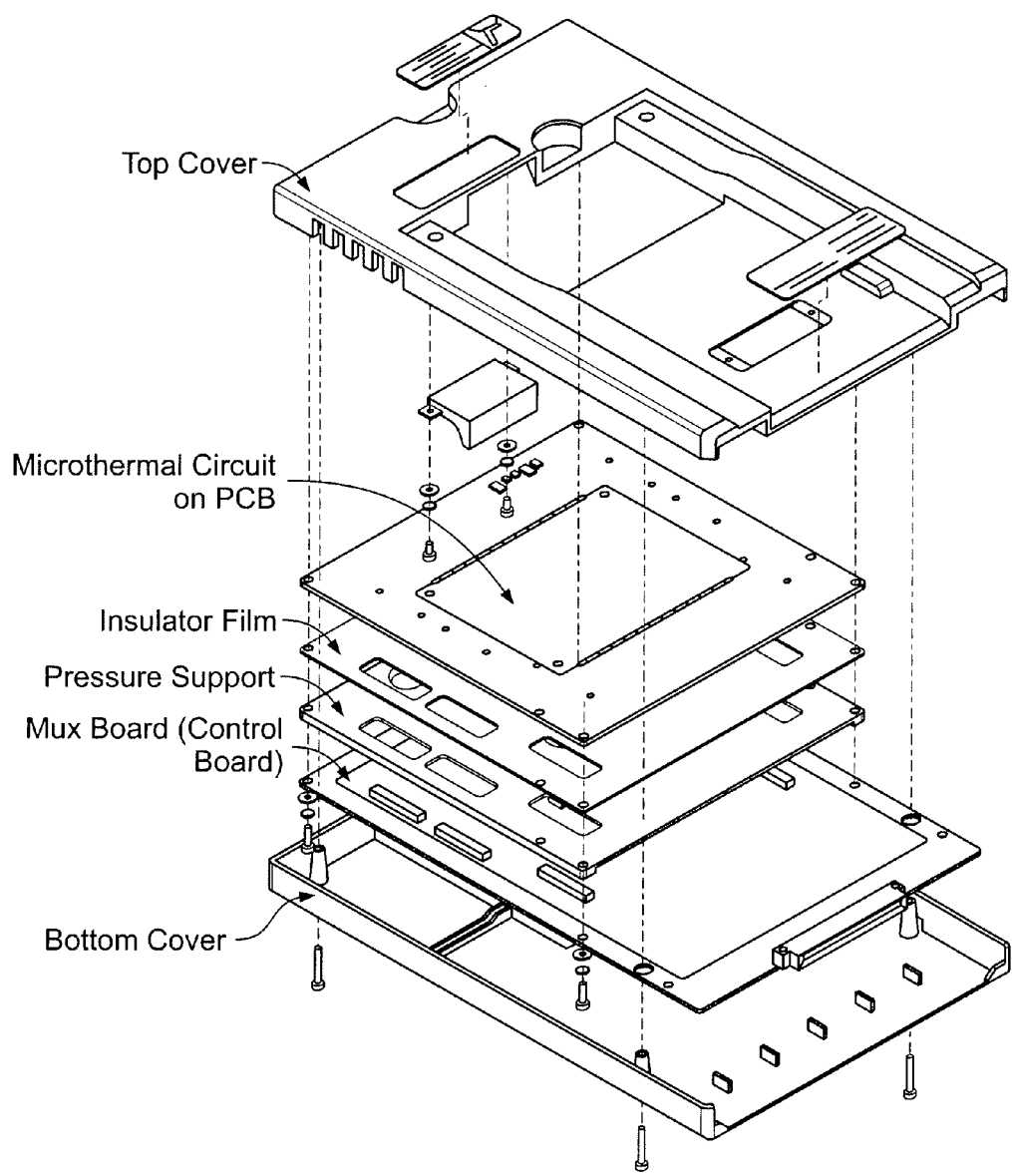

FIG. 42A shows an exploded view of an exemplary heater unit. The unit has a top cover and a bottom cover that together enclose a Mux board (control board), a pressure support layer, and insulator film, and a microthermal circuit on a PCB. The last of these is the heat source that selectively heats regions of a microfluidic substrate placed in contact therewith through the top cover.

An exemplary heater substrate, FIG. 42B, consists of a photo-lithographically processed glass wafer bonded to a standard 0.100" standard FR4 printed circuit board. The glass wafer is 0.5 mm thick and is cut into a rectangle the size of ~3.5×4.25 inches. The glass substrate has numerous metal heaters and resistive temperature sensors photo-lithographically etched on the surface of the glass wafer. The substrate is aligned and bonded to the PCBoard using a compliant epoxy, ensuring flatness to within 2-3 mils over the surface of the wafer. The cured epoxy should withstand up to 120° C. for two hours minimum. Approximately 300-400 bond pads of the size of approximately 1 mm×0.25 mm, with exposed gold surfaces, are located along the two long edges of the wafer. These pads are wirebonded (ball-bonding) to corresponding pads on the PCB using 1.5 mil gold wires. Wire bonding is a threading process, standard in semiconductor FAB. Alternatively, a flip-chip method may be used, though such methods are more complicated and may warp the wafer because of thermal mismatch. Wire bonds should have good integrity and pass defined pull strength. The substrate is baked at 120° C. for two hours and then the wire bonds are encapsulated by a compliant epoxy that will protect the wirebonds but not damage the bonds even at 120° C. Encapsulant should not spill over predefined area around the wirebonds and should not be taller than a defined height. For example, instead of laying epoxy all over the substrate, lines (e.g., a hash pattern) of it are made so that epoxy cures and air escapes through side. Alternatively, a laminate fill (adhesive on both sides) can be used. Standard connectors are soldered to the PCB and then the unit is tested using a test set-up to ensure all heaters and sensors read the right resistance values.

Figure 28:
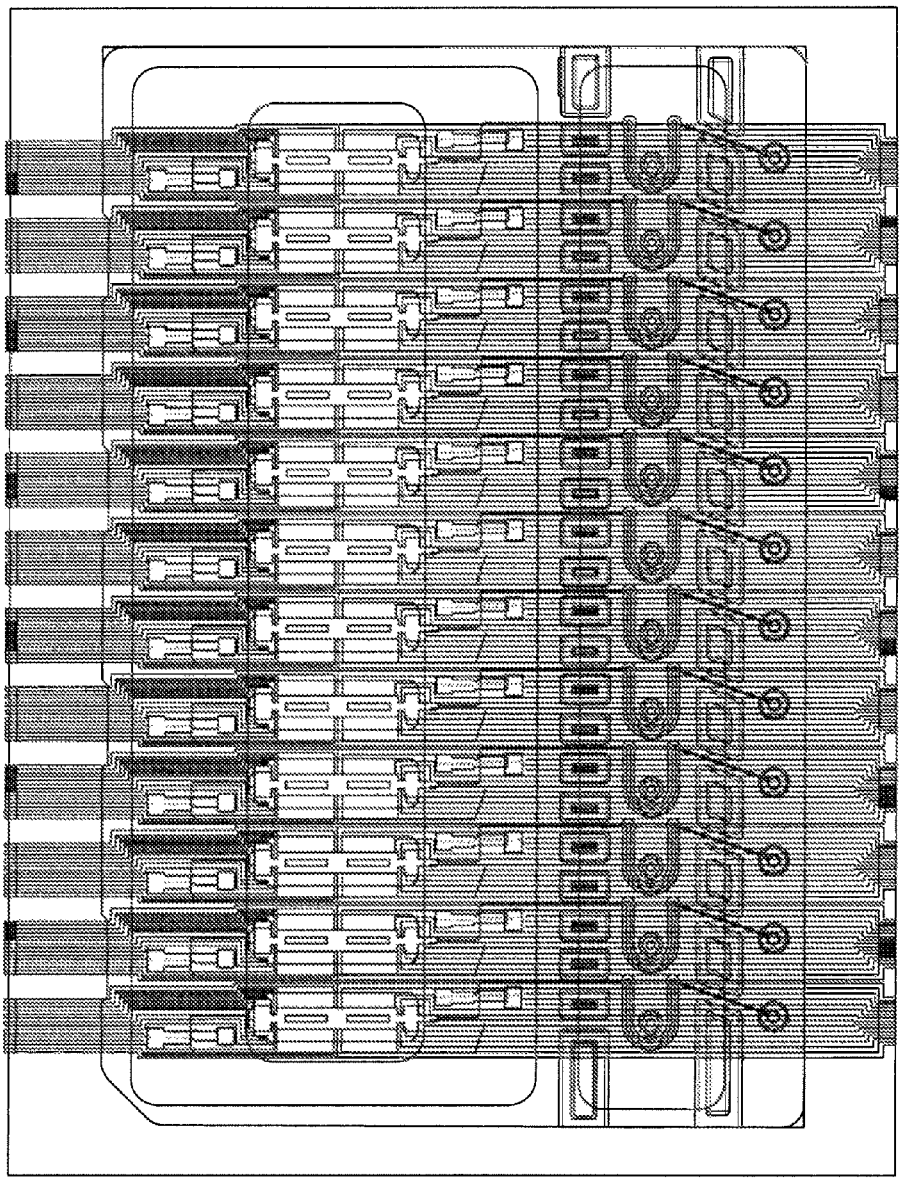
FIG. 28 shows an overlay of an array of heater elements on an exemplary multi-lane microfluidic cartridge, wherein various microfluidic networks are visible.
Figure 29:
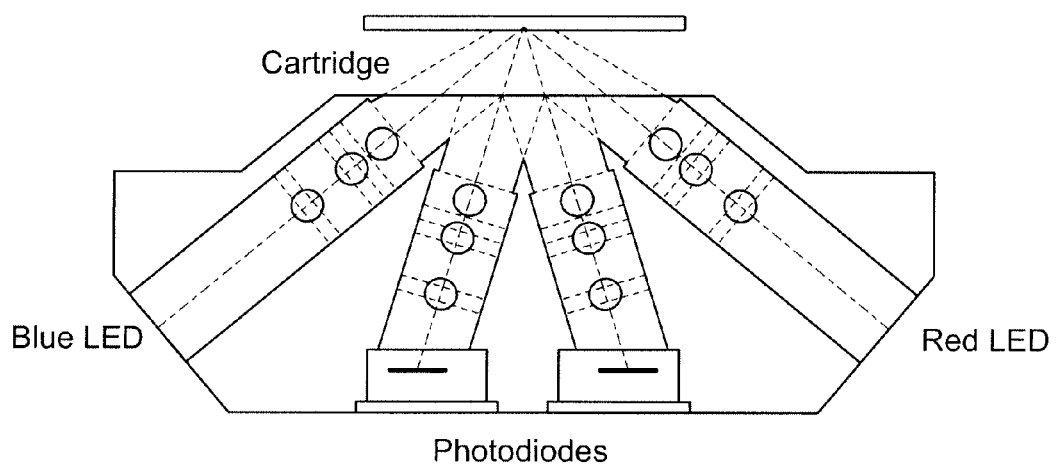
FIG. 29 shows a cross-sectional view of an exemplary detector.
Figure 30:
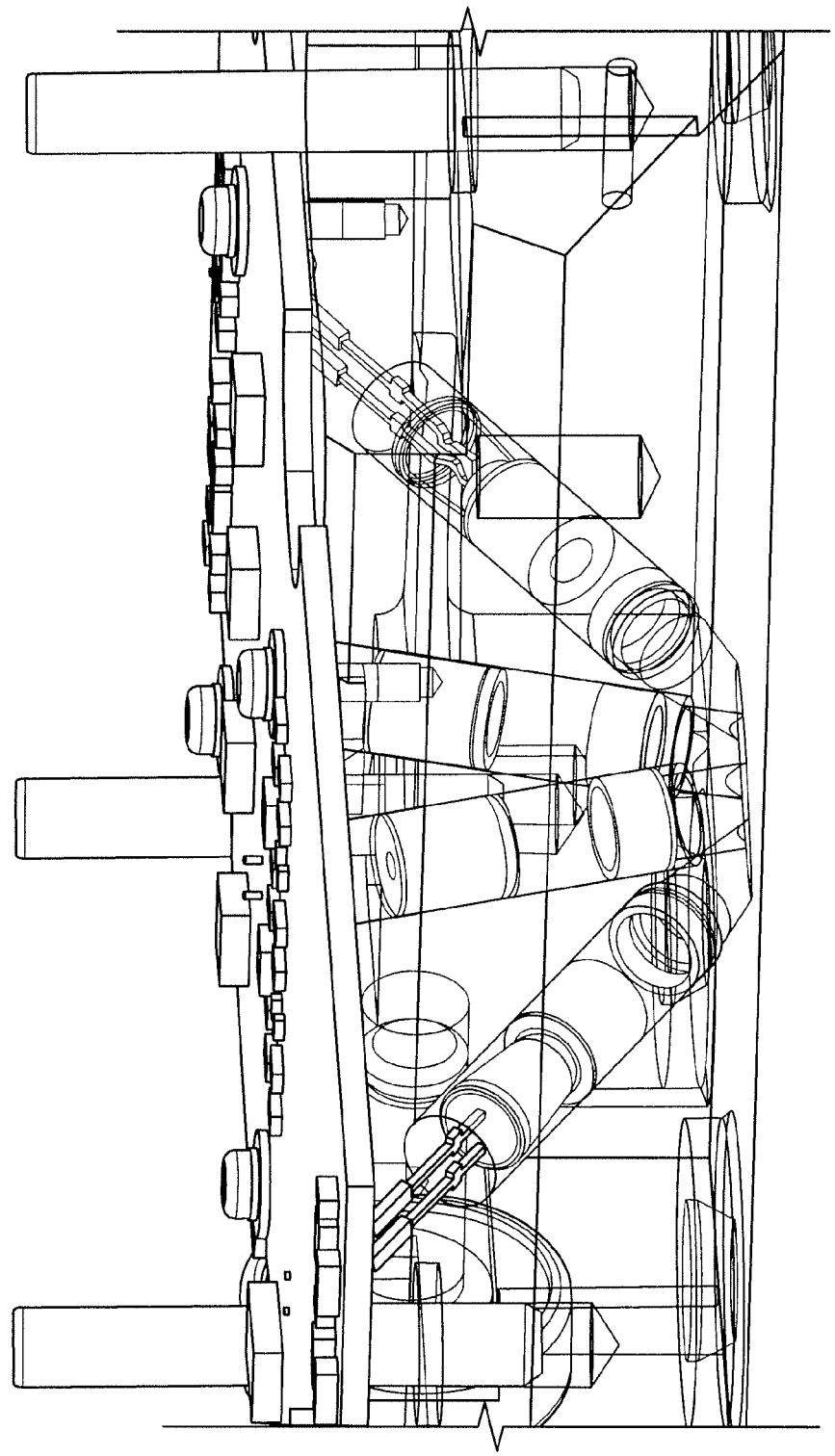
FIG. 30 shows a perspective view of a detector in a read-head.

Pictures of an exemplary Mux board and assembled heater unit are shown in FIGS. 27-29.

Example 3

Pulse Width Modulation for Heater Circuitry

In various embodiments, the operation of a PWM generator can also include a programmable start count in addition to the aforementioned end count and granularity. In such embodiments, multiple PWM generators can produce signals that can be selectively non-overlapping (e.g., by multiplexing the on-time of the various heaters) such that the current capacity of the high voltage power is not exceeded. Multiple heaters can be controlled by different PWM signal generators with varying start and end counts. The heaters can be divided into banks, whereby a bank defines a group of heaters of the same start count. For example, 36 PWM generators can be grouped into six different banks, each corresponding to a certain portion of the PWM cycle (500 ms for this example). The end count for each PWM generator can be selectively programmed such that not more than six heaters will be on at any given time. A portion of a PWM cycle can be selected as dead time (count 3000 to 4000 for this example) during which no heating takes place and sensitive temperature sensing circuits can use this time to sense the temperature. The table below represents a PWM cycle for the foregoing example:

|  | Start Count | End Count | Max End count |
|---|---|---|---|
| Bank 1 | | | |
| PWM generator#1 | 0 | 150 | 500 |
| PWM generator#2 | 0 | 220 | 500 |
| ... | ... | ... | ... |
| PWM generator#6 | 0 | 376 | 500 |
| Bank 2 | | | |
| PWM generator#7 | 500 | 704 | 1000 |
| PWM generator#8 | 500 | 676 | 1000 |
| ... | ... | ... | ... |
| PWM generator#12 | 500 | 780 | 1000 |
| Bank 3 | | | |
| PWM generator#13 | 1000 | 1240 | 1500 |
| PWM generator#14 | 1000 | 1101 | 1500 |
| ... | ... | ... | ... |
| PWM generator#18 | 1000 | 1409 | 1500 |
| Bank 4 | | | |
| PWM generator#19 | 1500 | 1679 | 2000 |
| PWM generator#20 | 1500 | 1989 | 2000 |
| ... | ... | ... | ... |
| PWM generator#24 | 1500 | 1502 | 2000 |
| Bank 5 | | | |
| PWM generator#25 | 2000 | 2090 | 2500 |
| PWM generator#26 | 2000 | 2499 | 2500 |
| ... | ... | ... | ... |
| PWM generator#30 | 2000 | 2301 | 2500 |
| Bank 6 | | | |
| PWM generator#31 | 2500 | 2569 | 3000 |
| PWM generator#32 | 2500 | 2790 | 3000 |
| ... | ... | ... | ... |
| PWM generator#36 | 2500 | 2678 | 3000 |

Example 4

Detector Integrated in Force Member

This non-limiting example describes pictorially, various embodiments of a detection system integrated into a force member, in an apparatus for carrying out diagnostics on microfluidic samples.

Figure 43A:
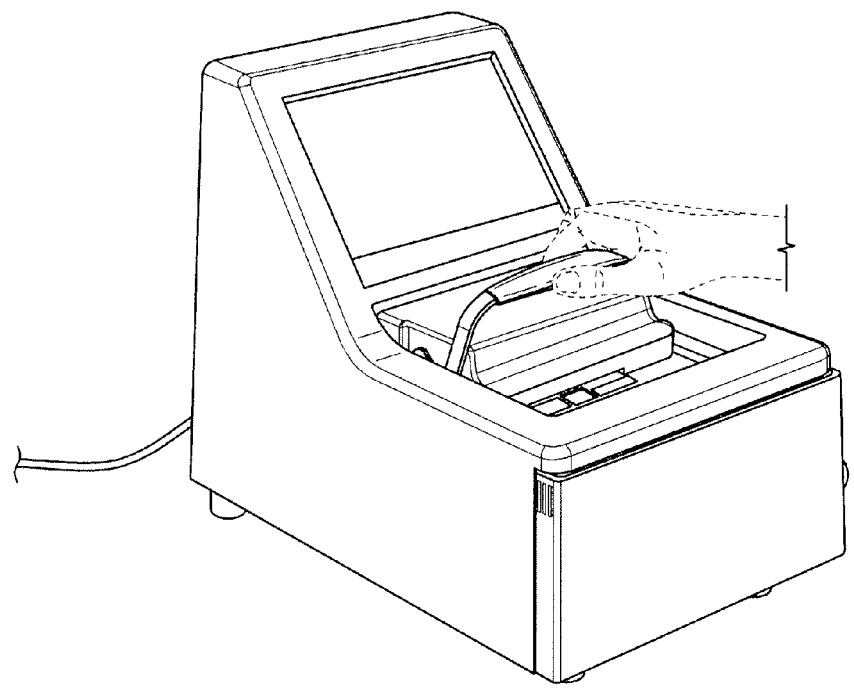
FIGS. 43A and 43B show an exemplary apparatus having a detector mounted in a sliding lid.

FIG. 43A: The lid of the apparatus can be closed, which can block ambient light from the sample bay, and place an optical detector contained in the lid into position with respect to the microfluidic cartridge.

Figure 43B:
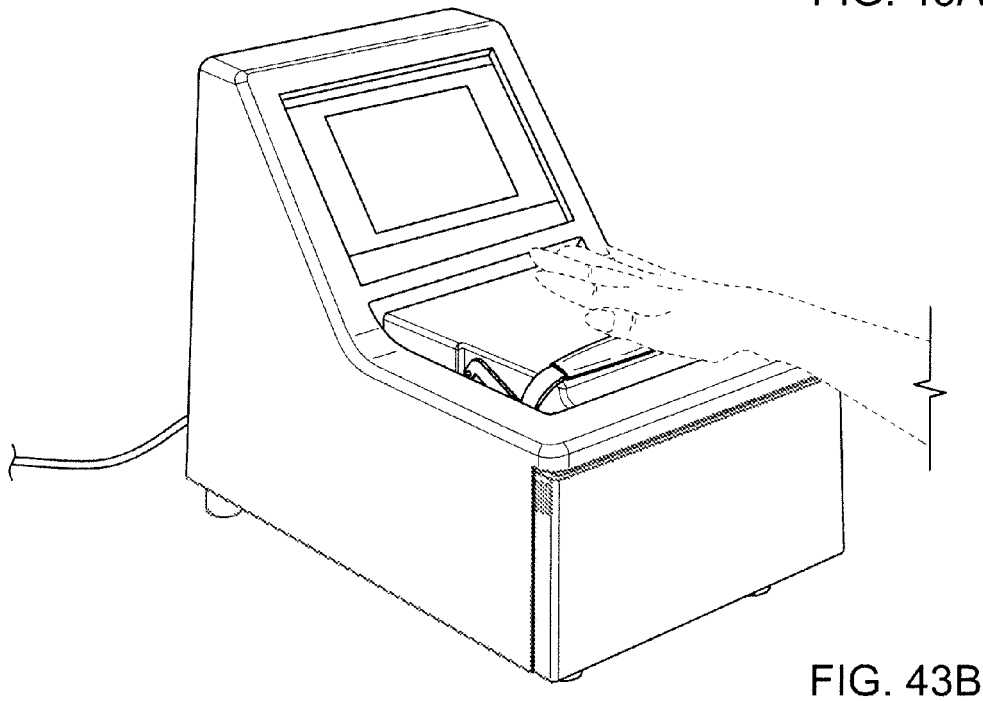

FIG. 43B: The lid of the apparatus can be closed to apply pressure to the cartridge. Application of minimal pressure on the cartridge: after the slider compresses the cartridge, the slider can compress the compliant label of the cartridge. This can cause the bottom of the cartridge to be pressed down against the surface of the heater unit present in the heater module. Springs present in the slider can deliver, for example approximately 50 lb of pressure to generate a minimum pressure, for example 2 psi over the entire cartridge bottom.

Thermal interface: the cartridge bottom can have a layer of mechanically compliant heat transfer laminate that can enable thermal contact between the microfluidic substrate and the microheater substrate of the heater module. A minimal pressure of 1 psi can be employed for reliable operation of the thermal valves, gate and pumps present in the microfluidic cartridge.

Mechanicals and assembly: the Analyzer can have a simple mechanical frame to hold the various modules in alignment. The optics module can be placed in rails for easy opening and placement of cartridges in the Analyzer and error-free alignment of the optics upon closing. The heater/sensor module can be also placed on rails or similar guiding members for easy removal and insertion of the assembly.

Figure 44A:
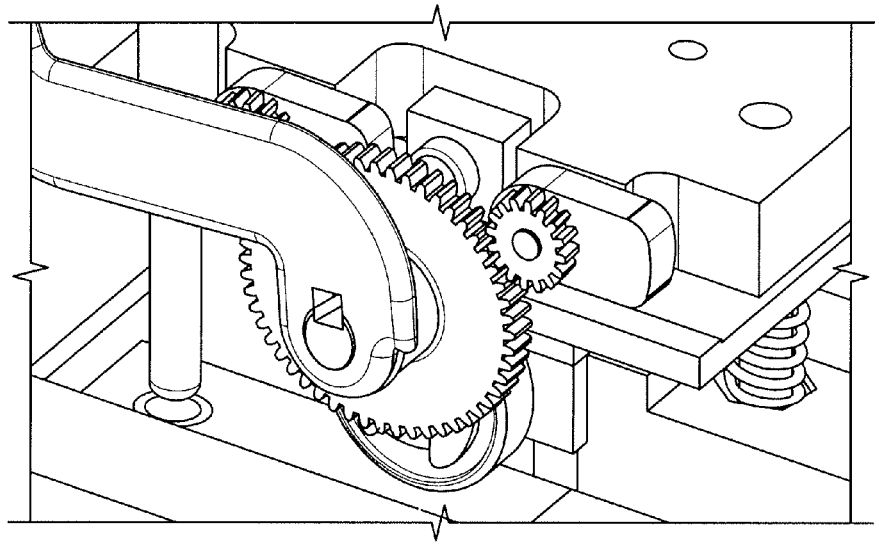
FIGS. 44A-44C show a force member.
Figure 44B:
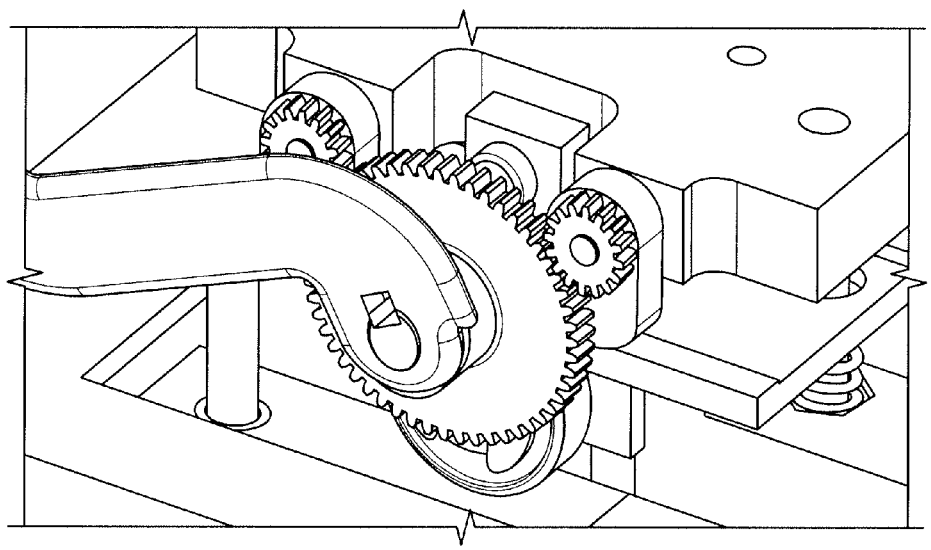
Figure 44C:
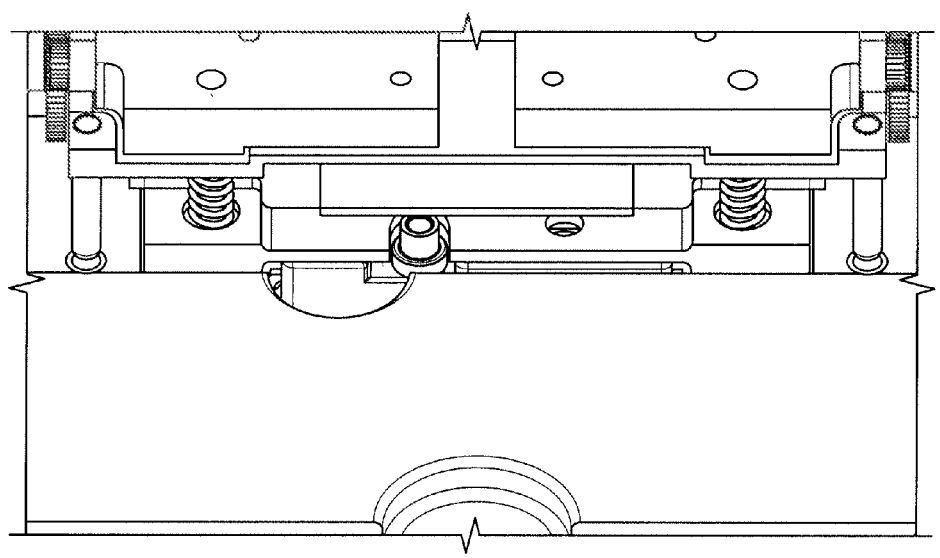

Slider: the slider of the Analyzer can house the optical detection system as well as the mechanical assembly that can enables the optics jig to press down on the cartridge when the handle of the slider is turned down onto the analyzer. The optics jig can be suspended from the case of the slider at 4 points. Upon closing the slider and turning the handle of the analyzer down, 4 cams can turn to push down a plate that presses on 4 springs. On compression, the springs can deliver approximately 50 lb on the optical block. See FIGS. 44A-44C.

The bottom surface of the optics block can be made flat to within 100 microns, typically within 25 microns, and this flat surface can press upon the compliant (shore hardness approximately 50-70) label (approximately 1.5 mm thick under no compression) of the cartridge making the pressure more or less uniform over the cartridge. An optional lock-in mechanism can also be incorporated to prevent the slider from being accidentally knocked-off while in use.

FIG. 45A shows a side view of a lever assembly 1200, with lever 1210, gear unit 1212, and force member 1214. Assembly 1200 can be used to close the lid of the apparatus and (through force members 1214) apply force to a microfluidic cartridge 1216 in the receiving chamber 1217. One force member is visible in this cut away view, but any number, for example 4, can be used. The force members can be, for example, a manual spring loaded actuator as shown, an automatic mechanical actuator, a material with sufficient mechanical compliance and stiffness (e.g., a hard elastomeric plug), and the like. The force applied to the microfluidic cartridge 1216 can result in a pressure at the surface of the microfluidic cartridge 1216 of at least about 0.7 psi to about 7 psi (between about 5 and about 50 kilopascals), or in some embodiments about 2 psi (about 14 kilopascals.

Figure 45B:
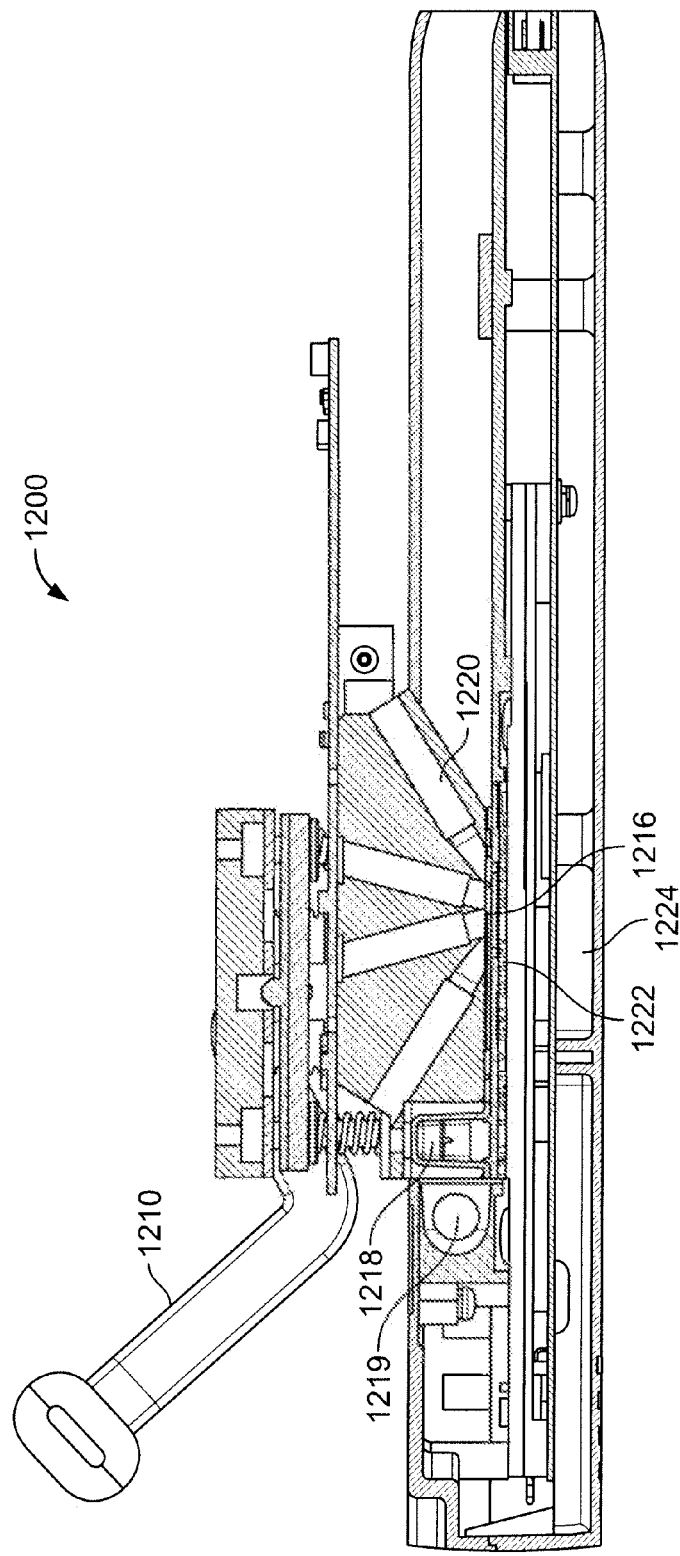

FIG. 45B shows a side view of lever assembly 1200, with microfluidic cartridge 1216 in the receiving chamber 1217. A heat source 1219 (for example, a xenon bulb as shown) can function as a radiant heat source directed at a sample inlet reservoir 1218, where the heat can lyse cells in reservoir 1218. A thermally conductive, mechanically compliant layer 1222 can lie at an interface between microfluidic cartridge 1216 and thermal stage 1224. Typically, microfluidic cartridge 1216 and thermal stage 1224 can be planar at their respective interface surfaces, e.g., planar within about 100 microns, or more typically within about 25 microns. Layer 1222 can improve thermal coupling between microfluidic cartridge 1216 and thermal stage 1224. Optical detector elements 1220 can be directed at the top surface of microfluidic cartridge 1216.

Figure 45C:
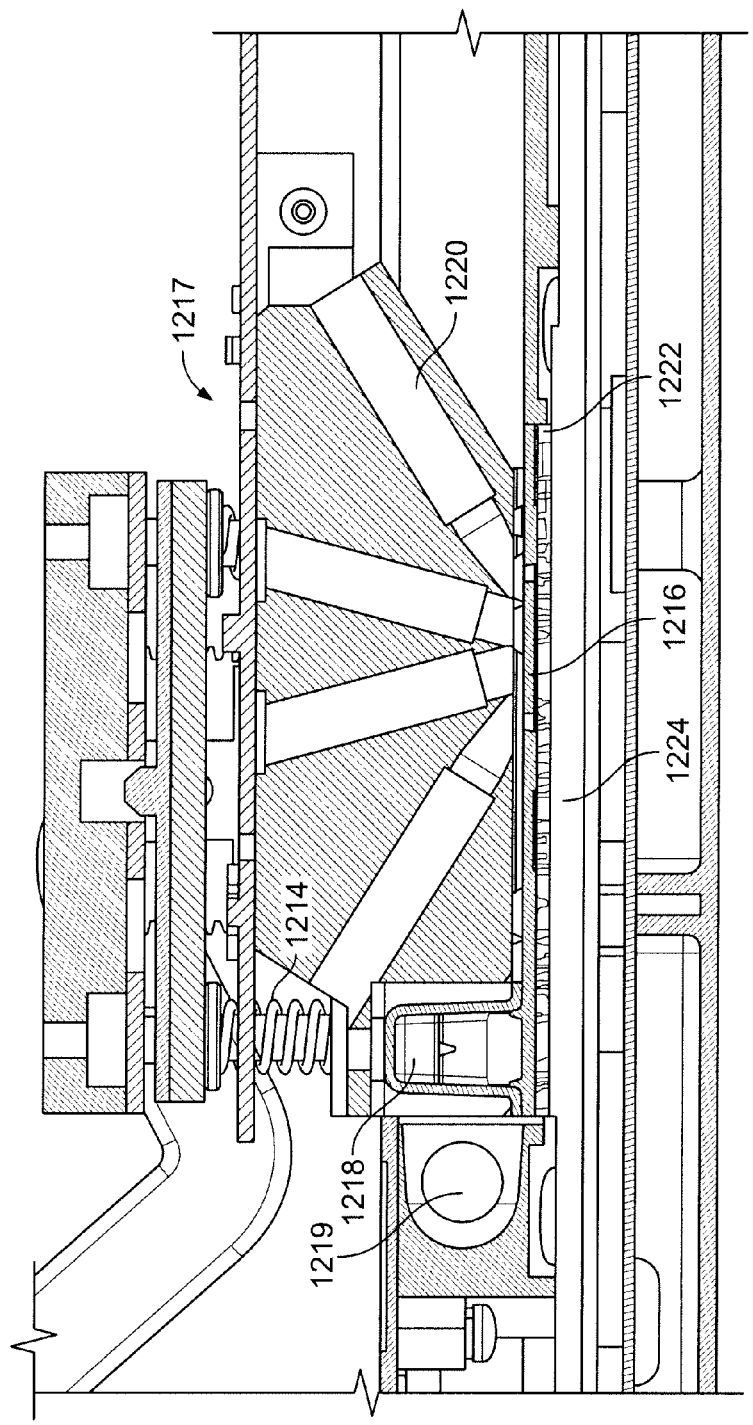
Figure 45D:
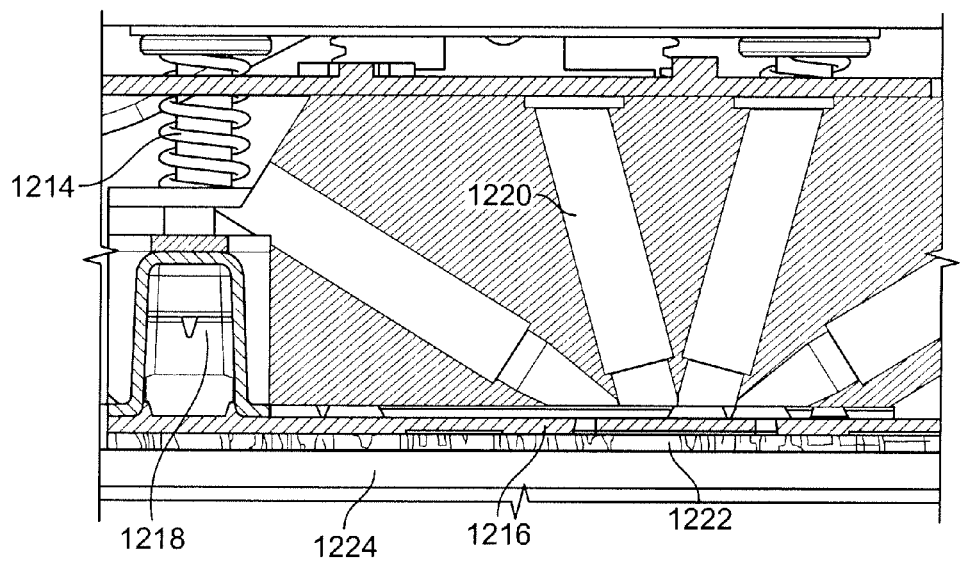

FIGS. 45C and 45D show further cross-sectional views.

Example 6

Exemplary Optics Board

Figure 46:
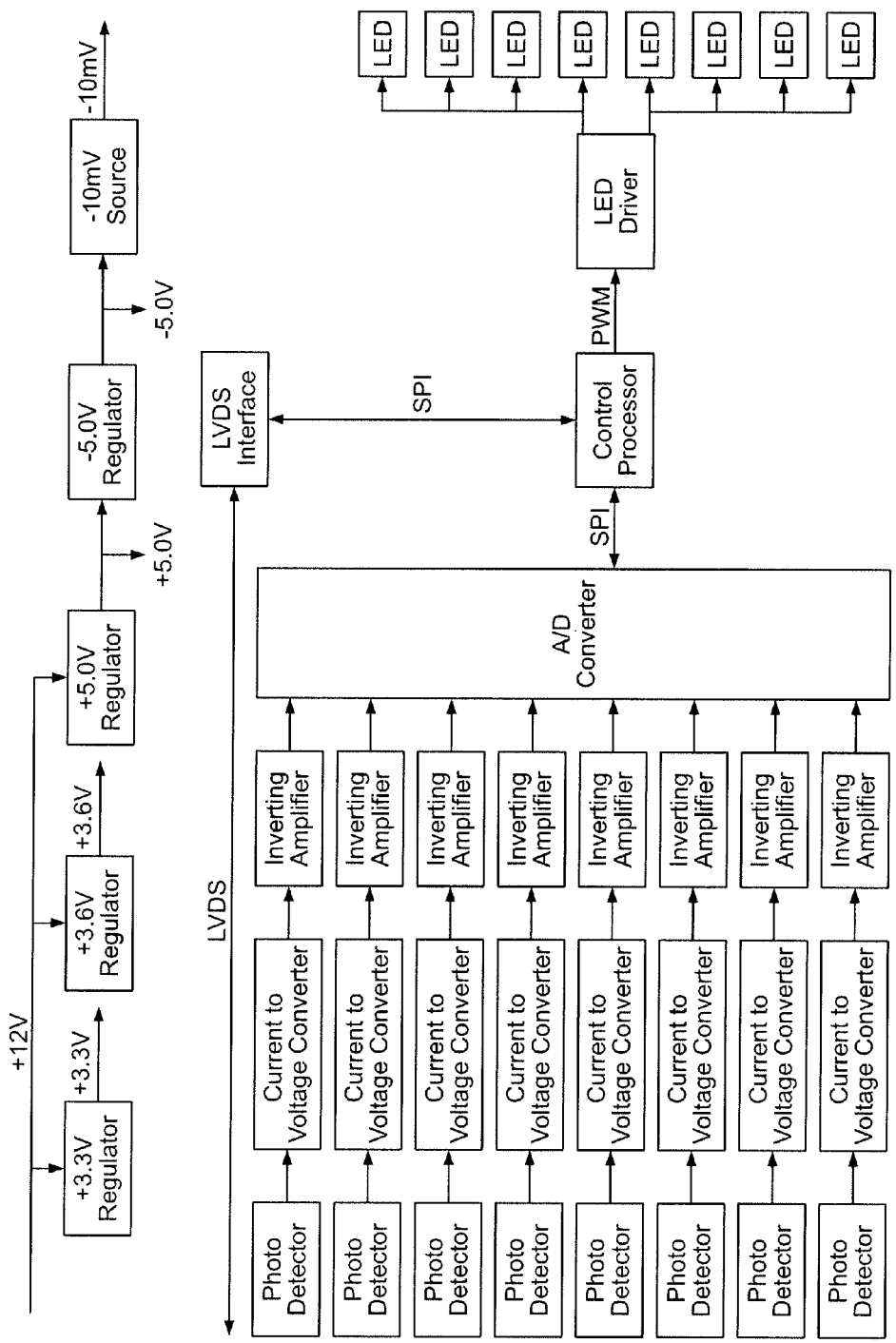
FIG. 46 shows a block diagram of exemplary electronic circuitry in conjunction with a detector as described herein.

An exemplary optics board is shown schematically in FIG. 46, and is used to collect and amplify the fluorescent signature of a successful chemical reaction on a micro-fluidic cartridge, and control the intensity of LED's using pulse-width modulation (PWM) to illuminate the cartridge sample over up to four channels, each with two color options. Additionally, it receives instructions and sends results data back over an LVDS (low-voltage differential signaling) SPI (serial peripheral interface). In some embodiments there is a separate instance of this circuitry for each PCR channel that is monitored.

The power board systems include: a +12V input; and +3.3V, +3.6V, +5V, and −5V outputs, configured as follows: the +3.3V output contains a linear regulator, is used to power the LVDS interface, should maintain a +/−5% accuracy, and supply an output current of 0.35 A; the +3.6V output contains a linear regulator, is used to power the MSP430, should maintain a +/−5% accuracy, and supply an output current of 0.35 A; the +5V output contains a linear regulator, is used to power the plus rail for op-amps, should maintain a +/−5% accuracy, and supply an output current of 0.35 A; the −5V output receives its power from the +5V supply, has a mV reference, is used to power the minus rail for op-amps and for the photo-detector bias, should maintain a +/−1% voltage accuracy, and supply an output current of 6.25 mA+/−10%. Additionally, the power board has an 80 ohm source resistance, and the main board software can enable/disable the regulator outputs.

The main board interface uses a single channel of the LVDS standard to communicate between boards. This takes place using SPI signaling over the LVDS interface which is connected to the main SPI port of the control processor. The interface also contains a serial port for in-system programming.

The optical detection system of FIG. 46 comprises a control processor, LED drivers, and a photo-detection system. In the exemplary embodiment, the control processor is a TI MSP430F1611 consisting of a dual SPI (one for main board interface, and one for ADC interface) and extended SRAM for data storage. It has the functions of power monitoring, PWM LED control, and SPI linking to the ADC and main board. The LED drivers contain NPN transistor switches, are connected to the PWM outputs of the control processor, can sink 10 mA @ 12V per LED (80 mA total), and are single channel with 2 LEDs (one of each color) connected to each. The photo-detection system has two channels and consists of a photo-detector, high-sensitivity photo-diode detector, high gain current to voltage converter, unity gain voltage inverting amplifier, and an ADC. Additionally it contains a 16 channel Sigma-delta (only utilizing the first 8 channels) which is connected to the second SPI port of the control processor.

During assembly of the various components on to the PC board, such as may occur on a production line, there are the following considerations. The extremely high impedance of the photo-detection circuit means that a rigorous cleaning procedure must be employed. Such a procedure may include, for example: After surface mount components are installed, the boards are washed on a Weskleen and blow dried upon exiting conveyor. The belt speed can be set at 20-30. The boards are soaked in an alcohol bath for approximately 3 minutes, then their entire top and bottom surfaces are scrubbed using a clean, soft bristle brush. The boards are baked in a 105° F. (40° C.) oven for 30 minutes to dry out all components.

After all the components are installed: the soldered areas of the boards can be hand wash using deionized water and a soft bristle brush. The same soldered areas can be hand washed using alcohol and a soft bristle brush. The boards are allowed to air dry. Once the board is cleaned, the optical circuitry must be conformal coated to keep contaminates out.

The foregoing description is intended to illustrate various aspects of the present technology. It is not intended that the examples presented herein limit the scope of the present technology. The technology now being fully described, it will be apparent to one of ordinary skill in the art that many changes and modifications can be made thereto without departing from the spirit or scope of the appended claims.

The invention claimed is:

1. An apparatus, comprising:
   a plurality of multi-lane microfluidic cartridges, each lane comprising a reaction zone;
   a plurality of receiving bays, each receiving bay configured to receive one of the plurality of microfluidic cartridges;
   each reaction zone comprising multiple separately controllable heaters thermally coupled thereto, the heaters configured to simultaneously and uniformly heat the reaction zone to carry out nucleic acid amplification on a polynucleotide-containing sample in the reaction zone;
   a detector configured to detect the presence of an amplification product in one or more reaction zones; and
   a processor coupled to the detector and the heaters, configured to control heating of one or more reaction zones by the heaters.

2. The apparatus of claim 1, wherein the separately controllable heaters thermally coupled to each reaction zone are configured to maintain a temperature gradient of less than 1° C. across a width of the reaction zone at any point along a length of the reaction zone.

3. The apparatus of claim 1, wherein the processor is programmable to operate the detector to detect a polynucleotide or a probe thereof in a plurality of microfluidic cartridges located in the plurality of receiving bays.

4. The apparatus of claim 1, wherein the detector comprises an optical detector, the optical detector comprising a light source that selectively emits light in an absorption band of a fluorescent dye and a light detector that selectively detects light in an emission band of the fluorescent dye, wherein the flourescent dye is used to detect a nucleic acid amplification product.

5. The apparatus of claim 4, wherein the optical detector comprises a bandpass-filtered diode that selectively emits light in the absorption band of the fluorescent dye and a bandpass filtered photodiode that selectively detects light in the emission band of the fluorescent dye.

6. The apparatus of claim 1, further comprising instructions that direct the processor to maintain a substantially uniform temperature throughout a reaction chamber thermally coupled to the heaters.

7. A device for carrying out nucleic acid amplification on a plurality of samples, the device comprising:
   a plurality of multi-lane microfluidic cartridges, each lane comprising a reaction zone;
   a plurality of receiving bays, each receiving bay configured to receive one of the plurality of microfluidic cartridges;
   a plurality of separately controllable heaters thermally coupled to each reaction zone, the heaters configured to uniformly heat the reaction zone to carry out nucleic acid amplification on a polynucleotide-containing sample in the reaction zone;
   a detector configured to detect the presence of an amplification product in one or more reaction zones;
   a processor coupled to the detector and the plurality of separately controllable heaters, configured to control heating of one or more reaction zones by the plurality of separately controllable heaters; and
   an input device coupled to the processor and configured to permit concurrent or consecutive control of the plurality of multi-lane microfluidic cartridges.

8. The device of claim 7, wherein at least one of the plurality of separately controllable heaters is a first contact heat source selected from a resistive heater, a radiator, a fluidic heat exchanger, and a Peltier device.

9. The device of claim 8, wherein the first contact heat source is thermally coupled to a distinct location in a first microfluidic cartridge received in a first receiving bay, whereby the distinct location is selectively heated.

10. The device of claim 9, wherein the distinct location has a surface area of between about 1 mm² and about 225 mm².

11. The device of claim 8, further comprising a second contact heat source configured to be independently thermally coupled to a distinct location in a second microfluidic cartridge received in a second receiving bay, whereby the distinct location in the second microfluidic cartridge is independently heated from the distinct location in the first microfluidic cartridge.

12. The device of claim 8, wherein the first contact heat source is configured to be in direct physical contact with the distinct location of the first microfluidic cartridge received in the first receiving bay.

13. The device of claim 8, further comprising a compliant layer configured to thermally couple the first contact heat source with at least a portion of the first microfluidic cartridge received in the first receiving bay.

14. The device of claim 7, wherein at least one of the plurality of separately controllable heaters is a radiative heat source configured to direct heat to a distinct location of a first microfluidic cartridge received in a first receiving bay.

15. The device of claim 7, wherein the input device is selected from the group consisting of a keyboard, a touch-sensitive surface, a microphone, a hard disk drive, an optical disk drive, a serial connection, a parallel connection, a wireless network connection, a wired network connection, and a mouse.

16. The device of claim 7, further comprising at least one sample identifier coupled to the processor, the sample identifier being selected from an optical character reader, a bar code reader, and a radio frequency tag reader.

17. The device of claim 7, further comprising at least one output coupled to the processor, the output being selected from a display, a printer, a speaker, a serial connection, a parallel connection, a wireless network connection, and a wired network connection.

18. The device of claim 7, further comprising a heating stage configured to be removable from the device, wherein at least one of the plurality of separately controllable heaters is located in the heating stage.

19. The device of claim 7, further comprising instructions that direct the processor to maintain a substantially uniform temperature throughout a reaction chamber thermally coupled to the heaters.

20. A method of carrying out nucleic acid amplification on a plurality of samples, the method comprising:
   introducing the plurality of samples into the plurality of multi-lane microfluidic cartridges of claim 1, wherein each lane comprises a reaction zone configured to permit heating of a sample independently of the other samples;
   moving the plurality of samples into the respective plurality of reaction zones; and
   heating the plurality of reaction zones in order to amplify polynucleotides contained with the plurality of samples in the plurality of multi-lane microfluidic cartridges, at least one reaction zone separately thermally controllable from another reaction zone.

21. The method of claim 20, further comprising detecting the presence of a polynucleotide or a polynucleotide probe in the plurality of samples.

22. The method of claim 20, wherein heating the reaction zones comprises maintaining a substantially uniform temperature throughout each reaction zone.

* * * * *